US008153412B2

(12) United States Patent
Chang et al.

(10) Patent No.: US 8,153,412 B2
(45) Date of Patent: Apr. 10, 2012

(54) **VARIANTS OF *BACILLUS* SP. TS-23 ALPHA-AMYLASE WITH ALTERED PROPERTIES**

(75) Inventors: Claudine Y. Chang, Mountain View, CA (US); Clement Choy, Alamo, CA (US); Melodie Estabrook, Mountain View, CA (US); Mansi Goyal, Atherton, CA (US); Thomas P. Graycar, Pacifica, CA (US); Victoria E. Huang, Sunnyvale, CA (US); Brian E. Jones, Leidschendam (NL); Marc Kolkman, Oegstgeest (NL); Karsten M. Kragh, Viby J (DK); Chris Leeflang, GA Twisk (NL); Scott D. Power, San Bruno, CA (US); Sandra W. Ramer, Sunnyvale, CA (US); Andrew Shaw, San Francisco, CA (US); Casper Vroemen, Oegstgeest (NL); Walter Weyler, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 176 days.

(21) Appl. No.: 12/264,006

(22) Filed: Nov. 3, 2008

(65) Prior Publication Data

US 2010/0021587 A1    Jan. 28, 2010

Related U.S. Application Data

(60) Provisional application No. 61/026,056, filed on Feb. 4, 2008, provisional application No. 61/059,403, filed on Jun. 6, 2008.

(51) Int. Cl.
| | |
|---|---|
| *C12N 9/28* | (2006.01) |
| *C12N 9/26* | (2006.01) |
| *C12N 9/24* | (2006.01) |
| *C12N 1/20* | (2006.01) |
| *C12N 15/00* | (2006.01) |
| *A23C 17/00* | (2006.01) |
| *A23L 1/28* | (2006.01) |
| *C11D 3/02* | (2006.01) |
| *C12D 3/00* | (2006.01) |
| *C12D 3/386* | (2006.01) |
| *C07H 21/04* | (2006.01) |
| *C07K 1/00* | (2006.01) |

(52) U.S. Cl. ........ 435/202; 435/201; 435/200; 435/183; 435/69.1; 435/252.3; 435/252.31; 435/252.33; 435/252.35; 435/254.11; 435/320.1; 426/42; 426/56; 426/64; 536/23.2; 536/23.7; 536/23.1; 510/218; 510/226; 510/300; 510/320; 510/392; 510/530; 530/350

(58) Field of Classification Search .................. 435/202, 435/201, 200, 183, 69.1, 252.3, 252.31, 252.33, 435/252.35, 254.11, 320.1; 426/42, 56, 64; 510/218, 226, 300, 392, 530; 536/23.2, 536/23.7, 23.1; 530/350
See application file for complete search history.

(56) References Cited

U.S. PATENT DOCUMENTS

| | | |
|---|---|---|
| 3,912,590 A | 10/1975 | Slott et al. |
| 4,106,991 A | 8/1978 | Markussen et al. |
| 4,316,956 A | 2/1982 | Lutzen |
| 4,335,208 A | 6/1982 | Norman |
| 4,435,307 A | 3/1984 | Barbesgaard et al. |
| 4,643,736 A | 2/1987 | Cholley |
| 4,661,452 A | 4/1987 | Markussen et al. |
| 4,683,202 A | 7/1987 | Mullis |
| 4,689,297 A | 8/1987 | Good et al. |
| 4,760,025 A | 7/1988 | Estell et al. |
| 5,231,017 A | 7/1993 | Lantero et al. |
| 5,324,649 A | 6/1994 | Arnold et al. |
| 5,648,263 A | 7/1997 | Schulein et al. |
| 5,691,178 A | 11/1997 | Schulein et al. |
| 5,776,757 A | 7/1998 | Schulein et al. |
| 5,814,501 A | 9/1998 | Becker et al. |
| 6,017,867 A | 1/2000 | Baillely et al. |
| 6,093,562 A | 7/2000 | Bisgard-Frantzen et al. |
| 6,297,038 B1 | 10/2001 | Bisgard-Frantzen et al. |
| 6,403,355 B1 | 6/2002 | Hagihara et al. |
| 6,475,762 B1 | 11/2002 | Stafford et al. |
| 6,528,298 B1 | 3/2003 | Svendsen et al. |
| 6,562,612 B2 | 5/2003 | Jones et al. |
| 6,867,031 B2 | 3/2005 | Bisgård-Frantzen et al. |
| 7,498,158 B2 | 3/2009 | Svendsen et al. |
| 7,713,723 B1 | 5/2010 | Thisted et al. |
| 2005/0250663 A1 | 11/2005 | Thisted et al. |
| 2009/0143270 A1 | 6/2009 | Svendsen et al. |
| 2009/0280527 A1 | 11/2009 | Bisgard-Frantzen et al. |

(Continued)

FOREIGN PATENT DOCUMENTS

EP    0 063 909 A2    11/1982

(Continued)

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*

(Continued)

*Primary Examiner* — Ganapathirama Raghu
(74) *Attorney, Agent, or Firm* — Drinker Biddle & Reath LLP

(57) ABSTRACT

Variants of *Bacillus* sp. TS-23 strain alpha-amylases exhibit improved enzymatic performance, including increased themostability, reduced calcium dependence, increased washing/cleaning performance, and baking ability. Compositions comprising these variants are useful in methods of starch processing, starch liquefaction, fermatation, starch saccharification, cleaning, laundrying, textile desizing, baking, and biofilm removal.

35 Claims, 17 Drawing Sheets

U.S. PATENT DOCUMENTS

| | | | |
|---|---|---|---|
| 2010/0048446 A1* | 2/2010 | Cascao-Pereira et al. | .... 510/226 |
| 2010/0099597 A1 | 4/2010 | Bisgard-Frantzen et al. | |
| 2010/0099598 A1 | 4/2010 | Bisgard-Frantzen et al. | |

FOREIGN PATENT DOCUMENTS

| | | | |
|---|---|---|---|
| EP | 0 119 920 A2 | 9/1984 | |
| EP | 0 218 272 A1 | 4/1987 | |
| EP | 0 238 023 A2 | 9/1987 | |
| EP | 0 238 216 A1 | 9/1987 | |
| EP | 0 252 666 A2 | 1/1988 | |
| EP | 0 252 730 A2 | 1/1988 | |
| EP | 0 258 068 A2 | 3/1988 | |
| EP | 0 260 105 A2 | 3/1988 | |
| EP | 0 305 216 A1 | 3/1989 | |
| EP | 0 331 376 A2 | 9/1989 | |
| EP | 0 407 225 A1 | 1/1991 | |
| EP | 0 815 208 B1 | 1/1998 | |
| EP | 1 199 356 A2 | 4/2002 | |
| EP | 1 423 513 B1 | 6/2004 | |
| EP | 1 538 155 B1 | 6/2005 | |
| GB | 1296839 A | 11/1972 | |
| GB | 1372034 A | 10/1974 | |
| GB | 1483591 A | 8/1977 | |
| JP | 64-074992 A | 3/1989 | |
| WO | WO 89/06270 A1 | 7/1989 | |
| WO | WO 89/06279 A1 | 7/1989 | |
| WO | WO 91/00353 A2 | 1/1991 | |
| WO | WO 91/16422 A1 | 10/1991 | |
| WO | WO 91/17243 A1 | 11/1991 | |
| WO | WO 92/05249 A1 | 4/1992 | |
| WO | WO 92/06165 A1 | 4/1992 | |
| WO | WO 92/06221 A1 | 4/1992 | |
| WO | WO 92/19708 A1 | 11/1992 | |
| WO | WO 92/19709 A1 | 11/1992 | |
| WO | WO 92/19729 A1 | 11/1992 | |
| WO | WO 93/24618 A1 | 12/1993 | |
| WO | WO 94/01541 A1 | 1/1994 | |
| WO | WO 94/02597 A1 | 2/1994 | |
| WO | WO 94/18314 A1 | 8/1994 | |
| WO | WO 94/25578 A1 | 11/1994 | |
| WO | WO 94/25583 A1 | 11/1994 | |
| WO | WO 95/06720 A1 | 3/1995 | |
| WO | WO 95/10602 A1 | 4/1995 | |
| WO | WO 95/14783 A1 | 6/1995 | |
| WO | WO 95/14807 A1 | 6/1995 | |
| WO | WO 95/21247 A1 | 8/1995 | |
| WO | WO 95/22615 A1 | 8/1995 | |
| WO | WO 95/22625 A1 | 8/1995 | |
| WO | WO 95/26397 A1 | 10/1995 | |
| WO | WO 95/30744 A2 | 11/1995 | |
| WO | WO 95/35381 A1 | 12/1995 | |
| WO | WO 96/00292 A1 | 1/1996 | |
| WO | WO 96/12012 A1 | 4/1996 | |
| WO | WO 96/13580 A1 | 5/1996 | |
| WO | WO 96/23873 A1 | 8/1996 | |
| WO | WO 96/27002 A1 | 9/1996 | |
| WO | WO 96/28567 A1 | 9/1996 | |
| WO | WO 96/39528 A2 | 12/1996 | |
| WO | WO 97/00324 A1 | 1/1997 | |
| WO | WO 97/04079 A1 | 2/1997 | |
| WO | WO 97/07202 A1 | 2/1997 | |
| WO | WO 97/07205 A1 | 2/1997 | |
| WO | WO 97/43424 A1 | 11/1997 | |
| WO | WO 98/15257 A1 | 4/1998 | |
| WO | WO 98/20115 A1 | 5/1998 | |
| WO | WO 98/20116 A1 | 5/1998 | |
| WO | WO 98/23732 A2 | 6/1998 | |
| WO | WO 98/34946 A1 | 8/1998 | |
| WO | WO 99/19467 A1 | 4/1999 | |
| WO | WO 99/20770 A2 | 4/1999 | |
| WO | WO 99/49740 A1 | 10/1999 | |
| WO | WO 00/60060 A2 | 10/2000 | |
| WO | WO 02/10355 A2 | 2/2002 | |
| WO | WO 02/14490 A2 | 2/2002 | |
| WO | WO 02/092797 | * 11/2002 | |
| WO | WO 2004/091544 A | 8/2004 | |
| WO | 2004/113551 A1 | 12/2004 | |
| WO | WO 2006/002643 A2 | 1/2006 | |
| WO | WO 2006/037483 | * 4/2006 | |
| WO | WO 2006/043178 A2 | 4/2006 | |
| WO | WO 2008/153925 A2 | 12/2008 | |

OTHER PUBLICATIONS

Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
U.S. Appl. No. 10/576,331, filed Jul. 18, 2007, Jones et al.
U.S. Appl. No. 10/630,203, filed Nov. 10, 2005, Thisted et al.
U.S. Appl. No. 11/581,102, filed Nov. 27, 2008, Shaw et al.
U.S. Appl. No. 11/583,334, filed Oct. 19, 2006, Aehle et al.
U.S. Appl. No. 11/714,487, filed Sep. 11, 2008, Cervin et al.
Altschul, S.F. et al. "Gapped BLAST and PSI-BLAST: a new generation of protein database search programs." *Nucleic Acids Res.* 25: 3389-3402, 1997.
Beaucage, S.L. et al. "Deoxynucleoside phosphoramidites—A new class of key intermediates for deoxypolynucleotide synthesis." *Tetrahedron Lett.* 22(20): 1859-1862, 1981.
Dartois, V. et al. "Cloning, nucleotide sequence and expression in *Escherichia coli* of a lipase gene from *Bacillus subtilis* 168." *Biochimica et Biophysica Acta* 1131(3): 253-260, Jul. 15, 1992.
Engelen, A.J. et al. "Simple and rapid determination of phytase activity." *Journal of AOAC International* 77(3): 760-764, Jun. 1994.
Freire, E. "Differential Scanning Calorimetry." In *Protein Stability and Folding: Theory and Practice*, edited by B.A. Shirley, pp. 191-218. Methods in Molecular Biology 40. New York: Humana Press, 1995.
Gaboriaud, C. et al. "Hydrophobic cluster analysis: an efficient new way to compare and analyse amino acid sequences." *FEBS Letters* 224(1): 149-55, Nov. 16, 1987.
Hage, R. et al. "Efficient manganese catalysts for low-temperature bleaching." *Nature* 369(6482): 637-639, Jun. 23, 1994.
Hahn, J. et al. "Regulatory inputs for the synthesis of ComK, the competence transcription factor of *Bacillus subtilis.*" *Molecular Microbiology* 21(4): 763-775, 1996.
Huber, T. et al. "Protein fold recognition without Boltzmann statistics or explicit physical basis." *Protein Science* 7(1): 142-149, 1998.
Lin L-L et al. "A gene encoding for an alpha-amylase from thermophilic *Bacillus* sp. strain TS-23 and its expression in *Escherichia coli*", Journal of Applied Microbiology, vol. 82, No. 3, 1997, pp. 325-334, XP002514257, ISSN 1364-5072 abstract.
Matthes, H.W.D. et al. "Simultaneous rapid chemical synthesis of over one hundred oligonucleotides on a microscale." *EMBO J.* 3(4): 801-805, Apr. 1984.
McKenzie, T. et al. "The nucleotide sequence of pUB110: some salient features in relation to replication and its regulation." *Plasmid* 15(2): 93-103, Mar. 1986.
Morinaga, Y. et al. "Improvement of Oligonucleotide-Directed Site-Specific Mutagenesis Using Double-Stranded Plasmid DNA." *Bio/Technology* 2(7): 636-639, Jul. 1984.
Needleman, S.B. et al. "A general method applicable to the search for similarities in the amino acid sequence of two proteins." *J. Mol. Biol* 48(3): 443-53, Mar. 1970.
Neidhardt, F.C. et al. "Culture Medium for Enterobacteria." *J. Bacteriol.* 119(3): 736-747, Sep. 1, 1974.
Nelson, R.M. et al. "A general method of site-specific mutagenesis using a modification of the *Thermus aquaticus* polymerase chain reaction." *Analytical Biochemistry* 180(1): 147-151, Jul. 1989.
Nielsen J.E. et al. "Protein Engineering of bacterial Alpha-amylases", Biochimica et Biophysica Acta, Amsterdam, vol. 1543, No. 2, Dec. 29, 2000, pp. 253-274, XP 000984337, ISSN 0006-30002.
Pearson, W.R. et al. "Improved Tools for Biological Sequence Comparison." *Proc. Natl. Acad. Sci. USA* 85(8): 2444-2448, Apr. 15, 1988.
Saiki, R.K. et al. "Primer-directed enzymatic amplification of DNA with a thermostable DNA polymerase." Science 239(4839): 487-491, Jan. 29, 1988.

Suzuki Y. et al. "Amino Acid Residues Stabilizing a *Bacillus* Alpha-Amylase against irreversible thermoactivation", Journal of Biological Chemistry, American Society of Biolochemical Biologists, Birmingham, US vol. 264, No. 32, Nov. 15, 1989, pp. 18933-18938, XP 000872071, ISSN 0021-9258.

Tomazic S J et al. "Why is one *Bacillus* Alpha-Amylase more resistant against irreversible thermoinactivation than another?" Journal of Biological Chemistry, American Society of Biolochmical Biologists, Birmingham, US, vol. 263, No. 7, Mar. 5, 1988, pp. 3092-3096, XP 001015592, ISSN 0021,-9258.

Tsukamoto, A. et al. "Nucleotide sequence of the maltohexaose-producing amylase gene from an alkalophilic *Bacillus* sp. #707 and structural similarity to liquefying type alpha-amylases." *Biochemical and Biophysical Research Communications* 151(1): 25-31, Feb. 29, 1988.

Vogtentanz, G. et al. "A *Bacillus subtilis* fusion protein system to produce soybean Bowman-Birk protease inhibitor." *Protein Expression and Purification* 55(1): 40-52, Sep. 2007.

International Search Report for PCT/US2008/012411, mailed Jul. 7, 2009.

International Search Report for PCT/US2008/012410, mailed May 13, 2009.

International Search Report for PCT/US2008/012412, mailed Jul. 21, 2009.

Database UnitProt [Online], Aug. 22, 2006 "Subname: Full=Alpha amylase, catalytic region; Flags: Precursor;" XP 00254542.

Mi-Sook Kim et al "Changes in Optimum PH and Thermostability of Alpha-Amylase from *Bacillus licheniformis* by Site-Directed Mutagenesis of his 235 and ASP 328" Bulletin of the Korean Chemical Society, Korean Chemical Society, Seoul, KR, vol. 15, No. 10, Oct. 20, 1994 pp. 832-835.

PCT Search Report for Int'l Appln No. PCT/US2008/012413, mailed Sep. 30, 2009.

U.S. Appl. No. 12/758,346, Requirement for Restriction/Election mailed Oct. 18, 2010.

Lin et al., "A gene encoding for an α-amylase from thermophilic *Bacillus* sp. Strain TS-23 and its expression in *Escherichia coli*," Journal of Applied Microbiology, (1997), vol. 82, pp. 325-334.

Lin et al., "Production and properties of a raw-starch-degrading amylase from the thermophilic and alkaliphilic *Bacillus* sp. TS-23," Biotechnol. Appl. Biochem (1998) vol. 28, pp. 61-68.

Lin et al., "General characteristics of thermostable amylopullulanases and amylases from the alkalophilic *Bacillus* sp. TS-23," Appl. Microbiol. Biotechnol (1994) vol. 42, pp. 51-56.

Gray et al. "Structural Genes Encoding the Termophiliic α-amylase of *Bacillus stearothermophilus* and *Bacillus licheniformis*," Journal of Bacteriology, (May 1986), vol. 166, No. 2, pp. 635-643.

Chen et al., "Structure and expression of an amylopullulanase gene from *Bacillus stearothermophilus* TS-23," Biotechnol. Appl. Biochem (2001) vol. 33, pp. 189-199.

Lin et al., "Impact of Arg210-Ser211 deletion of thermostability of a truncated *Bacillus* sp. Strain TS-23 α-amylase," Process Biochemistry, vol. 43 (2008) pp. 559-565.

U.S. Appl. No. 12/365,646, Requirement for Restriction/Election, mailed Oct. 18, 2010.

U.S. Appl. No. 12/365,646, Non-Final Rejection, mailed Mar. 2, 2011.

Chica et al., "Semi-rational approaches to engineering enzyme activity: combining the benefits of directed evolution and rational design," *Curr. Opinion Biotechnol*. 16(4): 378-84 (2005).

Sen et al., "Developments in directed evolution for improving enzyme functions," *Appl. Biochem. Biotechnol*. 143(3): 212-23 (2007).

Swiss-Prot Accession No. Q59222 (1996).

Sivaramakrishnan et al., *Food Technol. Biotech*. 44:173-44 (2006).

U.S. Appl. No. 12/365,646, Final Rejection, mailed Aug. 3, 2011.

* cited by examiner

Ntapinetmmqyfewdlpndgtlwtkvkneaanlsslgitalwlppaykgtsqsdvgygvydlyd
lgefnqkgtirtkygtktqyiqaiqaakaagmqvyadvvfnhkagadgtefvdavevdpsnrnqe
tsgtyqiqawtkfdfpgrgntyssfkwrwyhfdgtdwdesrklnriykfrstgkawdwevdteng
nydylmfadldmdhpevvtelknwgtwyvnttnidgfrldavkhikysffpdwltyvrnqtgknl
favgefwsydvnklhnyitktngsmslfdaplhnnfytaskssgyfdmryllnntlmkdqpslav
tlvdnhdtqpgqslqswvepwfkplayafiltrqegypcvfygdyygipkynipglkskidplli
arrdyaygtqrdyidhqdiigwtregidtkpnsglaalitdgpggskwmyvgkkhagkvfydltg
nrsdtvtinadgwgefkvnggsvsiwvaktsnvtftvnnatttsgqnvyvvanipelgnwntana
ikmnpssyptwkatialpqgkaiefkfikkdqagnviwestsnrtytvpfsstgsytaswnvp (SEQ ID NO: 1)

FIG. 1

Ntapinetmmqyfewdlpndgtlwtkvkneaanlsslgitalwlppaykgtsqsdvgygvydlyd
lgefnqkgtirtkygtktqyiqaiqaakaagmqvyadvvfnhkagadgtefvdavevdpsnrnqe
tsgtyqiqawtkfdfpgrgntyssfkwrwyhfdgtdwdesrklnriykfrstgkawdwevdteng
nydylmfadldmdhpevvtelknwgtwyvnttnidgfrldavkhikysffpdwltyvrnqtgknl
favgefwsydvnklhnyitktngsmslfdaplhnnfytaskssgyfdmryllnntlmkdqpslav
tlvdnhdtqpgqslqswvepwfkplayafiltrqegypcvfygdyygipkynipglkskidplli
arrdyaygtqrdyidhqdiigwtregidtkpnsglaalitdgpggskwmyvgkkhagkvfydltg
nrsdtvtinadgwgefkvnggsvsiwvak (SEQ ID NO: 2)

FIG. 2

```
aatacggcgccgatcaacgaaacgatgatgcagtattttgaatgggatctgccgaatgatggaac
gctgtggacgaaagtcaaaaacgaagcggcgaatcttagcagcctgggaatcacagcactttggc
ttccgccggcatataaaggaacgagccaaagcgatgtcggctatggcgtctatgatctgtatgac
ctgggcgaatttaaccaaaaaggcacgatccggacgaaatatggcacgaaaacacagtatatcca
agcgatccaggcagcaaaagcagcaggcatgcaagtctatgccgacgtcgtctttaatcataaag
cgggagcggatggcacagaatttgtcgatgccgtcgaagttgatccgagcaacagaaaccaagaa
acgagcggcacgtatcaaatccaagcgtggacgaaatttgattttccgggcagaggcaatacgta
tagcagctttaaatggcgctggtatcattttgacggcacggattgggatgaaagcagaaaactga
accggatctataaatttcggagcacgggcaaagcatgggattgggaagtcgatacggaaaacggc
aactatgactatctgatgtttgccgatctggatatggatcatccggaagtcgtcacggaactgaa
aaattggggcacgtggtatgttaatacgacgaacatcgatggctttagactggatgccgtcaaac
atatcaaatatagctttttccggactggctgacgtatgtcagaaaccagacgggcaaaaacctt
tttgccgtcggcgaattttggagctatgacgtcaacaaacttcataactatatcacgaaaacgaa
cggcagcatgagccttttgatgccccgcttcataacaacttttatacggcgagcaaaagctcag
gctattttgatatgagatatctgctgaacaacacgctgatgaaagatcaaccgagcctggcagtc
acactggtcgataaccatgatacacaaccgggccaaagccttcaaagctgggtcgaaccgtggtt
taaaccgctggcgtatgcctttatcctgacgagacaagaagggtatccttgcgtcttttatggcg
actattatggcatcccgaaatataatatcccgggcctgaaaagcaaaatcgatccgctgctgatc
gccagacgggattatgcctatggcacacagcgggattatatcgaccatcaggacatcatcggctg
gacaagagaaggcatcgatacgaaaccgaatagcggactggcagcactgattacagatggaccgg
gcggaagcaaatggatgtatgtcggcaaaaaacatgccggcaaagtcttttatgatctgacgggc
aacagaagcgatacggtcacgatcaatgctgatggctggggagaatttaaagtcaatggcggcag
cgtttcaatctgggtcgccaaaacgagcaatgtcacgtttacggtcaacaatgccacgacaacga
gcggccaaaatgtctatgtcgtcgccaatatcccggaactgggcaattggaatacggcgaacgca
atcaaaatgaacccgagcagctatccgacatgaaagcgacaatcgctctgccgcaaggaaaagc
gatcgaatttaaatttatcaaaaagaccaggcgggcaatgttatttgggaaagcacgagcaata
gaacgtatacggtcccgtttagcagcacaggaagctatacagcgagctggaatgttccgtga
```

(SEQ ID NO: 3)

FIG. 3

```
aatacggcgccgatcaacgaaacgatgatgcagtattttgaatgggatctgccgaatgatggaac
gctgtggacgaaagtcaaaaacgaagcggcgaatcttagcagcctgggaatcacagcactttggc
ttccgccggcatataaaggaacgagccaaagcgatgtcggctatggcgtctatgatctgtatgac
ctgggcgaatttaaccaaaaaggcacgatccggacgaaatatggcacgaaaacacagtatatcca
agcgatccaggcagcaaaagcagcaggcatgcaagtctatgccgacgtcgtctttaatcataaag
cggagcggatggcacagaatttgtcgatgccgtcgaagttgatccgagcaacagaaaccaagaa
acgagcggcacgtatcaaatccaagcgtggacgaaatttgattttcgggcagaggcaatacgta
tagcagctttaaatggcgctggtatcattttgacggcacggattgggatgaaagcagaaaactga
accggatctataaatttcggagcacgggcaaagcatgggattgggaagtcgatacggaaaacggc
aactatgactatctgatgtttgccgatctggatatggatcatccggaagtcgtcacggaactgaa
aaattggggcacgtggtatgttaatacgacgaacatcgatggctttagactggatgccgtcaaac
atatcaaatatagcttttttccggactggctgacgtatgtcagaaaccagacgggcaaaaacctt
tttgccgtcggcgaattttggagctatgacgtcaacaaacttcataactatatcacgaaaacgaa
cggcagcatgagccttttttgatgccccgcttcataacaacttttatacggcgagcaaaagctcag
gctattttgatatgagatatctgctgaacaacacgctgatgaaagatcaaccgagcctggcagtc
acactggtcgataaccatgatacacaaccgggccaaagccttcaaagctgggtcgaaccgtggtt
taaaccgctggcgtatgcctttatcctgacgagacaagaagggtatccttgcgtcttttatggcg
actattatggcatcccgaaatataatatcccgggcctgaaaagcaaaatcgatccgctgctgatc
gccagacgggattatgcctatggcacacagcgggattatatcgaccatcaggacatcatcggctg
gacaagagaaggcatcgatacgaaaccgaatagcggactggcagcactgattacagatggaccgg
gcggaagcaaatggatgtatgtcggcaaaaaacatgccggcaaagtcttttatgatctgacgggc
aacagaagcgatacggtcacgatcaatgctgatggctggggagaatttaaagtcaatggcggcag
cgtttcaatctgggtcgccaaatga  (SEQ ID NO: 4)
```

*FIG. 4*

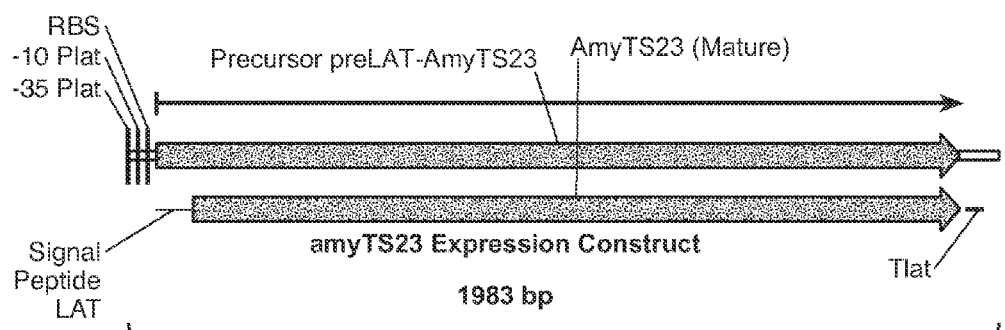

*FIG. 5*

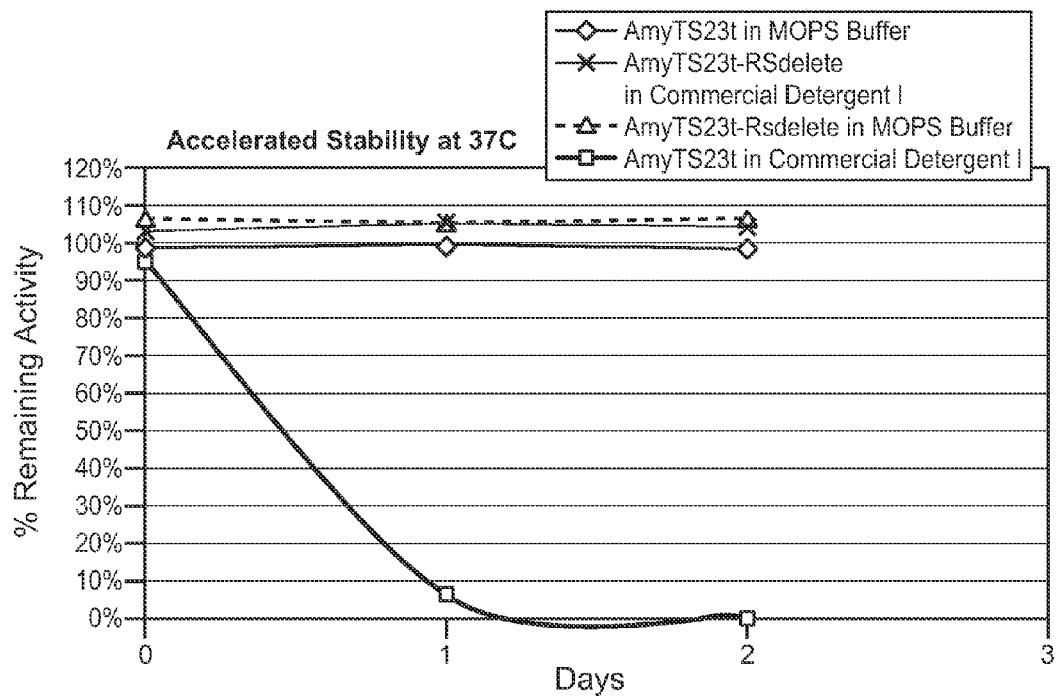

FIG. 10 ntapinetmmqyfewdlpndgtlwtkvkneaanlsslgitalwlppaykgtsqsdvgygvydlyd
lgefnqkgtirtkygtktqyiqaiqaakaagmqvyadvvfnhkagadgtefvdavevdpsnrnqe
tsgtyqiqawtkfdfpgrgntyssfkwrwyhfdgtdwdesrklnriykftgkawdwevdtengny
dylmfadldmdhpevvtelknwgtwyvnttnidgfrldavkhikysffpdwltyvrnqtgknlfa
vgefwsydvnklhnyitktngsmslfdaplhnnfytaskssgyfdmryllnntlmkdqpslavtl
vdnhdtqpgqslqswvepwfkplayafiltrqegypcvfygdyygipkynipglkskidpllia r
rdyaygtqrdyidhqdiigwtregidtkpnsglaalitdgpggskwmyvgkkhagkvfydltgnr
sdtvtinadgwgefkvnggsvsiwvak (SEQ ID NO: 5)

FIG. 11

```
aaaattcggaatatttatacaatatcatatgtttcacattgaaaggggaggagaatcatgaaacaacaaaaacggctt
tacgcccgattgctgacgctgttatttgcgctcatcttcttgctgcctcattctgcagcttcagcaaatacggcgccg
atcaacgaaacgatgatgcagtattttgaatgggatctgccgaatgatggaacgctgtggacgaaagtcaaaaacgaa
gcggcgaatcttagcagcctggggaatcacagcactttggcttccgccggcatataaaggaacgagccaaagcgatgtc
ggctatggcgtctatgatctgtatgacctgggcgaatttaaccaaaaaggcacgatccggacgaaatatggcacgaaa
acacagtatatccaagcgatccaggcagcaaaagcagcaggcatgcaagtctatgccgacgtcgtctttaatcataaa
gcgggagcggatggcacagaatttgtcgatgccgtcgaagttgatccgagcaacagaaaccaagaaacgagcggcacg
tatcaaatccaagcgtggacgaaatttgattttccgggcagaggcaatacgtatagcagcttttaaatggcgctggtat
catttttgacggcacggattgggatgaaagcagaaaactgaaccggatctataaatttcggagcacgggcaaagcatgg
gattgggaagtcgatacggaaaacggcaactatgactatctgatgtttgccgatctggatatggatcatccggaagtc
gtcacggaactgaaaaattgggcacgtggtatgttaatacgacgaacatcgatggctttagactggatgccgtcaaa
catatcaaatatagctttttccggactggctgacgtatgtcagaaaccagacgggcaaaaaccttttttgccgtcggc
gaattttggagctatgacgtcaacaaacttcataactatatcacgaaaacgaacggcagcatgagccttttttgatgcc
ccgcttcataacaacttttatacggcgagcaaaagctcaggctattttgatatgagatatctgctgaacaacacgctg
atgaaagatcaaccgagcctggcagtcacactggtcgataaccatgatacacaaccgggccaaagccttcaaagctgg
gtcgaaccgtggtttaaaccgctgtcgcgtatgcctttatcctgacgagacaagaagggtatccttgcgtcttttatggc
gactattatggcatcccgaaatataatatcccgggcctgaaaagcaaaatcgatccgctgctgatcgccagacgggat
tatgcctatggcacacagcgggattatatcgaccatcaggacatcatcggctggacaagagaaggcatcgatacgaaa
ccgaatagcggactggcagcactgattacagatggaccgggcggaagcaaatggatgtatgtcggcaaaaaacatgcc
ggcaaagtcttttatgatctgacgggcaacagaagcgatacggtcacgatcaatgctgatggctgggggagaatttaaa
gtcaatggcggcagcgtttcaatctgggtcgccaaaacgagcaatgtcacgtttacggtcaacaatgccacgacaacg
agcggccaaaatgtctatgtcgtcgccaatatcccggaactgggcaattggaatacggcgaacgcaatcaaaatgaac
ccgagcagctatccgacatggaaagcgacaatcgctctgccgcaaggaaaagcgatcgaatttaaatttatcaaaaaa
gaccaggcgggcaatgttatttgggaaagcacgagcaatagaacgtatacggtccgtttagcagcacaggaagctat
acagcgagctggaatgttccgtgagttaacagaggacggatttcctgaaggaaatccgtttttttattttaagcttgg
agacaaggtaaaggataaaacctcgag
```

FIG. 18A

```
ntapinetmmqyfewdlpndgtlwtkvkneaanlsslgitalwlppaykgtsqsdvgygvydlydlgefnqkgtirtk
ygtktqyiqaiqaakaagmqvyadvvfnhkagadgtefvdavevdpsnrnqetsgtyqiqawtkfdfpgrgntyssfk
wrwyhfdgtdwdesrklnriykfrstgkawdwevdtengnydylmfadldmdhpevvtelknwgtwyvnttnidgfrl
davkhikysffpdwltyvrnqtgknlfavgefwsydvnklhnyitktngsmslfdaplhnnfytaskssgyfdmryll
nntlmkdqpslavtlvdnhdtqpgqslqswvepwfkplayafiltrqegypcvfygdyygipkynipglkskidplli
arrdyaygtqrdyidhqdiigwtregidtkpnsglaalitdgpggskwmyvgkkhagkvfydltgnrsdtvtinadgw
gefkvnggsvsiwvak
```

FIG. 18B

SEQUENCE LISTING

<160> NUMBER OF SEQ ID NOS: 18

<210> SEQ ID NO 1
<211> LENGTH: 583
<212> TYPE: PRT
<213> ORGANISM: Bacillus sp.

<400> SEQUENCE: 1

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365
```

```
Asp Tyr Tyr Gly Ile Pro Lys Tyr Asn Ile Pro Gly Leu Lys Ser Lys
        370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
            405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
        450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
        515                 520                 525

Pro Thr Trp Lys Ala Thr Ile Ala Leu Pro Gln Gly Lys Ala Ile Glu
530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
            580

<210> SEQ ID NO 2
<211> LENGTH: 484
<212> TYPE: PRT
<213> ORGANISM: Bacillus sp.

<400> SEQUENCE: 2

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160
```

```
His Phe Asp Gly Thr Asp Trp Asp Glu Ser Arg Lys Leu Asn Arg Ile
            165                 170                 175
Tyr Lys Phe Arg Ser Thr Gly Lys Ala Trp Asp Trp Glu Val Asp Thr
        180                 185                 190
Glu Asn Gly Asn Tyr Asp Tyr Leu Met Phe Ala Asp Leu Asp Met Asp
            195                 200                 205
His Pro Glu Val Val Thr Glu Leu Lys Asn Trp Gly Thr Trp Tyr Val
210                 215                 220
Asn Thr Thr Asn Ile Asp Gly Phe Arg Leu Asp Ala Val Lys His Ile
225                 230                 235                 240
Lys Tyr Ser Phe Phe Pro Asp Trp Leu Thr Tyr Val Arg Asn Gln Thr
                245                 250                 255
Gly Lys Asn Leu Phe Ala Val Gly Glu Phe Trp Ser Tyr Asp Val Asn
            260                 265                 270
Lys Leu His Asn Tyr Ile Thr Lys Thr Asn Gly Ser Met Ser Leu Phe
        275                 280                 285
Asp Ala Pro Leu His Asn Asn Phe Tyr Thr Ala Ser Lys Ser Ser Gly
    290                 295                 300
Tyr Phe Asp Met Arg Tyr Leu Leu Asn Asn Thr Leu Met Lys Asp Gln
305                 310                 315                 320
Pro Ser Leu Ala Val Thr Leu Val Asp Asn His Asp Thr Gln Pro Gly
                325                 330                 335
Gln Ser Leu Gln Ser Trp Val Glu Pro Trp Phe Lys Pro Leu Ala Tyr
            340                 345                 350
Ala Phe Ile Leu Thr Arg Gln Glu Gly Tyr Pro Cys Val Phe Tyr Gly
        355                 360                 365
Asp Tyr Tyr Gly Ile Pro Lys Tyr Asn Ile Pro Gly Leu Lys Ser Lys
    370                 375                 380
Ile Asp Pro Leu Leu Ile Ala Arg Arg Asp Tyr Ala Tyr Gly Thr Gln
385                 390                 395                 400
Arg Asp Tyr Ile Asp His Gln Asp Ile Ile Gly Trp Thr Arg Glu Gly
                405                 410                 415
Ile Asp Thr Lys Pro Asn Ser Gly Leu Ala Ala Leu Ile Thr Asp Gly
            420                 425                 430
Pro Gly Gly Ser Lys Trp Met Tyr Val Gly Lys Lys His Ala Gly Lys
        435                 440                 445
Val Phe Tyr Asp Leu Thr Gly Asn Arg Ser Asp Thr Val Thr Ile Asn
    450                 455                 460
Ala Asp Gly Trp Gly Glu Phe Lys Val Asn Gly Gly Ser Val Ser Ile
465                 470                 475                 480
Trp Val Ala Lys

<210> SEQ ID NO 3
<211> LENGTH: 1752
<212> TYPE: DNA
<213> ORGANISM: Bacillus sp.

<400> SEQUENCE: 3
aatacggcgc cgatcaacga aacgatgatg cagtattttg aatgggatct gccgaatgat      60
ggaacgctgt ggacgaaagt caaaaacgaa gcggcgaatc ttagcagcct gggaatcaca     120
gcactttggc ttccgccggc atataaagga acgagccaaa gcgatgtcgg ctatggcgtc     180
tatgatctgt atgacctggg cgaatttaac caaaaaggca cgatccggac gaaatatggc     240
acgaaaacac agtatatcca agcgatccag gcagcaaaag cagcaggcat gcaagtctat     300
```

```
gccgacgtcg tctttaatca taaagcggga gcggatggca cagaatttgt cgatgccgtc      360
gaagttgatc cgagcaacag aaaccaagaa acgagcggca cgtatcaaat ccaagcgtgg      420
acgaaatttg attttccggg cagaggcaat acgtatagca gctttaaatg gcgctggtat      480
cattttgacg gcacggattg ggatgaaagc agaaaactga accggatcta taaatttcgg      540
agcacgggca agcatggga ttggaagtc gatacgaaa acggcaacta tgactatctg        600
atgtttgccg atctggatat ggatcatccg gaagtcgtca cggaactgaa aaattggggc      660
acgtggtatg ttaatacgac gaacatcgat ggctttagac tggatgccgt caaacatatc      720
aaatatagct ttttccgga ctggctgacg tatgtcagaa ccagacggg caaaaaccatt      780 tttgccgtcg gcgaattttg gagctatgac gtcaacaaac ttcataacta tatcacgaaa      840
acgaacggca gcatgagcct ttttgatgcc ccgcttcata caacttttta tacggcgagc      900
aaaagctcag gctattttga tatgagatat ctgctgaaca cacgctgat gaaagatcaa       960 ccgagcctgg cagtcacact ggtcgataac catgatacac aaccgggcca aagccttcaa     1020
agctgggtcg aaccgtggtt taaaccgctg gcgtatgcct ttatcctgac gagacaagaa     1080
gggtatcctt gcgtctttta tggcgactat tatggcatcc cgaaatataa tatcccgggc     1140
ctgaaaagca aaatcgatcc gctgctgatc gccagacggg attatgccta tggcacacag     1200
cgggattata tcgaccatca ggacatcatc ggctggacaa gagaaggcat cgatacgaaa     1260
ccgaatagcg gactggcagc actgattaca gatggaccgg gcggaagcaa atggatgtat     1320
gtcggcaaaa aacatgccgg caaagtcttt tatgatctga cggcaacag aagcgatacg     1380 gtcacgatca atgctgatgg ctggggagaa tttaaagtca atgcggcag cgtttcaatc     1440 tgggtcgcca aaacgagcaa tgtcacgttt acggtcaaca atgccacgac aacgagcggc     1500
caaaatgtct atgtcgtcgc caatatcccg gaactgggca attggaatac ggcgaacgca     1560
atcaaaatga cccgagcag ctatccgaca tggaaagcga caatcgctct gccgcaagga     1620
aaagcgatcg aatttaaatt tatcaaaaaa gaccaggcgg gcaatgttat ttgggaaagc     1680
acgagcaata aacgtatac ggtcccgttt agcagcacag aagctatac agcgagctgg     1740 aatgttccgt ga                                                        1752

<210> SEQ ID NO 4
<211> LENGTH: 1455
<212> TYPE: DNA
<213> ORGANISM: Bacillus sp.

<400> SEQUENCE: 4
aatacggcgc cgatcaacga aacgatgatg cagtatttttg aatgggatct gccgaatgat       60
ggaacgctgt ggacgaaagt caaaaacgaa gcggcgaatc ttagcagcct gggaatcaca      120
gcactttggc ttccgccggc atataaagga acgagccaaa gcgatgtcgg ctatggcgtc      180
tatgatctgt atgacctggg cgaatttaac caaaaaggca cgatccggac gaaatatggc      240
acgaaaacac agtatatcca agcgatccag gcagcaaaag cagcaggcat gcaagtctat      300
gccgacgtcg tctttaatca taaagcggga gcggatggca cagaatttgt cgatgccgtc      360
gaagttgatc cgagcaacag aaaccaagaa acgagcggca cgtatcaaat ccaagcgtgg      420
acgaaatttg attttccggg cagaggcaat acgtatagca gctttaaatg gcgctggtat      480
cattttgacg gcacggattg ggatgaaagc agaaaactga accggatcta taaatttcgg      540
agcacgggca agcatggga ttggaagtc gatacgaaa acggcaacta tgactatctg        600
atgtttgccg atctggatat ggatcatccg gaagtcgtca cggaactgaa aaattggggc      660
```

```
acgtggtatg ttaatacgac gaacatcgat ggctttagac tggatgccgt caaacatatc      720
aaatatagct ttttccgga ctggctgacg tatgtcagaa accagacggg caaaaacctt       780
tttgccgtcg gcgaattttg gagctatgac gtcaacaaac ttcataacta tatcacgaaa      840
acgaacggca gcatgagcct ttttgatgcc ccgcttcata caaacttttta tacggcgagc    900
aaaagctcag gctattttga tatgagatat ctgctgaaca cacgctgat gaaagatcaa       960
ccgagcctgg cagtcacact ggtcgataac catgatacac aaccgggcca aagccttcaa     1020
agctgggtcg aaccgtggtt taaaccgctg gcgtatgcct ttatcctgac gagacaagaa    1080
gggtatcctt gcgtcttta tggcgactat tatggcatcc gaaatataa tatcccgggc       1140
ctgaaaagca aaatcgatcc gctgctgatc gccagacggg attatgccta tggcacacag     1200
cgggattata tcgaccatca ggacatcatc ggctggacaa gagaaggcat cgatacgaaa    1260
ccgaatagcg gactggcagc actgattaca gatggaccgg gcggaagcaa atggatgtat   1320
gtcggcaaaa acatgccgg caaagtcttt tatgatctga cgggcaacag aagcgatacg      1380
gtcacgatca atgctgatgg ctggggagaa tttaaagtca atggcggcag cgtttcaatc    1440
tgggtcgcca aatga                                                        1455

<210> SEQ ID NO 5
<211> LENGTH: 482
<212> TYPE: PRT
<213> ORGANISM: Bacillus sp.

<400> SEQUENCE: 5

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Thr Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Tyr
```

```
                    225                 230                 235                 240
Ser Phe Phe Pro Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Thr Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 6
<211> LENGTH: 1977
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
aaaattcgga atatttatac aatatcatat gtttcacatt gaaaggggag gagaatcatg    60
aaacaacaaa aacggcttta cgcccgattg ctgacgctgt atttgcgct catcttcttg    120 ctgcctcatt ctgcagcttc agcaaatacg gcgccgatca acgaaacgat gatgcagtat    180
tttgaatggg atctgccgaa tgatggaacg ctgtggacga agtcaaaaa cgaagcggcg    240 aatcttagca gcctgggaat cacagcactt tggcttccgc cggcatataa aggaacgagc    300
caaagcgatg tcggctatgg cgtctatgat ctgtatgacc tgggcgaatt taaccaaaaa    360
ggcacgatcc ggacgaaata tggcacgaaa acacagtata tccaagcgat ccaggcagca    420
aaagcagcag gcatgcaagt ctatgccgac gtcgtcttta atcataaagc gggagcggat    480
ggcacagaat tgtcgatgc cgtcgaagtt gatccgagca acagaaacca agaaacgagc    540
ggcacgtatc aaatccaagc gtggacgaaa tttgattttc cgggcagagg caatacgtat    600
```

-continued

```
agcagcttta atggcgctg gtatcatttt gacggcacgg attgggatga agcagaaaa      660 ctgaaccgga tctataaatt tcggagcacg ggcaaagcat gggattggga agtcgatacg      720
gaaaacggca actatgacta tctgatgttt gccgatctgg atatggatca tccggaagtc      780
gtcacggaac tgaaaaattg gggcacgtgg tatgttaata cgacgaacat cgatggcttt      840
agactggatg ccgtcaaaca tatcaaatat agcttttttc cggactggct gacgtatgtc      900
agaaaccaga cgggcaaaaa ccttttttgcc gtcggcgaat ttggagcta tgacgtcaac      960 aaacttcata actatatcac gaaaacgaac ggcagcatga gccttttttga tgccccgctt     1020 cataacaact tttatacggc gagcaaaagc tcaggctatt ttgatatgag atatctgctg     1080
aacaacacgc tgatgaaaga tcaaccgagc ctggcagtca cactggtcga taaccatgat     1140
acacaaccgg gccaaagcct tcaaagctgg gtcgaaccgt ggtttaaacc gctggcgtat     1200
gcctttatcc tgacgagaca agaagggtat ccttgcgtct tttatggcga ctattatggc     1260
atcccgaaat ataatatccc gggcctgaaa agcaaaatcg atccgctgct gatcgccaga     1320
cgggattatg cctatggcac acagcgggat tatatcgacc atcaggacat catcggctgg     1380
acaagagaag gcatcgatac gaaaccgaat agcggactgg cagcactgat tacagatgga     1440
ccgggcggaa gcaaatggat gtatgtcggc aaaaaacatg ccggcaaagt cttttatgat     1500
ctgacgggca acagaagcga tacggtcacg atcaatgctg atggctgggg agaatttaaa     1560
gtcaatggcg gcagcgtttc aatctgggtc gccaaaacga gcaatgtcac gtttacggtc     1620
aacaatgcca cgacaacgag cggccaaaat gtctatgtcg tcgccaatat cccggaactg     1680
ggcaattgga atacggcgaa cgcaatcaaa atgaacccga gcagctatcc gacatggaaa     1740
gcgacaatcg ctctgccgca aggaaaagcg atcgaattta aatttatcaa aaaagaccag     1800
gcgggcaatg ttatttggga agcacgagc aatagaacgt atacggtccc gtttagcagc     1860
acaggaagct atacagcgag ctggaatgtt ccgtgagtta acagaggacg gatttcctga     1920
aggaaatccg ttttttttatt ttaagcttgg agacaaggta aaggataaaa cctcgag        1977
```

<210> SEQ ID NO 7
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125
```

```
Gln Glu Thr Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```
ctcattctgc agcttcagca aatacggcg                                              29

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctctgttaac tcatttggcg acccagattg aaacg                                       35

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctataaattt acgggcaaag catgggattg g                                           31

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgctttgccc gtaaatttat agatccggtt cag                                         33

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctatgactat ctgctgtttg ccgatctg                                               28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cagatcggca aacagcagat agtcatag                                               28

<210> SEQ ID NO 14
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcatgggatt gggaagtcga tacggaaaac ggcaactatg actatctgct gtttgccg             58

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgtatcgact tcccaatccc atgctttgcc cgtaaattta tagatccggt tc          52

<210> SEQ ID NO 16
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgaaacaac aaaaacggct ttacgcccga ttgctgacgc tgttatttgc gctcatcttc    60
ttgctgcctc attctgcagc ttcagca                                       87

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25

<210> SEQ ID NO 18
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Gln Ala Gly Lys Ser Pro Ala Gly Val Arg Tyr His Gly Gly
1               5                   10                  15

Asp Glu Ile Ile Leu Gln Gly Phe His Trp Asn Val Val Arg Glu Ala
            20                  25                  30

Pro Tyr Asn Trp Tyr Asn Ile Leu Arg Gln Gln Ala Ser Thr Ile Ala
        35                  40                  45

Ala Asp Gly Phe Ser Ala Ile Trp Met Pro Val Pro Trp Arg Asp Phe
    50                  55                  60

Ser Ser Trp Thr Asp Gly Asp Lys Ser Gly Gly Gly Glu Gly Tyr Phe
65                  70                  75                  80

Trp His Asp Phe Asn Lys Asn Gly Arg Tyr Gly Ser Asp Ala Gln Leu
                85                  90                  95

Arg Gln Ala Ala Gly Ala Leu Gly Gly Ala Gly Val Lys Val Leu Tyr
            100                 105                 110

Asp Val Val Pro Asn His Met Asn Arg Phe Tyr Pro Asp Lys Glu Ile
        115                 120                 125

```
Asn Leu Pro Ala Gly Gln Arg Phe Trp Arg Asn Asp Cys Pro Asp Pro
    130                 135                 140

Gly Asn Gly Pro Asn Asp Cys Asp Asp Gly Asp Arg Phe Leu Gly Gly
145                 150                 155                 160

Glu Ala Asp Leu Asn Thr Gly His Pro Gln Ile Tyr Gly Met Phe Arg
                165                 170                 175

Asp Glu Phe Thr Asn Leu Arg Ser Gly Tyr Gly Ala Gly Gly Phe Arg
            180                 185                 190

Phe Asp Phe Val Arg Gly Tyr Ala Pro Glu Arg Val Asp Ser Trp Met
        195                 200                 205

Ser Asp Ser Ala Asp Ser Ser Phe Cys Val Gly Glu Leu Trp Lys Glu
    210                 215                 220

Pro Ser Glu Tyr Pro Pro Trp Asp Trp Arg Asn Thr Ala Ser Trp Gln
225                 230                 235                 240

Gln Ile Ile Lys Asp Trp Ser Asp Arg Ala Lys Cys Pro Val Phe Asp
                245                 250                 255

Phe Ala Leu Lys Glu Arg Met Gln Asn Gly Ser Val Ala Asp Trp Lys
            260                 265                 270

His Gly Leu Asn Gly Asn Pro Asp Pro Arg Trp Arg Glu Val Ala Val
        275                 280                 285

Thr Phe Val Asp Asn His Asp Thr Gly Tyr Ser Pro Gly Gln Asn Gly
    290                 295                 300

Gly Gln His Lys Trp Pro Leu Gln Asp Gly Leu Ile Arg Gln Ala Tyr
305                 310                 315                 320

Ala Tyr Ile Leu Thr Ser Pro Gly Thr Pro Val Val Tyr Trp Pro His
                325                 330                 335

Met Tyr Asp Trp Gly Tyr Gly Asp Phe Ile Arg Gln Leu Ile Gln Val
            340                 345                 350

Arg Arg Thr Ala Gly Val Arg Ala Asp Ser Ala Ile Ser Phe His Ser
        355                 360                 365

Gly Tyr Ser Gly Leu Val Ala Thr Val Ser Gly Ser Gln Gln Thr Leu
    370                 375                 380

Val Val Ala Leu Asn Ser Asp Leu Ala Asn Pro Gly Gln Val Ala Ser
385                 390                 395                 400

Gly Ser Phe Ser Glu Ala Val Asn Ala Ser Asn Gly Gln Val Arg Val
                405                 410                 415

Trp Arg Ser Gly Ser Gly Asp Gly Gly Gly Asn Asp Gly Gly
            420                 425                 430
```

VARIANTS OF *BACILLUS* SP. TS-23 ALPHA-AMYLASE WITH ALTERED PROPERTIES

CROSS-REFERENCE TO RELATED APPLICATIONS

The present application claims priority to U.S. Provisional Patent Application No. 61/026,056, entitled "TS23 Alpha-Amylase Variants With Altered Properties", filed Feb. 4, 2008; and U.S. Provisional Patent Application No. 61/059,403, entitled "TS-23 Alpha-Amylase With Altered Properties", filed Jun. 6, 2008.

SEQUENCE LISTING

Also attached is a sequence listing comprising SEQ ID NOS: 1-18, which are herein incorporated by reference in their entirety.

FIELD OF THE INVENTION

Described herein are variants of a parent alpha-amylase, which variant has alpha-amylase activity and exhibits an alteration in at least one of the following properties relative to said parent alpha-amylase: Substrate specificity, substrate binding, substrate cleavage pattern, thermal stability, pH activity profile, pH stability profile, stability towards oxidation, $Ca^{2+}$ dependency, reduced and increased pI and improved wash performance, specific activity, stability under, e.g., high temperature and/or low pH conditions, in particular at low calcium concentrations. The variants described herein are suitable for starch conversion, ethanol production, laundry wash, dish wash, hard surface cleaning, textile desizing, and/or sweetener production.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or thinning) of solid starch with an α-amylase into dextrins having an average degree of polymerization of about 7-10; and (2) saccharification of the resulting liquefied starch (i.e. starch hydrolysate) with amyloglucosidase (also called glucoamylase or GA). The resulting syrup has a high glucose content. Much of the glucose syrup, which is commercially produced, is subsequently enzymatically isomerized to a dextrose/fructose mixture known as isosyrup.

Alpha-amylases (alpha-1,4-glucan-4-glucanohydrolases, E.C. 3.2.1.1) constitute a group of enzymes, which hydrolyze starch, glycogen, and related polysaccharides by cleaving internal α-1,4-glucosidic bonds at random. This enzyme class has a number of important commercial applications in, for example, starch liquefaction, textile desizing, starch modification in the paper and pulp industry, sweetener (e.g., sugar) manufacture and for brewing. These enzymes can also be used to remove starchy stains during dishwashing and laundry washing. Alpha-amylases are isolated from a wide variety of bacterial, fungal, plant and animal sources. Industrially, many important α-amylases are those isolated from Bacilli.

Amylases can be used commercially in the initial stages (liquefaction) of starch processing; in wet corn milling; in alcohol production; as cleaning agents in detergent matrices; in the textile industry for starch desizing; in baking applications as anti-staling agents; in the beverage industry; in oil-fields in drilling processes; in deinking of recycled paper and in animal feed.

In recent years, attempts have been made to construct alpha-amylase variants having improved properties with respect to specific uses such as starch liquefaction, detergents and textile desizing.

There is a need in the industry for the identification and optimization of amylases, useful for various uses, including dishwashing and laundry washing processes. These second generation amylases will offer improved manufacturing and/or performance characteristics over the industry standard enzymes.

One characterized α-amylase is that of an alkaliphilic *Bacillus* sp. strain TS-23 which produces at least five kinds of enzymes exhibiting starch hydrolyzing activity. (Lin et al., 1998, "Production and properties of a raw-starch-degrading amylase from the thermophilic and alkaliphilic *Bacillus* sp. TS-23," *Biotechnol. Appl. Biochem.* 28: 61-68).

However, there remains a need for a variant of an alpha-amylase, which variant in comparison to the corresponding parent alpha-amylase, i.e., unmutated alpha-amylase, has alpha-amylase activity and exhibits an alteration in at least one of the above mentioned properties relative to said parent alpha-amylase.

SUMMARY

One aspect provided herein is a α-variant amylase, which variant has alpha-amylase activity and exhibits an alteration in at least one of the following properties relative to the parent alpha-amylase: substrate specificity, substrate binding, substrate cleavage pattern, thermal stability, pH activity profile, pH stability profile, stability towards oxidation, $Ca^{2+}$ dependency, specific activity, and stability under, e.g., high temperature and/or low pH conditions, in particular at low calcium concentrations (e.g., less than about 60 ppm, e.g., less than 40 ppm).

One aspect contemplates a variant of a parent *Bacillus* sp. TS-23 alpha-amylase, wherein the variant has 90% identity to SEQ ID NO: 2, and wherein said variant comprises at least two of a), b), or c), as present in SEQ ID NO: 1:
  a) a truncation of the C terminus;
  b) R180 and/or S181 deleted;
  c) M201L;
  d) Q87 to E, R;
  e) N225 to E, R;
  f) N272 to E or R;
  g) N282 to E or R;
  h) T182 delete;
  i) G183 delete;
  j) Q98R, M201L, S243Q, R309A, Q320R, Q359E, and K444E; or
  k) S243Q, A, E, D.

Alternatively, the variant can be one that has an amino acid sequence which has at least about 90% sequence identity to SEQ ID NO: 2, and comprises a ΔRS delete at positions 180-181 of SEQ ID NO: 2 and M201L of SEQ ID NO: 2, and at least one of the following:
  a) Q87 to E, R;
  b) N225 to E, R;

c) N272 to E or R;
d) N282 to E or R;
e) T182 delete;
f) G183 delete;
g) Q98R, M201L, S243Q, R309A, Q320R, Q359E, and K444E; or
h) S243Q, A, E, D.

Additional variants contemplate those with at least about 95%, 98% or 99% sequence identity to SEQ ID NO: 2 and including any of the deletions, substitutions, or additions discussed herein.

The variants further contemplate those variants of those discussed above and herein that have the following characteristics:
  a) requires less than 60 ppm calcium ions for enzymatic activity;
  b) improved oxidative stability relative to the parent *Bacillus* sp. TS-23 alpha-amylase; and/or
  c) improved thermostability relative to the parent *Bacillus* sp. TS-23 alpha-amylase.

Another contemplated variant of those discussed above would comprise a truncation of the carboxy terminus of 1 to 100 amino acid residues or any integer value in between.

Another aspect contemplates the nucleic acids that encode the above variants. Such as an isolated nucleic acid encoding a variant of a parent *Bacillus* sp. TS-23 alpha-amylase, wherein said variant comprises at least a), b), or c):
  a) a truncation of the C terminus;
  b) R180 and/or S181 deleted;
  c) M201L;
  d) Q87 to E, R;
  e) N225 to E, R;
  f) N272 to E or R;
  g) N282 to E or R;
  h) T182 delete;
  i) G183 delete;
  j) Q98R, M201L, S243Q, R309A, Q320R, Q359E, and K444E;
  k) S243Q, A, E, D;
corresponding to SEQ ID NO: 1 and having at least about 90% sequence identity to SEQ ID NO: 1, and wherein said variant exhibits alpha-amylase activity.

Also contemplated are vectors comprising the aforementioned nucleic acids as well as isolated host cells comprising the nucleic acids. Also contemplated are isolated host cells comprising the vector that comprises the nucleic acids encoding any of the aforementioned variants. Such an isolated host cell includes a prokaryote or an eukaryote (e.g., a bacterium or a fungus). For examples, the bacterium can be a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans*, and *S. murinus*; or a Gram negative bacterium, wherein said Gram negative bacterium is *Escherichia coli* and a *Pseudomonas* sp.

Also contemplated herein is a detergent additive comprising one of the aforementioned variants. The contemplated detergent additives can further comprise one or more enzymes from the group consisting of: a cellulase, a protease, an aminopeptidase, an amylase, a carbohydrase, a carboxypeptidase, a catalase, a chitinase, a cutinase, a cyclodextrin glucanotransferase, a deoxyribonuclease, an esterase, an α-galactosidase, a β-galactosidase, a glucoamylase, α-glucosidase, a β-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, a pullulanase, an isoamylase, a carrageenase, or any combination thereof. The detergent additive can be in the form of a non-dusting granulate, microgranulate, stabilized liquid, or protected enzyme.

Also contemplated herein is a detergent composition comprising any of the afore mentioned detergent additives. A detergent composition also contemplates a surfactant and a variant as discussed herein. The detergent composition can be a laundry detergent or dish detergent. Contemplated detergent compositions can further comprise one or more enzymes selected from the group consisting of a cellulase, a protease, an aminopeptidase, an amylase, a carbohydrase, a carboxypeptidase, a catalase, a chitinase, a cutinase, a cyclodextrin glucanotransferase, a deoxyribonuclease, an esterase, an α-galactosidase, a β-galactosidase, a glucoamylase, an α-glucosidase, a β-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, a pullulanase, an isoamylase, a carrageenase, and any combination thereof. In the alternative or in addition, the detergent composition can further comprise one or more of a surfactant, detergent builder, complexing agent, polymer, bleaching system, stabilizer, foam booster, suds suppressor, anti-corrosion agent, soil-suspending agent, anti-soil redeposition agent, dye, bactericide, hydrotope, optical brightener, fabric conditioner, and perfume.

Another aspect contemplated is a biofilm hydrolyzing composition comprising any of the variants discussed above or herein in a solution or gel, and optionally further comprising a cellulase, a hemicellulase, a xylanase, a lipase, a protease, a pectinase, an antimicrobial agent, or any combination thereof. These biofilm hydrolyzing compositions can be used in a method of hydrolyzing a biofilm comprising administering the composition of claim 24 for a period sufficient to process said biofilm.

Another contemplated aspect is a baking composition comprising any of the above mentioned variants or those disclosed herein in a solution or gel. Another aspect contemplates a method of baking, comprising administering a baking composition with a variant disclosed herein.

In yet a further aspect, a composition for liquefying starch is contemplated comprising a variant discussed above or herein, wherein said composition is in solution. The composition can than be utilized in a method of liquefying starch comprising administering the composition of to a liquefied starch for a time sufficient to liquefy said starch. The composition can be added to the liquefied starch solution for example at about 40-60 μg/g dry solids. A preferred starch for liquefaction is cornstarch, which can be in the form of a liquefied starch solution. Liquefaction can occur at a temperature of about 85° C. to about 100° C. In the alternative or in addition, the liquefied starch solution is liquefied at about pH 5.0 to about pH 6.5. The method can be further carried out to comprise a fermenting step, wherein the liquefact is fermented to product ethanol. One aspect contemplates that the fermenting step produces at least about 2.5% v/v ethanol. In one aspect, the liquefaction and fermenting steps are conducted contemporaneously in the same reaction vessel. In another aspect, the fermenting step does not require a glucoamylase-catalyzed reaction. The liquefaction step can have calcium is present in an amount less than about 60 ppm.

Another aspect contemplates a composition for saccharifying starch comprising a variant discussed above or herein in a solution. Further contemplated is a method of saccharifying starch comprising administering a saccharifying composition for a time sufficient to saccharify said starch. This can be done in a solution wherein there is less than about 60 ppm calcium is present.

A further embodiment contemplates a textile desizing composition comprising a variant described above or herein in an aqueous solution, and optionally comprising another enzyme. Also contemplated is a method of desizing a textile comprising administering said desizing composition for a time sufficient to desize the textile. Calcium can be present in the desizing solution in an amount less than about 60 ppm.

A further aspect contemplates a starch processing composition comprising the a variant described above or herein. The starch processing composition can further comprise a glucoamylase, an isoamylase, a pullulanase, phytase, or any combination thereof. Also contemplated is a method of processing the starch comprising administering the starch processing composition for a time sufficient to process said starch. This can be done in the presence of less than about 60 ppm calcium.

BRIEF DESCRIPTION OF THE DRAWINGS

The accompanying drawings are incorporated in and constitute a part of this specification, illustrate embodiments. In the drawings:

FIG. 1. Polypeptide sequence of alpha-amylase from *Bacillus* sp. TS-23, full-length, mature chain (SEQ ID NO: 1).

FIG. 2. Truncated polypeptide sequence of alpha-amylase from *Bacillus* sp. TS-23, mature chain (SEQ ID NO: 2). The bold and underlined residues indicate the amino acids present at R180, S181 and M201 of SEQ ID NO: 2.

FIG. 3. Optimized nucleic acid sequence for the *Bacillus* sp. TS-23 alpha-amylase gene (SEQ ID NO: 3)(AmyTS23).

FIG. 4. Nucleic acid sequence encoding the truncated alpha-amylase of *Bacillus* sp. TS-23 (AmyTS23t) (SEQ ID NO: 3) that has been optimized (SEQ ID NO: 4) (AmyTS23t).

FIG. 5. This figure depicts an expression cassette made for AmyTS23 and AmyTS23t.

FIG. 10. Depicts an accelerated stability study with AmyTS23t alpha-amylase and AmyTS23t-RSdelete (SEQ ID NO: 5) in MOPS buffer and in a commercial laundry detergent. Enzyme samples were incubated at 37° C. in either MOPS buffer or commercial detergent I and the remaining activity was determined over time in a Megazyme assay.

FIG. 11. Depicts the RS deleted truncated *Bacillus* sp. TS-23 alpha amylase of SEQ ID NO: 5).

FIG. 18. Depicts a DNA (Panel A) (SEQ ID NO: 6) and amino acid sequence (Panel B) (SEQ ID NO: 7) of a synthetic *Bacillus* sp. TS-23 alpha-amylase.

DETAILED DESCRIPTION

Figure 6:
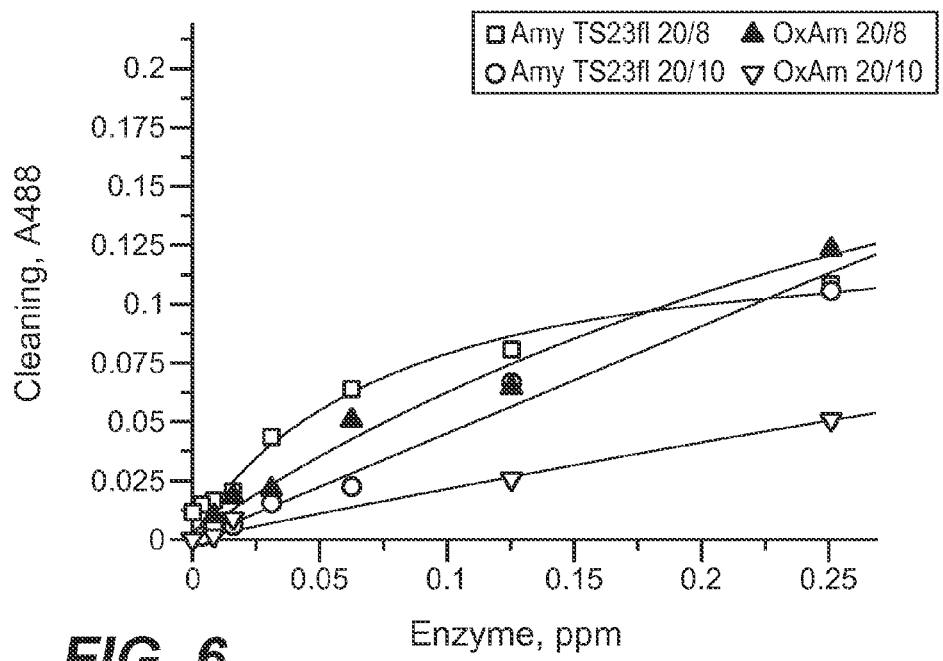
FIG. 6. Depicts results from a swatch cleaning assay using AmyTS23 amylase mature full-length (amy TS23Fl) and OxAm control (Danisco US Inc., Genencor Division). Swatch was incubated in either 25 mM HEPES pH 8 or 25 mM CAPS pH 10.3 buffer; enzymes were added at the indicated level. The reaction was incubated 20° C. for 60 minutes with shaking at 750 rpm in an Eppendorf Thermomix controlled temperature block. The data indicates that amy TS23Fl performs equal to or better than the OxAm control at both pH values. The X-axis is in parts per million (ppm), and the Y axis represents an absorbance reading of the supernatant from the microswatch cleaning assay measured at a wavelength of 488 nm.

The following relates to compounds, compositions, methods of making said compounds, and methods of using said compounds and compositions, wherein the compounds are a *Bacillus* sp. no. TS-23 α-amylase or variants thereof. The *Bacillus* sp. no. TS-23 α-amylases, as well as variants thereof, were sought that have high performance in, for example, laundry and dishwashing tests. They can be used for other purposes as contemplated herein.

The α-amylase of *Bacillus* sp. no. TS-23 has a pH optimum of 9 and is stable over a broad pH range (i.e., pH 4.7 to 10.8). The polypeptide had a temperature optimum of 45° C. The enzyme has activity at lower temperatures, e.g., 15-20° C.

In some aspects, the compounds, compositions and methods described herein rely on routine techniques and methods used in the field of genetic engineering and molecular biology. The following resources include descriptions of general methodology useful in practicing the methods with the materials disclosed herein: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). These general references provide definitions and methods known to those in the art. However, the embodiments discussed herein should not be limited to any particular methods, protocols, and reagents described, as these may vary.

Unless defined otherwise herein, all technical and scientific terms used herein have the same meaning as commonly understood by one of ordinary skill in the art. See e.g., Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, N.Y. (1991) provide one of skill with genera dictionaries of many of the terms used herein.

Although any methods and materials similar or equivalent to those described herein can be used in the practice or testing of the compounds, compositions and methods of use disclosed herein, the preferred methods and materials are described.

Exemplary embodiments will now be described in detail by way of reference only using the following definitions and examples. All patents and publications, including all sequences disclosed within such patents and publications, referred to herein are expressly incorporated by reference.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments disclosed, which can be had by reference to the specification as a whole.

1. Definitions & Abbreviations

In accordance with this detailed description, the following abbreviations and definitions apply. It should be noted that as used herein, the singular forms "a," "an," and "the" include plural referents unless the context clearly dictates otherwise. Thus, for example, reference to "a polypeptide" includes a plurality of such polypeptides and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1. Definitions

As used herein, the term "starch" refers to any material comprised of the complex polysaccharide carbohydrates of plants, comprised of amylose and amylopectin with the formula $(C_6H_{10}O_5)_x$, wherein "X" can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

"Amylase" is meant to include any amylase, such as glucoamylases, α-amylases, β-amylases and wild-type α-amylases of bacteria such as *Bacillus* sp., such as *B. licheniformis* and *B. subtilis*. "Amylase" shall mean an enzyme that is, among other things, capable of catalyzing the degradation of starch. Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) β-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-Amylases, α-glucosidases (EC 3.2.1.20; α-D-glucoside glucohydrolase), glucoamylases (EC 3.2.1.3; α-D-(1→4)-glucan glucohydrolase), and product-specific amylases can produce malto-oligosaccharides of a specific length from starch.

"*Bacillus* sp. strain TS-23 α-amylase" is an α-amylase derived from *Bacillus* sp. strain TS-23. The gene encoding the α-amylase can be the wild-type gene or a codon optimized polynucleotide that encodes the α-amylase. By "*Bacillus* sp. strain TS-23 α-amylase variants" is meant a variant of the wild-type *Bacillus* sp. strain TS-23 α-amylase, which includes a sequence substitution, addition or deletion from the parent polypeptide sequence of *Bacillus* sp. strain TS-23. The full length, mature α-amylase of *Bacillus* sp. strain TS-23 is (amino to carboxy orientation) (SEQ ID NO: 1) and is depicted in FIG. 1.

As used herein, "parent enzyme" and "parent polypeptide" shall mean the polypeptide of *Bacillus* sp. strain TS-23. By "parent nucleic acid" is meant a nucleic acid sequence encoding said parent polypeptide. The *Bacillus* sp. strain TS-23 α-amylase can further include mutations in the signal sequence of the parent polypeptide, or elsewhere in the α-amylase parent polypeptide. Thus, the *Bacillus* sp. strain TS-23 α-amylase can be in the form of a fusion protein containing a heterologous α-amylase polypeptide. It can also include chimeras (i.e., the combination of at least two α-amylases). For example, the *Bacillus* sp. strain TS-23 α-amylase can comprise the signal peptide from another α-amylase, such as *B. licheniformis* (LAT), which is well know in the art.

By "truncated TS-23 α-amylase variant" is meant a TS-23 amino acid sequence that is truncated by removal of one or more amino acids from the carboxy end of the full-length mature (wild-type) polypeptide sequence. The truncation may be at least 99 amino acids.

By "truncated TS-23 α-amylase RS delete variant" is meant a truncated TS-23 α-amylase variant, wherein the amino acids at positions R180 and S181 have been deleted.

The term "variant" is used interchangeably with the term "mutant". Variants shall include polypeptides, as well as the nucleic acids that encode additional substitutions, transversions, insertions, and deletions to the Bacillus sp. strain TS-23 α-amylase, i.e. the parent alpha-amylase. Variants can include sequences that are complementary to sequences that are capable of hybridizing to the nucleotide sequences presented herein. For example, a variant nucleic acid sequence is complementary to sequences capable of hybridizing under stringent conditions (e.g., 50° C. and 0.2×SSC {1×SSC=0.15 M NaCl, 0.015 M $Na_3$ citrate, pH 7.0}) to the nucleotide sequences presented herein. The term variant nucleic acid sequence encompasses sequences that are complementary to sequences that are capable of hybridizing under high stringent conditions (e.g., 65° C. and 0.1×SSC {1×SSC=0.15 M NaCl, 0.015 M $Na_3$ citrate, pH 7.0}) to the nucleotide sequences presented herein.

The alpha-amylase variant polypeptides described herein can also have mutations that extend half-life relative to the parent enzyme by at least about 10%, 20%, 30%, 40%, 50%, 60%, 70%, 80%, 90%, 100%, 200% or more, particularly at elevated temperatures of at least about 55° C. to about 95° C. or more, particularly at about 80° C.

The alpha-amylase variants may have exo-specificity, measured by exo-specificity indices described herein, for example. Alpha-amylase variants include those having higher or increased exo-specificity compared to the parent enzymes or polypeptides from which they were derived, typically when measured under identical conditions. Thus, for example, the alpha-amylase variant polypeptides may have an exo-specificity index of at least about 10%, 20%, 30%, 40%, 50%, 60%, 70%, 80%, 90%, 100%, 150%, 200%, 500%, 1000%, 5000%, 10,000% or higher compared to their parent polypeptides.

In another aspect, the alpha-amylase variant polypeptide encoded by the nucleic acid has the same pH stability as the parental sequence. In another aspect, the variant comprises a mutation that confers a greater pH stability range or shifts the pH range to a desired area for the end commercial purpose of the enzyme. For example, in one embodiment, the variant can degrade starch at about pH 5.0 to about pH 10.5. The alpha-amylase variant polypeptide may have a longer half-life or higher activity (depending on the assay) compared to the parent polypeptide under identical conditions, or the alpha-amylase variant may have the same activity as the parent polypeptide. The alpha-amylase variant polypeptide also may have about 10%, 20%, 30%, 40%, 50%, 60%, 70%, 80%, 90%, 100%, 200% or longer half-life compared to their parent polypeptide under identical pH conditions. Alternatively, or in addition, the enzyme variant may have higher specific activity compared to the parent polypeptide under identical pH conditions.

In another aspect, a nucleic acid complementary to a nucleic acid encoding any of the alpha-amylase variants set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in host organisms of bacterial, especially those for industrial culturing.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "recovered", "isolated", and "separated" as used herein refer to a compound, protein, cell, nucleic acid or amino acid that is removed from at least one component with which it is naturally associated and found in nature.

By "purified" is meant that the material is in a relatively pure state, e.g., at least about 90% pure, or at least about 95% pure, or at least about 98% pure.

By "thermostable" is meant the ability of the enzyme to retain activity after exposure to elevated temperatures. The thermostability of an enzyme, such as an α-amylase enzymes, is measured by its half-life. The half-life ($t_{1/2}$) is the time in minutes, hours, or days, during which half the enzyme activity is lost under defined conditions. The half-life value is calculated by measuring the residual α-amylase activity.

By "melting temperature" is meant the temperature at which 50% of the polypeptide sample is completely denatured.

By "pH range" is meant the ability of the enzyme to exhibit catalytic activity from acidic to basic conditions spanning about 5 or more pH units.

As used herein, "pH stable" relates to the ability of the enzyme to retain activity over a wide range of pHs for a predetermined period of time (e.g., 15 min., 30 min., 1 hour).

By "recombinant", when used in reference to a cell, nucleic acid, protein, or vector, is meant that the cell, nucleic acid, protein or vector has been modified by the introduction of a heterologous nucleic acid or protein, or the alternation of a native nucleic acid or protein, or that the cell is derived from a cell so modified. Thus, for example, recombinant cells express nucleic acid sequences that are not found within native (non-recombinant) forms of the cell or express native genes that are otherwise abnormally expressed (e.g. underexpressed or not expressed at all).

As used herein, "amino acid sequence" is synonymous with the term "polypeptide" and/or the term "protein" and are used interchangeably herein. In some instances, the term "amino acid sequence" is synonymous with the term "peptide". In some instances, the term "amino acid sequence" is synonymous with the term "enzyme". The conventional one-letter or three-letter code for amino acid residues are used herein.

The term "nucleic acid" encompasses DNA, RNA, single stranded or double stranded and chemical modifications thereof. The terms "nucleic acid" and "polynucleotide" may be used interchangeably herein.

As used herein, "nucleotide sequence" or "nucleic acid sequence" refers to an oligonucleotide sequence or polynucleotide sequence encoding a Bacillus sp. strain TS-23 α-amylase polypeptide or variant thereof, and fragments and derivatives thereof (such as portions thereof). The nucleotide sequence may be of genomic, synthetic, or recombinant origin, and may be double-stranded or single-stranded whether representing the sense or anti-sense strand. As used herein, the term nucleotide sequence includes genomic DNA, cDNA, synthetic DNA, and RNA. For example, the DNA can be a cDNA sequence coding for a Bacillus sp. strain TS-23 α-amylase or variant thereof. Because the genetic code is degenerate, more than one codon may be used to encode a particular amino acid, and the described materials encompasses nucleotide sequences which encode a particular amino acid sequence.

By "homologue" shall mean an entity having a certain degree of identity with the subject amino acid sequences and the subject nucleotide sequences. A homologous sequence is taken to include an amino acid sequence at least about 75%, 80%, 85% or 90% identical, or at least about 95%, 96%, 97%, 98% or 99% identical to the subject sequence. Typically, homologues will comprise the same active sites as the subject amino acid sequence. A polynucleotide or a polypeptide having a certain percent (e.g., at least about 80%, 85%, 90%, 95%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Such programs may include the GCG Pileup program, FASTA (Pearson et al. (1988) *Proc. Nat'l Acad. Sci. USA* 85:2444-2448), and BLAST (BLAST Manual, Altschul et al., Nat'l Cent. Biotechnol. Inf., Nat'l Lib. Med. (NCIB NLM NIH), Bethesda, Md., and Altschul et al., (1997) *NAR* 25:3389-3402). Another alignment program is ALIGN Plus (Scientific and Educational Software, PA), using default parameters. Another sequence software program that finds use is the TFASTA Data Searching Program available in the Sequence Software Package Version 6.0 (Genetics Computer Group, University of Wisconsin, Madison, Wis.).

As used herein, "hybridization" shall include the process by which a strand of nucleic acid joins with a complementary strand through base pairing, as well as the process of amplification as carried out in polymerase chain reaction (PCR) technologies. The α-amylase or variant thereof nucleic acid may exist as single- or double-stranded DNA or RNA, an RNA/DNA heteroduplex or an RNA/DNA copolymer. One skilled in the art will recognize that sequences encompassed by the disclosure are also defined by the ability to hybridize under stringent hybridization conditions with the exemplified amyS sequence (e.g., SEQ ID NO: 5 of WO 06/002643) or the *Bacillus* sp. TS-23 mature, full-length alpha-amylase. A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (see, e.g., Sambrook (1989) supra, particularly chapters 9 and 11). In some embodiments, stringent conditions correspond to a $T_m$ of 65° C. and 0.1×SSC, 0.1% SDS.

As used herein, "synthetic" shall refer to that which is produced by in vitro chemical or enzymatic synthesis. It includes, but is not limited to, nucleic acids encoding *Bacillus* sp. strain TS-23 α-amylase or variants thereof made with optimal codon usage for host organisms, such as the methylotrophic yeasts (e.g., *Pichia, Hansenula*, etc) or filamentous fungi (e.g., *Trichoderma* (e.g., *T. reesei*), etc) or other expression hosts (e.g., *Bacillus, Streptomyces*, etc).

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, "transformed cell" shall include cells that have been genetically altered by use of recombinant DNA techniques. Transformation typically occurs by insertion of one or more nucleotide sequences into a cell. The inserted nucleotide sequence may be a heterologous nucleotide sequence (i.e. is a sequence that is not natural to the cell that is to be transformed, such as a DNA sequence encoding a fusion protein or a non-native sequence).

"Host strain" or "host cell" means a suitable host for an expression vector or DNA construct comprising a polynucleotide encoding a variant α-amylase enzyme according to the present disclosure. Specifically, host strains are preferably bacterial cells. In a preferred embodiment, "host cell" means both the cells and protoplasts created from the cells of a microbial strain, and particularly a *Bacillus* sp.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

The term "culturing" refers to growing a population of microbial cells under suitable conditions in a liquid or solid medium. In one embodiment, culturing refers to fermentative bioconversion of a starch substrate containing granular starch to an end-product (typically in a vessel or reactor).

"Fermentation" is the enzymatic and anaerobic breakdown of organic substances by microorganisms to produce simpler organic compounds. While fermentation occurs under anaerobic conditions, it is not intended that the term be solely limited to strict anaerobic conditions, as fermentation also occurs in the presence of oxygen.

A "gene" refers to a DNA segment that is involved in producing a polypeptide and includes regions preceding and following the coding regions as well as intervening sequences (introns) between individual coding segments (exons).

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. A preferred promoter used herein is *Bacillus licheniformis* alpha-amylase (AmyL).

The term "operably linked" refers to juxtaposition wherein the elements are in an arrangement allowing them to be functionally related. Thus, as used herein, "operably linked" means that the components described are in a relationship permitting them to function in their intended manner. For example, a regulatory sequence operably linked to a coding sequence is ligated in such a way that expression of the coding sequence is achieved under conditions compatible with the control sequences.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

A "signal sequence" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

As used herein, "biologically active" shall refer to a sequence having a similar structural function (but not necessarily to the same degree), and/or similar regulatory function (but not necessarily to the same degree) and/or similar biochemical function (but not necessarily to the same degree) of the naturally occurring sequence.

As used herein the term "saccharification" refers to enzymatic conversion of starch to glucose.

The term "gelatinization" means solubilization of a starch molecule by cooking to form a viscous suspension.

The term "liquefaction" refers to the stage in starch conversion in which gelatinized starch is hydrolyzed to give low molecular weight soluble dextrins.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

The terms "end-product" or "desired end-product" refer to any carbon-source derived molecule product which is enzymatically converted from the starch substrate.

As used herein the term "dry solids content (ds)" refers to the total solids of a slurry in % on a dry weight basis. The term "slurry" refers to an aqueous mixture containing insoluble solids.

The term "residual starch" refers to the remaining starch (soluble or insoluble) left in a composition after fermentation or enzymatic hydrolysis of a starch containing substrate.

As used herein "a recycling step" refers to the recycling of mash components, which may include residual starch, enzymes and/or microorganisms to ferment substrates comprising starch.

The term "mash" refers to a mixture of a fermentable carbon source (carbohydrate) in water used to produce a fermented product, such as an alcohol. In some embodiments, the term "beer" and "mash" are used interchangeability.

The term "stillage" means a mixture of non-fermented solids and water, which is the residue after removal of alcohol from a fermented mash.

The terms "distillers dried grain (DDG)" and "distillers dried grain with solubles (DDGS)" refer to a useful by-product of grain fermentation.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Sacchromyces*, particularly, *S. cerevisiae*.

As used herein when describing proteins and genes that encode them, the term for the gene is italicized, (e.g., the gene that encodes amyL (*B. licheniformis* α-amylase) may be denoted as amyL). The term for the protein is generally not italicized and the first letter is generally capitalized, (e.g., the protein encoded by the amyL gene may be denoted as AmyL or amyL). Similarly, the amylase gene and protein from *Bacillus* sp. strain TS-23 provided for herein are amyTS23 and AmyTS23, respectively.

The term "contacting" refers to the placing of the respective enzyme(s) in sufficiently close proximity to the respective substrate to enable the enzyme(s) to convert the substrate to the end-product. Those skilled in the art will recognize that mixing solutions of the enzyme with the respective substrates can effect contacting.

The term "derived" encompasses the terms "originated from", "obtained" or "obtainable from", and "isolated from".

The term "enzymatic conversion" in general refers to the modification of a substrate by enzyme action. The term as used herein also refers to the modification of a starch substrate by the action of an enzyme.

The term "heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes, and/or synthetic genes.

The term "endogenous" with reference to a polynucleotide or protein refers to a polynucleotide or protein that occurs naturally in the host cell.

As used herein, the term "expression" refers to the process by which a polypeptide is produced based on the nucleic acid sequence of a gene. The process includes both transcription and translation.

As used herein the term "specific activity" means an enzyme unit defined as the number of moles of substrate converted to product by an enzyme preparation per unit time under specific conditions. Specific activity is expressed as units (U)/mg of protein.

The term "yield" refers to the amount of end-product or desired end-products produced using the methods described herein. In some preferred embodiments, the yield is greater than that produced using methods known in the art. In some embodiments, the term refers to the volume of the end product and in other embodiment the term refers to the concentration of the end product.

"ATCC" refers to American Type Culture Collection located at Manassas, Va. 20108 (ATCC).

"NRRL" refers to the Agricultural Research Service Culture Collection, National Center for Agricultural Utilization Research (and previously known as USDA Northern Regional Research Laboratory), Peoria, Ill.

As used herein the term "comprising" and its cognates are used in their inclusive sense; that is, equivalent to the term "including" and its corresponding cognates.

As used herein, "food" includes both prepared food, as well as an ingredient for a food, such as flour. As used herein, "food ingredient" includes a formulation that is or can be added to a functional food or foodstuff and includes formulations used at low levels in a wide variety of products that require, for example, acidifying or emulsifying. The food ingredient may be in the form of a solution or as a solid, depending on the use and/or the mode of application and/or the mode of administration.

As used herein, "functional food" means food capable of providing not only a nutritional effect and/or a taste satisfaction, but also any further beneficial effect to the consumer.

1.2. Abbreviations

The following abbreviations apply unless indicated otherwise:

| | |
|---|---|
| AAPF | alanine-alanine-proline-phenylalanine |
| ADW | autodish washing |
| AE | alcohol ethoxylate |
| AEO | alcohol ethoxylate |
| AEOS | alcohol ethoxysulfate |
| AES | alcohol ethoxysulfate |
| AFAU | acid fungal alpha-amylase units |
| AGU | glucoamylase activity unit |
| AOS | α-olefinsulfonate |
| AS | alcohol sulfate |
| BAA | *Bacillus amyloliquefaciens* α-amylase |
| BLA | *Bacillus licheniformis* (or LAT) |
| BSA | bovine serum albumin |
| cDNA | complementary DNA |
| CMC | carboxymethylcellulose |
| DE | Dextrose Equivalent |
| DNA | deoxyribonucleic acid |
| DP3 | degree of polymerization with three subunits |
| DPn | degree of polymerization with n subunits |
| DS | dry solid |
| DSC | differential scanning calorimetry |
| DTMPA | diethyltriaminepentaacetic acid |
| EC | enzyme commission for enzyme classification |
| EDTA | ethylenediaminetetraacetic acid |
| EDTMPA | ethylenediaminetetramethylene phosphonic acid |
| EO | ethylene oxide |
| F&HC | fabric and household care |
| FAU | fungal amylase unit |
| GA | glucoamylase |
| gpg | grains per gallon |
| HDG | heavy duty granular laundry |
| HDL | heavy duty liquid laundry |
| HFCS | high fructose corn syrup |
| HFSS | high fructose starch based syrup |
| HPAEC-PAD | high performance anion exchange chromatography with pulsed amperometric detection |
| IPTG | isopropyl β-D-thiogalactoside |
| LAS | linear alkylbenezenesulfonate |
| LOM | Launder-O-meter |
| LU | Lipase Units |
| MTP | microtiter plate |
| MES | 2-(N-morpholino)ethanesulfonic acid |
| MW | molecular weight |
| NA | North American |
| nm | nanometer |
| NOBS | nonanoyloxybenzenesulfonate |
| NTA | nitrilotriacetic acid |
| PAA | paracetic acid |
| PCR | polymerase chain reaction |
| PEG | polyethyleneglycol |
| pI | isoelectric point |
| PI | performance index |
| ppm | parts per million |
| PVA | poly(vinyl alcohol) |
| PVP | poly(vinylpyrrolidone) |
| RAU | Reference Amylase Units |
| RMS | root mean square |
| RNA | ribonucleic acid |
| rpm | revolutions per minute |
| SAS | secondary alkane sulfonates |
| 1X SSC | 0.15 M NaCl, 0.015 M sodium citrate, pH 7.0 |

-continued

| | |
|---|---|
| SSF | simultaneous saccharification and fermentation |
| TAED | tetraacetylethylenediamine |
| TCA | tricholoracetic acid |
| TNBS | trinitrobenzenesulfonic acid |
| TSB | tryptic soy broth |
| UFC | ultrafiltration concentrate |
| WE | Western Europe |
| w/v | weight/volume |
| w/w | weight/weight |
| wt | wild-type |
| μL | microliter |

1.3 Nomenclature

In the present description and claims, the conventional one-letter and three-letter codes for amino acid residues are used. For ease of reference, alpha-amylase variants are described by using the following nomenclature:

Original amino acid(s): position(s): substituted amino acid(s)

According to this nomenclature, for instance the substitution of serine by an alanine in position 242 is shown as:
Ser242Ala or S242A
a deletion of alanine in position 30 is shown as:
Ala30* or A30* or ΔA30
and insertion of an additional amino acid residue, such as lysine, is shown as:
Ala30AlaLys or A30AK.

A deletion of a consecutive stretch of amino acid residues, such as amino acid residues 30-33, is indicated as (30-33)* or Δ(A30-N33) or Δ30-33. A deletion of two consecutive amino acids, such as amino acid residues R180-S181, is indicated as ΔRS or Δ180-181.

Where a specific alpha-amylase contains a "deletion" in comparison with other alpha-amylases and an insertion is made in such a position, this is indicated as:
*36Asp or *36D
for insertion of an aspartic acid in position 36.

Multiple mutations are separated by plus signs, i.e.:
Ala30Asp+Glu34Ser or A30N+E34S
representing mutations in positions 30 and 34 substituting alanine and glutamic acid for asparagine and serine, respectively.

When one or more alternative amino acid residues may be inserted in a given position it is indicated as:
A30N, E; or
A30N or A30E.

Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:

R, N, D, A, C, Q, E, G, H, I, L, K, M, F, P, S, T, W, Y, V.

Further, "A30X" means any one of the following substitutions:
A30R, A30N, A30D, A30C, A30Q, A30E, A30G, A30H, A30I, A30L, A30K, A30M, A30F, A30P, A30S, A30T, A30W, A30Y, or A30V;

or in short: A30R, N, D, C, Q, E, G, H, I, L, K, M, F, P, S, T, W, Y, V.

If the parent enzyme—used for the numbering—already has the amino acid residue in question suggested for substitution in that position the following nomenclature is used: "X30N" or "X30N,V" in the case where for instance one of N or V is present in the wildtype. Thus, it means that other corresponding parent enzymes are substituted to an "Asn" or "Val" in position 30.

1.4 Characteristics of Amino Acid Residues

```
Charged amino acids:
Asp, Glu, Arg, Lys, His

Negatively charged amino acids
(with the most negative residue first):
Asp, Glu

Positively charged amino acids
(with the most positive residue first):
Arg, Lys, His Neutral amino acids:
Gly, Ala, Val, Leu, Ile, Phe, Tyr, Trp, Met, Cys,
Asn, Gln, Ser, Thr, Pro Hydrophobic amino acid residues
(with the most hydrophobic residue listed last):
Gly, Ala, Val, Pro, Met, Leu, Ile, Tyr, Phe, Trp, Hydrophilic amino acids
(with the most hydrophilic residue listed last):
Thr, Ser, Cys, His, Glu, Gln, Asn, Asp, Lys, Arg
```

1.5 Homology (Identity)

A polynucleotide or a polypeptide having a certain percent (e.g., at least about 80%, 83%, 85%, 90%, 95%, 96%, 97%, 98%, or 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the Vector NTI Advance™ 9.0 (Invitrogen Corp. Carlsbad, Calif.), GCG Pileup program, FASTA (Pearson et al. (1988) *Proc. Nat'l Acad. Sci. USA* 85:2444-2448), and BLAST (BLAST Manual, Altschul et al., Nat'l Cent. Biotechnol. Inf., Nat'l Lib. Med. (NCIB NLM NIH), Bethesda, Md., and Altschul et al., (1997) *Nuc. Acids Res.* 25: 3389-3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

The homology may be determined as the degree of identity between the two sequences indicating a derivation of the first sequence from the second. The homology may suitably be determined by means of computer programs known in the art such as GAP provided in the GCG program package (described above). Thus, Gap GCG v8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, *J. Mol. Biol.* 48: 443-453 (1970), to make alignments and to calculate the identity.

A structural alignment between AmyTS23 (SEQ ID NO: 1) and, e.g., another alpha-amylase may be used to identify equivalent/corresponding positions in other alpha-amylases having a high degree of homology, e.g., about 80%, 85%, 90%, 95%, 97% or 99%, with AmyTS23. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., *FEBS Lett.* 224: 149-155, 1987) and reverse threading (T. Huber and A. E. Torda, *Protein Sci.* 7(1): 142-149 (1998).

1.6 Hybridization

The oligonucleotide probe used in the characterization of AmyTS23, above, may suitably be prepared on the basis of the full or partial nucleotide or amino acid sequence of the alpha-amylase in question.

Suitable conditions for testing hybridization involve pre-soaking in 5×SSC and prehybridizing for 1 hour at 40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridization method can be found in Sambrook et al., MOLECULAR CLONING: A LABORATORY MANUAL, 2nd ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

One skilled in the art will recognize that the described sequences can also be defined by the ability to hybridize under stringent hybridization conditions with the exemplified amyTS23 sequence (e.g., SEQ ID NO: 4 shown in FIG. 4). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (see, e.g., Sambrook (1989) supra, particularly chapters 9 and 11). In some embodiments, stringent conditions correspond to a $T_m$ of 65° C. and 0.1×SSC, 0.1% SDS.

1.7 Parent Alpha-Amylases

According to the present disclosure any AmyTS23 alpha-amylase, as defined above, may be used as the parent (i.e., backbone) alpha-amylase. In a preferred embodiment the parent alpha-amylase is derived from *Bacillus* sp. strain TS-23, e.g., one of those referred to above, such as the TS-23 alpha-amylase having the amino acid sequence shown in SEQ ID NO: 1 (see FIG. 1).

1.8 Altered Properties

The following section describes the relationship between mutations, which are present in a variant described herein, and desirable alterations in properties (relative to those of a parent TS-23 alpha-amylase), which may result therefrom.

As mentioned above, one aspect relates to an alpha-amylase derivable from *Bacillus* sp. TS-23 and mutants thereof with altered properties.

Parent TS-23 alpha-amylases specifically contemplated in connection with the specifically contemplated altered properties are the above mentioned parent TS-23 alpha-amylase and parent hybrid alpha-amylases which comprise at least a portion of a TS-23 alpha-amylase. The *Bacillus* sp strain TS-23 alpha-amylase (SEQ ID NO: 1) is used as the starting point, but corresponding positions in other *Bacillus* alpha-amylases having a high degree of homology should be understood as disclosed and specifically contemplated too.

Another embodiment relates to a variant with altered properties as mentioned above.

In the first aspect, a variant of a parent *Bacillus* sp. strain alpha-amylase, comprising at least two of the following alterations:

(a) truncation of the C-terminus (e.g., from one to 100 amino acids removed and any integer value in between), (b) substitution of amino acid 201 (i.e., M201), using SEQ ID NO: 1 for numbering, or (c) deletion of at least two residues selected from the group consisting of R180, S181, T182 and G183, using SEQ ID NO: 1 for numbering, and wherein the variant has alpha-amylase activity.

1.8.1 Stability

In the context of the variants described herein, mutations (including amino acid substitutions and deletion) of importance with respect to achieving altered stability (i.e., higher or lower), in particular improved stability, at especially high temperatures (i.e., 70-120° C.) and/or extreme pH (i.e., low or high pH, i.e., pH 4-6 or pH 8-11, respectively), in particular at free (i.e., unbound, therefore in solution) calcium concentrations below 60 ppm, include any of the mutations listed in the "Altered Properties" section. The stability may be determined as described in the "Methods" section below.

1.8.2 $Ca^{2+}$ Stability

Altered $Ca^{2+}$ stability means the stability of the enzyme under $Ca^{2+}$ depletion has been improved, i.e., higher or lower stability in the present context. In the context of the presently described variants, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the in "Altered Properties" section.

1.8.3 Specific Activity

In a further aspect, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the in "Altered properties" section. The specific activity may be determined as described in the "Methods" section below.

1.8.4 Oxidation Stability

The described variants may have altered oxidation stability, in particular higher oxidation stability, in comparison to the parent alpha-amylase. Increased oxidation stability is advantageous in, e.g., detergent compositions and decreased oxidation stability may be advantageous in composition for starch liquefaction. Oxidation stability may be determined as described in the "Methods" section below.

1.8.5 Altered pH Profile

Important positions and mutations with respect to obtaining variants with altered pH profile, in particular improved activity at especially high pH (i.e., pH 8-10.5) or low pH (i.e., pH 4-6) include mutations of amino residues located close to the active site residues.

Preferred specific mutations/substitutions are the ones listed above in the section "Altered Properties" for the positions in question. Suitable assays are described in the "Methods" section below.

1.8.6 Wash Performance

Important positions and mutations with respect to obtaining variants with improved wash performance at especially high pH (i.e., pH 8.5-11) include the specific mutations/substitutions listed above in the section "Altered Properties" for the positions in question. The wash performance may be tested as described below in the "Methods" section.

2. Methods of Preparing α-Amylase Variants

Thus, one aspect provides for *Bacillus* sp. strain TS-23 α-amylase sequence in creating recombinant forms that include other previously determined amino acid substitutions, deletions, transversions, insertions, and combinations thereof to produce variants of the *Bacillus* sp. strain TS-23 α-amylase. These variants can have additional production enhancement, increased pH stability, increased temperature stability, reduced requirements for $Ca^{2+}$, increased specific activity, increased dishwashing or washing performance, increased solubility, increased storage stability, or combinations thereof. Methods of recombinantly generating the variants could be performed using the provided sequences and vectors, or using other modalities known in the art.

Several methods for introducing mutations into genes are known in the art. After a brief discussion of the cloning of α-amylase-encoding DNA sequences, methods for generating mutations at specific sites within the α-amylase-encoding sequence will be discussed.

2.1 Cloning a DNA Sequence Encoding an α-Amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoamidite method described by S. L. Beaucage and M. H. Caruthers, *Tetrahedron Letters* 22: 1859-1869 (1981) or the method described by Matthes et al., *EMBO J.* 3: 801-895 (1984). In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202, or R. K. Saiki et al., *Science* 239: 487-491 (1988).

2.2 Site-Directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment), and the construct is ligated using T4 ligase. A specific example of this method is described in Morinaga et al., *Biotechnology* 2: 636-639 (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long, *Analytical Biochem.* 180: 147-151 (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

2.3 Expression of Alpha-Amylase Variants

According to one aspect, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant described herein may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant described herein, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Geobacillus stearothermophilus* maltogenic amylase gene (amyM), the promoters of the *Bacillus amyloliquefaciens* alpha-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral alpha-amylase, *A. niger* acid stable alpha-amylase, *A. niger* glucoamylase, *Rhizomucor miehei* lipase, *A. oryzae* alkaline protease, *A. oryzae* triose phosphate isomerase, or *A. nidulans* acetamidase.

The expression vector may also comprise a suitable transcription terminator and, in eukaryotes, polyadenylation sequences operably connected to the DNA sequence encoding an alpha-amylase variant described herein. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracycline resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct encoding an alpha-amylase variant described herein, the promoter, terminator and other elements, respectively, and to insert them into suitable vectors containing the information necessary for replication, are well known to persons skilled in the art (cf., for instance, Sambrook et al., MOLECULAR CLONING: A LABORATORY MANUAL, 2nd Ed., Cold Spring Harbor, 1989).

The cell, either comprising a DNA construct or an expression vector as defined above, is advantageously used as a host cell in the recombinant production of an alpha-amylase variant described herein. The cell may be transformed with a described DNA construct encoding a variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell may be a cell of a higher organism (i.e., eukaryote) such as a mammal or an insect, but is preferably a microbial cell, e.g., a bacterial or a fungal (including yeast) cell.

Examples of suitable bacteria are Gram-positive bacteria such as *Bacillus subtilis, Bacillus licheniformis, Bacillus lentus, Bacillus brevis, Geobacillus stearothermophilus, Bacillus alkalophilus, Bacillus amyloliquefaciens, Bacillus coagulans, Bacillus circulars, Bacillus lautus, Bacillus megaterium, Bacillus thuringiensis,* or *Streptomyces lividans* or *Streptomyces murinus,* or gram-negative bacteria such as *E. coli.* The transformation of the bacteria may, for instance, be effected by protoplast transformation or by using competent cells in a manner known per se.

The yeast organism may favorably be selected from a species of *Saccharomyces* or *Schizosaccharomyces,* e.g. *Saccharomyces cerevisiae.* The filamentous fungus may advantageously belong to a species of *Aspergillus,* e.g., *Aspergillus oryzae* or *Aspergillus niger.* Fungal cells may be transformed by a process involving protoplast formation and transformation of the protoplasts followed by regeneration of the cell wall in a manner known per se. A suitable procedure for transformation of *Aspergillus* host cells is described for example in EP 238 023.

In a yet further aspect, a method of producing an alpha-amylase variant is disclosed, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant described herein. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

3. Industrial Applications

The alpha-amylase variants presented herein possess valuable properties allowing for a variety of industrial applications. In particular, the enzyme variants are applicable as a component in washing, dishwashing, and hard surface cleaning detergent compositions.

One or more of the variants with altered properties may be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference in their entirety). Also contemplated are compositions for starch conversion purposes, which may beside the variant described herein, also comprise a glucoamylase, pullulanase, and other alpha-amylases.

Further, one or more of the variants are also particularly useful in the production of sweeteners and ethanol (see, e.g., U.S. Pat. No. 5,231,017 hereby incorporated by reference herein in its entirety), such as fuel, drinking and industrial ethanol, from starch or whole grains.

The variants herein may also be useful for desizing of textiles, fabrics and garments (see, e.g., WO 95/21247, U.S. Pat. No. 4,643,736, and EP 119,920 hereby incorporated by reference herein in their entirety), beer making or brewing, in pulp and paper production.

3.1 Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference herein in their entirety.

In an embodiment the starch conversion process degrading starch to lower molecular weight carbohydrate components such as sugars or fat replacers includes a debranching step.

3.2 Starch to Sugar Conversion

In the case of converting starch into a sugar the starch is depolymerized. A such depolymerization process consists of a pre-treatment step and two or three consecutive process steps, viz a liquefaction process, a saccharification process and dependent on the desired end product, optionally an isomerization process.

3.3 Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process, there is a dramatic increase in viscosity. As the solids level is 30-40% in a typical industrial process, the starch has to be thinned or "liquefied" so that it can be handled. This reduction in viscosity is today mostly obtained by enzymatic degradation.

3.4 Liquefaction

During the liquefaction step, the long chained starch is degraded into branched and linear shorter units (maltodextrins) by an alpha-amylase. The liquefaction process is carried out at 105-110° C. for 5 to 10 minutes followed by 1-2 hours at 95° C. The pH lies between 5.5 and 6.2. In order to ensure optimal enzyme stability under these conditions, 1 mM of calcium is added (40 ppm free calcium ions). After this treatment, the liquefied starch will have a "dextrose equivalent" (DE) of 10-15.

3.5 Saccharification

After the liquefaction process, the maltodextrins are converted into dextrose by addition of a glucoamylase (e.g., OPTIDEX® L-400) and a debranching enzyme, such as an isoamylase (U.S. Pat. No. 4,335,208) or a pullulanase. Before this step, the pH is reduced to a value below 4.5, maintaining the high temperature (above 95° C.) to inactivate the liquefying alpha-amylase to reduce the formation of short oligosaccharide called "panose precursors," which cannot be hydrolyzed properly by the debranching enzyme.

The temperature is lowered to 60° C., and a glucoamylase and a debranching enzyme are added. The saccharification process proceeds for 24-72 hours.

Normally, when denaturing the α-amylase after the liquefaction step about 0.2-0.5% of the saccharification product is the branched trisaccharide, Glc pα1-6Glc pα1-4Glc (panose), which cannot be degraded by a pullulanase. If active, amylase from the liquefaction step is present during saccharification (i.e., no denaturing), this level can be as high as 1-2%, which is highly undesirable as it lowers the saccharification yield significantly.

3.6 Isomerization

When the desired final sugar product is, e.g., high fructose syrup, the dextrose syrup may be converted into fructose. After the saccharification process, the pH is increased to a value in the range of 6-8, preferably pH 7.5, and the calcium is removed by ion exchange. The dextrose syrup is then converted into high fructose syrup using, e.g., an immobilized glucose isomerase (such as Gensweet® IGI-HF).

3.7 Ethanol Production

In general alcohol production (ethanol) from whole grain can be separated into 4 main steps: (1) Milling, (2) Liquefaction, (3) Saccharification, and (4) Fermentation.

3.7.1 Milling

The grain is milled in order to open up the structure and allow for further processing. Two processes used are wet or dry milling. In dry milling, the whole kernel is milled and used in the remaining part of the process. Wet milling gives a very good separation of germ and meal (starch granules and protein) and is, with a few exceptions, applied at locations where there is a parallel production of syrups.

3.7.2 Liquefaction

In the liquefaction process, the starch granules are solubilized by hydrolysis to maltodextrins mostly of a DP higher than 4. The hydrolysis may be carried out by acid treatment or enzymatically by alpha-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

3.7.3 Saccharification

To produce low molecular sugars $DP_{1-3}$ that can be metabolized by yeast, the maltodextrin from the liquefaction must be further hydrolyzed. The hydrolysis is typically done enzymatically by glucoamylases, alternatively alpha-glucosidases or acid alpha-amylases can be used. A full saccharification step may last up to 72 hours, however, it is common only to do a pre-saccharification of typically 40-90 minutes and then complete saccharification during fermentation (SSF). Saccharification is typically carried out at temperatures from 30-65° C., typically around 60° C., and at pH 4.5.

3.7.4 Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

3.8 Distillation

Following the fermentation, the mash is distilled to extract the ethanol.

The ethanol obtained according to the process described herein may be used as, e.g., fuel ethanol; drinking ethanol, i.e., potable neutral spirits; or industrial ethanol.

3.9 By-Products

Left over from the fermentation is the grain, which is typically used for animal feed either in liquid form or dried.

Further details on how to carry out liquefaction, saccharification, fermentation, distillation, and recovery of ethanol are well known to the skilled person.

According to a process described herein, the saccharification and fermentation may be carried out simultaneously or separately.

3.10 Pulp and Paper Production

A variant alkaline alpha-amylase as described herein may also be used in the production of lignocellulosic materials, such as pulp, paper and cardboard, from starch reinforced waste paper and cardboard, especially where repulping occurs at pH above 7, and where amylases facilitate the disintegration of the waste material through degradation of the reinforcing starch. The alpha-amylase is especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The alpha-amylases described herein may also be very useful in modifying starch where enzymatically modified starch is used in papermaking together with alkaline fillers such as calcium carbonate, kaolin and clays. With the described alkaline alpha-amylases, it becomes possible to modify the starch in the presence of the filler thus allowing for a simpler integrated process.

3.11 Desizing of Textiles, Fabrics and Garments

An alpha-amylase may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fiber damage because of the rather aggressive chemicals used. Accordingly, it would be desirable to use the alpha-amylases variants, as they have an improved performance in alkaline solutions. The alpha-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, and EP 119,920, which are hereby incorporated by reference herein in their entirety.

Commercially available products for desizing include OPTISIZE® FLEX from Danisco US Inc., Genencor Division.

Also contemplated are compositions and methods of treating fabrics (e.g., to desize a textile) using one or more *Bacillus* sp. strain TS-23 α-amylases or variants thereof. The enzyme can be used in any fabric-treating method, which are well known in the art, see, e.g., U.S. Pat. No. 6,077,316. For example, in one aspect, the feel and appearance of a fabric is improved by a method comprising contacting the fabric with a *Bacillus* sp. strain TS-23 α-amylase or variant thereof in a solution. In one aspect, the fabric is treated with the solution under pressure.

In one aspect, the enzymes are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. Also provided is a method of desizing comprising enzymatic hydrolysis of the size by the action of a *Bacillus* sp. strain TS-23 α-amylase or variant thereof.

The enzymes can be used alone or with other desizing chemical reagents and/or desizing enzymes to desize fabrics, including cotton-containing fabrics, as detergent additives, e.g., in aqueous compositions. A *Bacillus* sp. strain TS-23 α-amylase or variant thereof can also be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The enzymes can be used in methods of finishing denim garments (e.g., a "bio-stoning process"), enzymatic desizing and providing softness to fabrics, and/or finishing process. Dosage of the amylase varies depending on the process type. Smaller dosages would require more time than larger dosages of the same enzyme. However, there is no upper limit on the amount of a desizing amylase present other than that dictated by the physical constraints of the solution. Thus, the limit of the enzyme may be the amount capable of solubilization in the solution. Typically, desizing enzymes, such as α-amylases, are incorporated in to the treating composition in an amount from about 0.00001% to about 2% of enzyme protein by weight of the fabric; or from about 0.0001% to about 1% of enzyme protein by weight of the fabric; or from about 0.001% to about 0.5% of enzyme protein by weight of the fabric; and in another example would be from about 0.01% to about 0.2% of enzyme protein by weight of the fabric.

3.12 Beer Making

The variant alpha-amylases provided for herein may also be very useful in a beer-making process; the alpha-amylases will typically be added during the mashing process.

3.13 Detergent Compositions

The variant alpha-amylases described herein may be added to and thus become a component of a detergent composition.

The detergent composition provided for herein may for example be formulated as a hand or machine laundry detergent composition, including a laundry additive composition suitable for pretreatment of stained fabrics and a rinse added fabric softener composition or be formulated as a detergent composition for use in general household hard surface cleaning operations, or be formulated for hand or machine dishwashing operations.

In a specific aspect, there is provided for herein a "detergent additive" comprising a variant enzyme described herein. The detergent additive as well as the detergent composition may comprise one or more other enzymes such as a protease, a lipase, a peroxidase, another amylolytic enzyme, e.g., another alpha-amylase, glucoamylase, maltogenic amylase, CGTase and/or a cellulose, mannanase (such as MANNASTAR™ from Danisco US Inc., Genencor Division), pectinase, pectin lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease or a chymotrypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described e.g., in WO 89/06279). Examples of trypsin-like proteases are trypsin (e.g., of porcine or bovine origin), and the *Fusarium* protease described in WO 89/06270 and WO 94/25583.

Exemplary commercially available protease enzymes include ALCALASE®, SAVINASE®, PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3® and FN4® (Danisco US Inc., Genencor Division).

Lipases: Suitable lipases include those of bacterial or fungal origin. Chemically modified or protein engineered mutants are included. Examples of useful lipases include but are not limited to lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422). Additional exemplary lipase variants contemplated for use in the formulations include those described in WO 92/05249, WO 94/01541, EP 407 225, EP 260 105, WO 95/35381, WO 96/00292, WO 95/30744, WO 94/25578, WO 95/14783, WO 95/22615, WO 97/04079, and WO 97/07202.

Commercially available lipase enzymes include LIPOLASE™ and LIPOLASE ULTRA™ (Novozymes A/S).

Polyesterases: suitable polyesterases can be included in composition. Suitable polyesterases include for example those described in WO 01/34899 and WO 01/14629.

Amylases: One or more additional amylases (in addition to the variant amylase(s) described herein) may also be included. Suitable amylases (alpha and/or beta) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839. Examples of useful alpha-amylases are the variants described in WO 94/18314, WO 96/39528, WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available alpha-amylases are DURAMYL™, LIQUEZYME™ TERMAMYL™, NATALASE™, STAINZYME™ PLUS, STAINZYME™ ULTRA, FUNGAMYL™ and BAN™ (Novozymes A/S), RAPIDASE™ and PURASTAR™ (from Danisco US Inc., Genencor Division).

Cellulases: Cellulases may be added to the compositions. Suitable cellulases include those of bacterial or fungal origin. Chemically modified or protein engineered mutants are included. Suitable cellulases include but are not limited to cellulases from the genera *Bacillus, Pseudomonas, Trichoderma, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757, and WO 89/09259. Exemplary *Trichoderma reesei* cellulases are disclosed in U.S. Pat. No. 4,689,297, U.S. Pat. No. 5,814,501, U.S. Pat. No. 5,324,649, WO 92/06221 and WO 92/06165. Exemplary *Bacillus* cellulases are disclosed in U.S. Pat. No. 6,562,612.

Commercially available cellulases include CELLUZYME®, and CAREZYME® (Novozymes A/S), CLAZINASE®, and PURADAX HA® (Danisco US Inc., Genencor Division), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME® (Novozymes A/S).

The detergent enzyme(s) may be included in a detergent composition by adding separate additives containing one or more enzymes, or by adding a combined additive comprising all of these enzymes. A detergent additive, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Generally, the detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels contained for example about 30% water or less.

The detergent composition comprises one or more surfactants, which may be non-ionic including semi-polar and/or anionic and/or cationic and/or zwitterionic. The surfactants are typically present at a level of from 0.1% to 60% by weight.

When included therein, the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein, the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0-65% of a detergent builder or complexing agent, such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid co-polymers.

The detergent may contain a bleaching system that may comprise a $H_2O_2$ source, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g. the amide, imide, or sulfone type peroxyacids). The bleaching system can also be an enzymatic bleaching system. See, e.g., WO 05/056782.

The enzyme(s) of the detergent composition described herein may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, and/or perfumes (and any combination thereof).

It is at present contemplated that in the detergent compositions, in particular a *Bacillus* sp. strain TS-23 α-amylase or variant thereof, may be added in an amount corresponding to about 0.01 to about 100 mg of enzyme protein per liter of wash liquor, for example about 0.05 to about 5.0 mg of enzyme protein per liter of wash liquor, or about 0.1 to about 1.0 mg of enzyme protein per liter of wash liquor.

One or more of the variant enzymes described herein may additionally be incorporated in the detergent formulations disclosed in WO 97/07202, which is hereby incorporated as reference.

4. Compositions and Use

One or more of the variant enzymes described herein may also be used in methods for using an alpha-amylase variant in detergents, in particular laundry detergent compositions and dishwashing detergent compositions, hard surface cleaning compositions, and in composition for desizing of textiles, fabrics or garments, for production of pulp and paper, beer making, ethanol production, and starch conversion processes as described above.

4.1 Laundry Detergent Compositions and Use

According to one embodiment, one or more *Bacillus* sp. strain TS-23 α-amylases or variants thereof, may typically be a component of a laundry detergent composition. As such, it may be included in the detergent composition in the form of a non-dusting granulate, a stabilized liquid, or a protected enzyme. The dry formulations may be in the form of a granulate or microgranulate. Non-dusting granulates may be produced, e.g. as disclosed in U.S. Pat. Nos. 4,106,991 and 4,661,452, and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in for example EP Appln. No. 238,216. Polyols have long been recognized as stabilizers of proteins as well as improving solubility of proteins. See, e.g., J. K. Kaushik et al., "Why is trehalose an exceptional protein stabilizer? An analysis of the thermal stability of proteins in the presence of the compatible osmolyte trehalose," *J. Biol. Chem.* 278: 26458-65 (2003) and the references cited therein; and Monica Conti et al., "Capillary isoelectric focusing: the problem of protein solubility," *J. Chromatography* 757: 237-245 (1997).

The composition may comprise a *Bacillus* sp. strain TS-23 α-amylase or variants thereof as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase, as well as other enzymes discussed below. The additional enzyme(s) may be producible by means of a microorganism belonging to the genera *Aspergillus*, *Trichoderma*, *Humicola* (e.g. *H. insolens*), and *Fusarium*. Exemplary members of the *Aspergillus* genus include *Aspergillus aculeatus*, *Aspergillus awamori*, *Aspergillus niger*, or *Aspergillus oryzae*. Exemplary members of the genus *Fusarium* include *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundinis*, *Fusarium oxysporum*, *Fusarium reticulatum*, *Fusarium roseum*, *Fusarium sambucinum*, *Fusarium sarcochroum*, *Fusarium sulphureum*, *Fusarium torulosum*, *Fusarium trichothecioides*, and *Fusarium venenatum*.

The detergent composition may be in any useful form, e.g., powders, granules, pastes, or liquids. A liquid detergent may be aqueous, typically containing up to about 70% of water, and 0% to about 30% of organic solvent. It can also be a detergent composition in the form of a compact gel type containing only about 30% water. Enzymes may be used in any detergent composition compatible with the stability of the enzyme. Enzymes can be protected against generally deleterious components by known forms of encapsulation as for example by granulation or sequestration in hydro gels. Enzymes and specifically α-amylases are not limited to laundry and dish washing applications, but can also be used in surface cleaners, ethanol production from starch or biomass.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as lipase, cutinase, protease, cellulase, peroxidase, and/or laccase in any combination. See supra.

The detergent may optionally contain about 1% to about 65% of a detergent builder or complexing agent, such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may optionally comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may optionally contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxy acids of e.g. the amide, imide, or sulfone type. The bleaching system can also be an enzymatic bleaching system, where a perhydrolase activates peroxide, as described in for example WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) is usually neutral or alkaline, e.g., pH about 7.0 to about 11.0.

Particular forms of detergent compositions comprising a *Bacillus* sp. strain TS-23 α-amylase or variant thereof, can be formulated to include:

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0 to about 5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g. $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0 to about 5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0 to about 5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0 to about 5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0 to about 5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0 to about 5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0 to about 5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0 to about 5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0 to about 5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0 to about 5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0 to about 5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0 to about 3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0 to about 5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0 to about 3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," *Nature* 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

A *Bacillus* sp. strain TS-23 α-amylase or variant thereof, may be incorporated in concentrations conventionally employed in detergents. It is at present contemplated that, in the detergent composition, a *Bacillus* sp. strain TS-23 α-amylase or variant thereof, may be added in an amount corresponding to 0.00001-1.0 mg (calculated as pure enzyme protein) of enzyme per liter of wash liquor.

In another embodiment, a 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for manual or machine laundry operations.

In a specific aspect, the detergent composition can further comprise 2,6-β-D-fructan hydrolase, one or more α-amylases in addition to the *Bacillus* sp. strain TS-23 α-amylase or variant thereof, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof.

In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

4.2 Dishwash Detergent Compositions

The enzyme variants may also be used in dish wash detergent compositions, including the following:

1) Powder Automatic Dishwashing Composition

| | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

2) Powder Automatic Dishwashing Composition

| | |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10% |

3) Powder Automatic Dishwashing Composition

| | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

4) Powder Automatic Dishwashing Composition

| | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) Polymer | 0-3% |
| | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

5) Powder Automatic Dishwashing Composition

| | |
|---|---|
| Nonionic surfactant | 1-7% |
| Sodium disilicate | 18-30% |
| Trisodium citrate | 10-24% |
| Sodium carbonate | 12-20% |
| Monopersulphate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

6) Powder and Liquid Dishwashing Composition with Cleaning Surfactant System

| | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |

| | |
|---|---|
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |

7) Non-Aqueous Liquid Automatic Dishwashing Composition

| | |
|---|---|
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

8) Non-Aqueous Liquid Dishwashing Composition

| | |
|---|---|
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

9) Thixotropic Liquid Automatic Dishwashing Composition

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

10) Liquid Automatic Dishwashing Composition

| | |
|---|---|
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

11) Liquid Automatic Dishwashing Composition Containing Protected Bleach Particles

| | |
|---|---|
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

11) Automatic dishwashing compositions as described in 1), 2), 3), 4), 6) and 10), wherein perborate is replaced by percarbonate.

12) Automatic dishwashing compositions as described in 1)-6) which additionally contain a manganese catalyst. The manganese catalyst may, e.g., be one of the compounds described in "Efficient manganese catalysts for low-temperature bleaching", *Nature* 369: 637-639, 1994.

4.3 Biofilm Removal Compositions and Use

The composition may comprise a *Bacillus* sp. strain TS-23 α-amylase or variant thereof, as the major enzymatic component, e.g., a mono-component composition for use in removing biofilms. Alternatively, the composition may comprise multiple enzymatic activities, such as multiple amylases, or a cocktail of enzymes including any combination of the following: aminopeptidase, amylase (β-, or α-, or glucoamylase), carbohydrase, carboxypeptidase, catalase, cellulase, chitinase, cutinase, cyclodextrin glycosyltransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, and/or xylanase, or any combination thereof for removing biofilms. The additional enzyme(s) may be producible by means of a microorganism belonging to the genera *Aspergillus*, *Trichoderma*, *Humicola* (e.g., *H. insolens*), and

*Fusarium*. Exemplary members from the *Aspergillus* genus include *Aspergillus aculeatus, A. awamori, A. niger*, and *A. oryzae*. Exemplary members of the *Fusarium* genus include *F. bactridioides, F. cerealis, F. crookwellense, F. culmorum, F. graminearum, F. graminum, F. heterosporum, F. negundinis, F. oxysporum, F reticulatum, F. roseum, F. sambucinum, F. sarcochroum, F. sulphureum, F. torulosum, F. trichothecioides*, and *F. venenatum*.

The *Bacillus* sp. strain TS-23 α-amylase or variant thereof, comprising compositions may be prepared in accordance with methods known in the art and may be in the form of a liquid or a dry composition. For instance, the *Bacillus* sp. strain TS-23 α-amylase or variant thereof, containing composition may be in the form of a granulate or a microgranulate. The polypeptide to be included in the composition may be stabilized in accordance with methods known in the art.

Examples are given below of exemplary uses of the polypeptide compositions. The dosage of the *Bacillus* sp. strain TS-23 α-amylase or variant thereof, containing composition and other conditions under which the composition is used may be determined using methods known in the art.

The *Bacillus* sp. strain TS-23 α-amylases or variants thereof, are further contemplated for use in a composition along with a 2,6-β-D-fructan hydrolase or variant thereof.

Another aspect contemplates compositions and methods for disintegrating and/or removing biofilms. The term "disintegration" as used herein is to be understood as hydrolysis of polysaccharides in a biofilm matrix connecting and binding together individual microbial cells in the biofilm, whereby the microbial cells can be released and removed from the biofilm. The biofilm is typically present at a surface and the disintegration of the biofilm can be achieved by bringing the surface in contact, e.g., by immersing, covering or splashing the surface with an aqueous medium comprising a *Bacillus* sp. strain TS-23 α-amylase or variant thereof, or one or more other enzymes responsible for breaking down biofilms, such as but not limited to 2,6-β-D-fructan hydrolase. The composition can be used to hydrolyse slime, e.g., in white waters in the pulping and paper industry.

The *Bacillus* sp. strain TS-23 α-amylases or variants thereof, may be present in the amount of 0.0001 to 10000 mg/L; 0.001-1000 mg/L; 0.01-100 mg/L; or 0.1-10 mg/L. Additional enzymes and enzyme variants may be present in similar amounts or less.

The process may suitably be performed at temperatures from about ambient temperature to about 70° C. Exemplary temperature ranges include from about 30° C. to about 60° C., e.g., about 40° C. to about 50° C.

A suitable pH for the hydrolyzing biofilms lies within from about 3.5 to about 8.5. Exemplary pH ranges include from about 5.5 to about 8, e.g. from about 6.5 to about 7.5. The contact time or reaction time for the enzyme to effectively removing a biofilm may vary considerably, depending on the biofilm properties and the frequency of which a surface is treated with the enzyme alone or in combination with other biofilm degrading enzymes, such as 2,6-β-D-fructan hydrolase. Exemplary reaction time can include within about 0.25 to about 25 hours, and from about 1 to about 10 hours, e.g. about 2 hours.

Additional biofilm degrading enzymes that can be combined with the *Bacillus* sp. strain TS-23 α-amylase or variants thereof, and 2,6-β-D-fructan hydrolases include but are not limited to cellulases, hemicellulases, xylanases, other amylases including other α-amylases, lipases, proteases, and/or pectinases.

The *Bacillus* sp. strain TS-23 α-amylase or variants thereof, can further be combined with antimicrobial agents such as enzymatic or non-enzymatic biocides. An enzymatic biocide may, e.g., be a composition comprising an oxidoreductase, e.g. a laccase or a peroxidase, especially haloperoxidase, and optionally an enhancing agent, such as an alkyl syringate, as described for example in International PCT applications WO 97/42825 and DK 97/1273.

The surface from which a biofilm for example can be removed and/or cleaned off is a hard surface, which by definition relates to any surface that is essentially non-permeable to microorganisms. Examples of surfaces are surfaces made from metal, e.g. stainless steel alloys, plastics/synthetic polymers, rubber, board, glass, wood, paper, textile, concrete, rock, marble, gypsum and ceramic materials which optionally may be coated, e.g. with paint, enamel, polymers and the like. Accordingly, the surface may be a member of a system holding, transporting, processing, or in contact with aqueous solutions such as water supply systems, food processing systems, cooling systems, chemical processing systems or pharmaceutical processing systems. The compositions and methods of using the compositions for removing biofilm in the wood processing industry, such as the pulp and/or paper industry. Accordingly, the enzyme and compositions containing the enzyme are useful in a conventional cleaning-in-place (C-I-P) system. The surface may a member of a system unit such as pipes, tanks, pumps, membranes, filters, heat exchangers, centrifuges, evaporators, mixers, spray towers, valves and reactors. The surface may also be or be a part of utensils used in the medical science and industry such as contaminated endoscopes, prosthetic devices or medical implants.

The compositions for biofilm removal is also contemplated for preventing so-called bio-corrosion occurring when a metal surface, e.g. a pipeline, is attacked by a microbial biofilm, that is by disintegrating the biofilm thereby preventing the microbial cells of the biofilm from creating a biofilm environment, which corrodes the metal surface to which it is attached.

Another application for anti-biofilm compositions is for oral care. The surface may however also be of biological origin, such as mucous membranes, skin, teeth, hair, nails etc.

Teeth with dental plaque, e.g., by incorporating the enzymes into toothpaste, and contaminated contact lenses are encompassed as surfaces. Accordingly, a *Bacillus* sp. strain TS-23 α-amylase or variants thereof, can be used for compositions and processes for making a medicament for disintegration of plaque present on a human or animal tooth. A further use is disintegration of biofilm from mucous membranes, such as biofilm in lungs in patients suffering from cystic fibrosis.

Accordingly, in a still further aspect relates to an oral care composition comprising a recombinant enzyme, such as a purified enzyme that is essentially free of any active contaminants. An oral care composition may suitably comprise an amount of a recombinant enzyme.

Other biofilm degrading enzymes for use in oral care compositions include but are not limited to 2,6-β-D-fructan hydrolase activity in the oral care composition. Contemplated enzyme activities include activities from the group of enzymes comprising dextranase; mutanases; oxidases, such as glucose oxidase, L-amino acid oxidase, peroxidases, such as e.g. the *Coprinus* sp. peroxidases described in WO 95/10602, or lactoperoxidase, haloperoxidases, especially haloperoxidase derivable from *Curvularia* sp., in particular *C. verruculosa* and *C. inaequalis*; laccases; proteases such as papain, acidic protease (e.g. the acidic proteases described in WO 95/02044, endoglucosidases, lipases, amylases, including amyloglucosidases, such as AMG (Novo Nordisk A/S); anti-microbial enzymes, and mixtures thereof.

The oral care composition may have any suitable physical form (i.e. powder, paste, gel, liquid, ointment, tablet etc.). An "oral care composition" includes a composition, which can be used for maintaining or improving the oral hygiene in the mouth of humans and animals, by preventing dental caries, preventing the formation of dental plaque and tartar, removing dental plaque and tartar, preventing and/or treating dental diseases etc. At least in the context oral care compositions do also encompass products for cleaning dentures, artificial teeth and the like. Examples of such oral care compositions includes toothpaste, dental cream, gel or tooth powder, odontic mouth washes, pre- or post brushing rinse formulations, chewing gum, lozenges, and candy. Toothpastes and tooth gels typically include abrasive polishing materials, foaming agents, flavoring agents, humectants, binders, thickeners, sweetening agents, whitening/bleaching/stain removing agents, water, and optionally additional enzymes and enzyme combinations.

Mouthwashes, including plaque-removing liquids, typically comprise a water/alcohol solution, flavor, humectant, sweetener, foaming agent, colorant, and optionally additional enzymes or enzyme combinations.

Abrasive polishing material might also be incorporated into the oral care composition such as a dentifrice.

Accordingly, abrasive polishing material can include alumina and hydrates thereof, such as alpha alumina trihydrate; magnesium trisilicate; magnesium carbonate; kaolin; aluminosilicates, such as calcined aluminum silicate and aluminum silicate; calcium carbonate; zirconium silicate; and also powdered plastics, such as polyvinyl chloride; polyamides; polymethyl methacrylate; polystyrene; phenol-formaldehyde resins; melamine-formaldehyde resins; urea-formaldehyde resins; epoxy resins; powdered polyethylene; silica xerogels; hydrogels and aerogels and the like. Also suitable as abrasive agents are calcium pyrophosphate; water-insoluble alkali metaphosphates; dicalcium phosphate and/or its dihydrate, dicalcium orthophosphate; tricalcium phosphate; particulate hydroxyapatite and the like. It is also possible to employ mixtures of these substances.

Dependent on the oral care composition, the abrasive product may be present in from about 0% to about 70% by weight, or from about 1% to about 70%. For toothpastes, the abrasive material content typically lies in the range of from 10% to 70% by weight of the final toothpaste.

Humectants are employed to prevent loss of water from e.g. tooth pastes. Suitable humectants for use in oral care compositions include the following compounds and mixtures thereof: glycerol; polyol; sorbitol; polyethylene glycols (PEG); propylene glycol; 1,3-propanediol; 1,4-butanediol; hydrogenated partially hydrolyzed polysaccharides and the like. Humectants are in general present in from 0% to about 80%, or from about 5% to about 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing a dentifrice product. Thickeners may be present in toothpaste creams and gels in an amount of from about 0.1% to about 20% by weight, and binders to the extent of from about 0.01 to about 10% by weight of the final product.

As foaming agent soap, anionic, cationic, non-ionic, amphoteric and/or zwitterionic surfactants can be used. These may be present at levels of from 0% to about 15%, from about 0.1% to about 13%, or from about 0.25% to about 10% by weight of the final product.

Surfactants are only suitable to the extent that they do not exert an inactivation effect on the *Bacillus* sp. strain TS-23 α-amylase or variants thereof. Surfactants include fatty alcohol sulfates, salts of sulfonated mono-glycerides or fatty acids having 10 to 20 carbon atoms, fatty acid-albumen condensation products, salts of fatty acids amides and taurines and/or salts of fatty acid esters of isethionic acid.

Suitable sweeteners include saccharin for use in the formulations.

Flavors, such as spearmint, are usually present in low amounts, such as from about 0.01% to about 5% by weight, especially from about 0.1% to about 5%. Whitening/bleaching agents include $H_2O_2$ and may be added in amounts less that about 5%, or from about 0.25% to about 4%, calculated by the weight of the final product. The whitening/bleaching agents may be an enzyme, such as an oxidoreductase. Examples of suitable teeth bleaching enzymes include for example those described in WO 97/06775.

Water is usually added in an amount giving e.g. toothpaste a flowable form.

Further water-soluble anti-bacterial agents, such as chlorohexidine digluconate, hexetidine, alexidine, Triclosan®, quaternary ammonium anti-bacterial compounds and water-soluble sources of certain metal ions such as zinc, copper, silver and stannous (e.g., zinc, copper and stannous chloride, and silver nitrate) may also be included.

Also contemplated is the addition of compounds that can be used as fluoride source, dyes/colorants, preservatives, vitamins, pH-adjusting agents, anti-caries agents, desensitizing agents, etc.

Biofilm degrading enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids, which form the structural components of bacterial cell walls and membranes.

Dextranase and other carbohydrases, such as the 2,6-β-D-fructan hydrolase, break down the organic skeletal structure produced by bacteria that forms a matrix for bacterial adhesion. Proteases and amylases, not only prevent plaque formation, but also prevent the development of calculus by breaking-up the carbohydrate-protein complex that binds calcium, preventing mineralization.

A toothpaste may typically comprise the following ingredients (in weight % of the final toothpaste composition): abrasive material to about 70%; humectant: 0% to about 80%; thickener: about 0.1% to about 20%; binder: about 0.01% to about 10%; sweetener: about 0.1% to about 5%; foaming agent: 0% to about 15%; whitener: 0% to about 5%; and enzymes: about 0.0001% to about 20%.

In a specific embodiment, a toothpaste has a pH in the range from about 6.0 to about 8.0, and comprises: a) about 10% to about 70% abrasive material; b) 0% to about 80% humectant; c) 0.1% to about 20% thickener; d) 0.01% to about 10% binder; e) about 0.1% to about 5% sweetener; f) 0% to about 15% foaming agent; g) 0% to about 5% whitener; i) about 0.0001% to about 20% enzymes.

Said enzymes referred to under i) include a *Bacillus* sp. strain TS-23 α-amylase or variants thereof, alone, or in combination with other biofilm degrading enzymes, such as 2,6-β-D-fructan hydrolase, and optionally other types of enzymes mentioned above known to be used in toothpastes and the like.

A mouth wash may typically comprise the following ingredients (in weight % of the final mouth wash composition): 0% to about 20% humectant; 0% to about 2% surfactant; 0% to about 5% enzymes; 0% to about 20% ethanol; 0% to about 2% other ingredients (e.g. flavor, sweetener active ingredients such as fluorides). The composition can also contain from about 0% to about 70% water.

The mouthwash composition may be buffered with an appropriate buffer e.g. sodium citrate or phosphate in the pH-range of about 6.0 to about 7.5. The mouthwash may be in non-diluted form (i.e. must be diluted before use).

The oral care compositions may be produced using any conventional method known to the art of oral care.

4.4 Starch Processing Compositions and Use

In another aspect, compositions with a disclosed *Bacillus* sp. strain TS-23 α-amylase or variants thereof, can be utilized for starch liquefaction or saccharification.

One aspect contemplates compositions and uses of compositions to produce sweeteners from starch. A "traditional" process for conversion of starch to fructose syrups normally consists of three consecutive enzymatic processes, viz. a liquefaction process followed by a saccharification process, and an isomerization process. During the liquefaction process, starch is degraded to dextrins by a *Bacillus* sp. strain TS-23 α-amylase or variants thereof, at pH values between about 5.5 and about 6.2 and at temperatures of about 95° C. to about 160° C. for a period of approximately 2 hours. In order to ensure optimal enzyme stability under these conditions, 1 mM of calcium can be added (at least 40 ppm free calcium ions). Starch processing is useful for producing alcohol (e.g., cereal liquefaction for fuel and potable alcohol, alcohol brewing), starch liquefaction for sweetener production, cane sugar processing, and other food related starch processing goals. Other conditions can be used for different *Bacillus* sp. strain TS-23 α-amylases or variants thereof.

After the liquefaction process, the dextrins are converted into dextrose by addition of a glucoamylase (e.g. AMG™) and a debranching enzyme, such as an isoamylase or a pullulanase (e.g., Promozyme®). Before this step, the pH is reduced to a value below about 4.5, maintaining the high temperature (above 95° C.), and the liquefying *Bacillus* sp. strain TS-23 α-amylase or variant thereof, activity is denatured. The temperature is lowered to 60° C., and a glucoamylase and a debranching enzyme can be added. The saccharification process proceeds typically for about 24 to about 72 hours.

After the saccharification process, the pH is increased to a value in the range of about 6.0 to about 8.0, e.g., pH 7.5, and the calcium is removed by ion exchange. The dextrose syrup is then converted into high fructose syrup using, e.g., an immobilized glucose isomerase (such as Sweetzyme®).

At least one enzymatic improvement of this process can be performed. Reduction of the calcium dependency of the liquefying *Bacillus* sp. strain TS-23 α-amylase or variant thereof. Addition of free calcium is required to ensure adequately high stability of the *Bacillus* sp. strain TS-23 α-amylase or variant thereof, but free calcium strongly inhibits the activity of the glucose isomerase and needs to be removed, by means of an expensive unit operation, to an extent that reduces the level of free calcium to below 3-5 ppm. Cost savings can be obtained if such an operation could be avoided, and the liquefaction process could be performed without addition of free calcium ions.

For example, a less calcium-dependent enzyme, which is stable and highly active at low concentrations of free calcium (<40 ppm) can be utilized in the composition and procedures. Such a *Bacillus* sp. strain TS-23 α-amylase or variant thereof should have a pH optimum at a pH in the range of about 4.5 to about 6.5, or in the range of about 4.5 to about 5.5.

A *Bacillus* sp. strain TS-23 α-amylase or variant thereof can be used in laboratory and in industrial settings to hydrolyze starch or any maltodextrine-comprising compound for a variety of purposes. These *Bacillus* sp. strain TS-23 α-amylases or variants thereof can be used alone to provide specific hydrolysis or can be combined with other amylases to provide a "cocktail" with a broad spectrum of activity. Exemplary uses include the removal or partial or complete hydrolysis of starch or any maltodextrine-comprising compound from biological, food, animal feed, pharmaceutical, or industrial samples.

Another aspect contemplates compositions and methods of using the compositions in a fermentation process, wherein a starch substrate is liquefied and/or saccharified in the presence of the *Bacillus* sp. strain TS-23 α-amylase or variant thereof to produce glucose and/or maltose suitable for conversion into a fermentation product by a fermenting organism, such as a yeast. Such fermentation processes include a process for producing ethanol for fuel or drinking ethanol (potable alcohol), a process for producing a beverage, a process for producing desired organic compounds (e.g., such as citric acid, itaconic acid, lactic acid, gluconic acid, sodium gluconate, calcium gluconate, potassium gluconate, glucono delta lactone, or sodium erythorbate), ketones, amino acids (such as glutamic acid, sodium monoglutaminate), but also more complex compounds (e.g., antibiotics, such as penicillin, tetracyclin), enzymes, vitamins (e.g., riboflavin, vitamin $B_{12}$, β-carotene), and hormones, which are difficult to produce synthetically.

The starch to be processed may be a highly refined starch quality, such as at least 90%, at least 95%, at least 97%, or at least 99.5% pure. Alternatively, the starch can be a more crude starch containing material comprising milled whole grain including non-starch fractions such as germ residues and fibers. The raw material, such as whole grain, is milled in order to open up the structure and allowing for further processing. Two milling processes can be used: wet and dry milling. Also, corn grits such as milled corn grits may be applied.

Dry milled grain will, in addition to starch, comprise significant amounts of non-starch carbohydrate compounds. When such a heterogeneous material is processed by jet cooking *Bacillus* sp. strain TS-23 often only a partial gelatinization of the starch is achieved. As the *Bacillus* sp. strain TS-23 α-amylase or variant thereof has a high activity towards ungelatinized starch, the enzyme(s) may be advantageously applied in a process comprising liquefaction and/or saccharification jet cooked dry milled starch.

Furthermore, due to the superior hydrolysis activity of the *Bacillus* sp. strain TS-23 α-amylases or variants thereof, the need for glucoamylase during the saccharification step is greatly reduced. This allows saccharification to be performed at very low levels of glucoamylase activity. Glucoamylase activity is either absent, or if present, then present in an amount of no more than or even less than 0.5 AGU/g DS, or no more than or even less than 0.4 AGU/g DS, or no more than or even less than about 0.3 AGU/g DS, or less than 0.1 AGU, such as no more than or even less than about 0.05 AGU/g DS of starch substrate. "DS" is the unit of enzyme added per gram of dry solid substrate. Expressed in mg enzyme protein, the enzyme having glucoamylase activity is either absent or present in an in an amount of no more than or even less than about 0.5 mg EP/g DS, or no more than or even less than about 0.4 mg EP/g DS, or no more than or even less than about 0.3 mg EP/g DS, or no more than or even less than about 0.1 mg EP/g DS (e.g., no more than or even less than about 0.05 mg EP/g DS or no more than or even less than 0.02 mg EP/g DS of starch substrate). The glucoamylase may be derived from a strain within *Aspergillus* sp., *Talaromyces* sp., *Pachykytospora* sp., or *Trametes* sp., with exemplary examples being *Aspergillus niger, Talaromyces emersonii, Trametes cingulata*, or *Pachykytospora papyracea*.

The process may comprise a) contacting a starch substrate with a *Bacillus* sp. strain TS-23 α-amylase or variant thereof comprising a catalytic module having α-amylase activity and a carbohydrate-binding module, e.g., the polypeptide of the first aspect; b) incubating said starch substrate with said enzyme for a time and at a temperature sufficient to achieve conversion of at least 90%, or at least 92%, at least 94%, at least 95%, at least 96%, at least 97%, at least 98%, at least 99%, at least 99.5% w/w of said starch substrate into fermentable sugars; c) fermenting to produce a fermentation product; and d) optionally recovering the fermentation product. During the process steps b) and/or c), an enzyme having glucoamylase activity is either absent or present in an amount from 0.001 to 2.0 AGU/g DS, from 0.01 to 1.5 AGU/g DS, from 0.05 to 1.0 AGU/g DS, from 0.01 to 0.5 AGU/g DS. The enzyme having glucoamylase activity can either absent or present in an amount of no more than or even less than 0.5 AGU/g DS, or no more than or even less than 0.4 AGU/g DS, or no more than or even less than 0.3 AGU/g DS, or no more than or even less than 0.1 AGU/g DS (e.g., no more than or even less than 0.05 AGU/g DS of starch substrate). Expressed in mg enzyme protein, the enzyme having glucoamylase activity is either absent or present in an in an amount of no more than or even less than 0.5 mg EP/g DS, or no more than or even less than 0.4 mg EP/g DS, or no more than or even less than 0.3 mg EP/g DS, or no more than or even less than 0.1 mg EP/g DS (e.g., no more than or even less than 0.05 mg EP/g DS or no more than or even less than 0.02 mg EP/g DS of starch substrate). In the process steps a), b), c), and/or d) may be performed separately or simultaneously.

In another aspect the process may comprise: a) contacting a starch substrate with a yeast cell transformed to express a *Bacillus* sp. strain TS-23 α-amylase or variant thereof comprising a catalytic module having α-amylase activity and a carbohydrate-binding module; b) incubating said starch substrate with said yeast for a time and at a temperature sufficient to achieve conversion of at least 90% w/w of said starch substrate into fermentable sugars; c) fermenting to produce ethanol; d) optionally recovering ethanol. The steps a), b), and c) may be performed separately or simultaneously.

In yet another aspect, the process comprising hydrolysis of a slurry of gelatinized or granular starch, in particular hydrolysis of granular starch into a soluble starch hydrolysate at a temperature below the initial gelatinization temperature of said granular starch. In addition to being contacted with a polypeptide comprising a catalytic module having α-amylase activity and a carbohydrate-binding module. The starch can be contacted with any one or more of the following a fungal α-amylase (EC 3.2.1.1) and one or more of the following: a β-amylase (EC 3.2.1.2), and a glucoamylase (EC 3.2.1.3). In a further aspect, another amylolytic enzyme or a debranching enzyme, such as an isoamylase (EC 3.2.1.68), or a pullulanases (EC 3.2.1.41) may be added to the *Bacillus* sp. strain TS-23 α-amylase or variant thereof.

In an embodiment, the process is conducted at a temperature below the initial gelatinization temperature. Such processes are oftentimes conducted at least at 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or at least 60° C. The pH at which the process is conducted may in be in the range of about 3.0 to about 7.0, or from about 3.5 to about 6.0, or from about 4.0 to about 5.0. One aspect contemplates a process comprising fermentation, e.g. with a yeast to produce ethanol, e.g., at a temperature around 32° C., such as from 30° C. to 35° C.

In another aspect, the process comprises simultaneous saccharification and fermentation, e.g., with a yeast to produce ethanol, or another suitable fermentation organism to produce a desired organic compound, such as at a temperature from 30° C. to 35° C., e.g., at around 32° C.

In the above fermentation processes, the ethanol content reaches at least about 7%, at least about 8%, at least about 9%, at least about 10%, at least about 11%, at least about 12%, at least about 13%, at least about 14%, at least about 15% such as at least about 16% ethanol.

The starch slurry to be used in any of the above aspects may have about 20% to about 55% dry solids granular starch, about 25% to about 40% dry solids granular starch, or from about 30% to about 35% dry solids granular starch. After being contacted with a *Bacillus* sp. strain TS-23 α-amylase or a variant thereof, the enzyme converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, a *Bacillus* sp. strain TS-23 α-amylase or variant thereof comprises a catalytic module having α-amylase activity and a carbohydrate-binding module, e.g., the polypeptide of the first aspect, is used in a process for liquefaction, saccharification of a gelatinized starch, e.g., but not limited to gelatinization by jet cooking. The process may comprise fermentation to produce a fermentation product, e.g., ethanol. Such a process for producing ethanol from starch-containing material by fermentation comprises: (i) liquefying said starch-containing material with a polypeptide comprising a catalytic module having α-amylase activity and a carbohydrate-binding module, e.g., the polypeptide of the first aspect; (ii) saccharifying the liquefied mash obtained; and (iii) fermenting the material obtained in step (ii) in the presence of a fermenting organism. Optionally the process further comprises recovery of the ethanol. The saccharification and fermentation processes may be carried out as a simultaneous saccharification and fermentation process (SSF process). During the fermentation, the ethanol content reaches at least about 7%, at least about 8%, at least about 9%, at least about 10% such as at least about 11%, at least about 12%, at least about 13%, at least about 14%, at least 15% such as at least 16% ethanol.

The starch to be processed in the processes of the above aspects may in particular be obtained from tubers, roots, stems, legumes, cereals or whole grain. More specifically, the granular starch may be obtained from corns, cobs, wheat, barley, rye, milo, sago, cassava, tapioca, sorghum, rice, peas, bean, banana, or potatoes. Also contemplated are both waxy and non-waxy types of corn and barley.

The composition described above may be used for liquefying and/or saccharifying a gelatinized or a granular starch, and a partly gelatinized starch. A partly gelatinized starch is a starch that to some extent is gelatinized, i.e., wherein part of the starch has irreversibly swelled and gelatinized and part of the starch is still present in a granular state.

The composition described above may comprise an acid α-amylase variant present in an amount of 0.01 to 10.0 AFAU/g DS, or 0.1 to 5.0 AFAU/g DS, or 0.5 to 3.0 AFAU/ AGU, or 0.3 to 2.0 AFAU/g DS. The composition may be applied in any of the starch processes described above.

As used herein, the term "liquefaction" or "liquefy" means a process by which starch is converted to shorter chain and less viscous dextrins. Generally, this process involves gelatinization of starch simultaneously with or followed by the addition of a Bacillus sp. strain TS-23 α-amylase or a variant thereof. Additional liquefaction inducing enzymes may also be added.

As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from 200-300° F., e.g., 220-235° F. Subsequent to application to a heat exchange or jet temperature, the slurry is held for a period of 3-10 minutes at that temperature. This step of holding the slurry at 200-300° F. is primary liquefaction.

As used herein, the term "secondary liquefaction" refers the liquefaction step subsequent to primary liquefaction (heating to 200-300° F.), when the slurry is allowed to cool to atmospheric temperature. This cooling step can be 30 minutes to 180 minutes (3 hours), e.g. 90 minutes to 120 minutes (2 hours).

As used herein, the term "minutes of secondary liquefaction" refers to the time that has elapsed from the start of secondary liquefaction, to the time that the DE is measured.

Another aspect contemplates the additional use of a β-amylase in the composition comprising Bacillus sp. strain TS-23 α-amylase or variant thereof. β-amylases (EC 3.2.1.2) are exo-acting maltogenic amylases, which catalyze the hydrolysis of 1,4-α-glucosidic linkages in to amylose, amylopectin, and related glucose polymers, thereby releasing maltose.

β-amylases have been isolated from various plants and microorganisms (W. M. Fogarty and C. T. Kelly, PROGRESS IN INDUSTRIAL MICROBIOLOGY, Vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley Spezyme® BBA 1500, Spezyme® DBA, Optimalt® ME, Optimalt® BBA (Danisco US Inc., Genencor Division) and Novozym™ WBA (Novozymes A/S).

Another enzyme contemplated for use in the composition is a glucoamylase (EC 3.2.1.3). Glucoamylases are derived from a microorganism or a plant. Exemplary glucoamylases are of fungal or bacterial origin. Exemplary bacterial glucoamylases are Aspergillus glucoamylases, in particular A. niger G1 or G2 glucoamylase (Boel et al., EMBO J. 3(5): 1097-1102 (1984), or variants thereof, such as disclosed in WO 92/00381; and WO 00/04136; the A. awamori glucoamylase (WO 84/02921); A. oryzae (Agric. Biol. Chem., 55(4): 941-949 (1991)), or variants or fragments thereof.

Other contemplated Aspergillus glucoamylase variants include variants to enhance the thermal stability: G137A and G139A (Chen et al., Prot. Eng. 9: 499-505 (1996)); D257E and D293E/Q (Chen et al., Prot. Eng. 8: 575-582 (1995)); N182 (Chen et al., Biochem. J. 301: 275-281 (1994)); disulfide bonds, A246C (Fierobe et al., Biochemistry, 35: 8698-8704 (1996)); and introduction of Pro residues in positions A435 and S436 (Li et al., Protein Eng. 10: 1199-1204 (1997)). Other contemplated glucoamylases include and Talaromyces glucoamylases, in particular derived from Talaromyces emersonii (WO 99/28448), Talaromyces leycettanus (U.S. Pat. No. RE 32,153), Talaromyces duponti, Talaromyces thermophilus (U.S. Pat. No. 4,587,215). Bacterial glucoamylases contemplated include glucoamylases from the genus Clostridium, in particular C. thermoamylolyticum (EP 135138) and C. thermohydrosulfuricum (WO 86/01831). Exemplary glucoamylases include the glucoamylases derived from Aspergillus oryzae. Also contemplated are the commercial glucoamylases such as AMG 200L; AMG 300 L; SAN™ SUPER and AMG™ E (Novozymes); OPTIDEX®300 (Danisco US Inc., Genencor Division); AMIGASE® and AMIGASE® PLUS (DSM); G-ZYME® G900 (Enzyme Bio-Systems); G-ZYME® G990 ZR (A. niger glucoamylase and low protease content).

Glucoamylases may be added in an amount of 0.02-2.0 AGU/g DS, or 0.1-1.0 AGU/g DS, such as 0.2 AGU/g DS.

Additional enzymes and enzyme variants are also contemplated for inclusion in the composition. One or more α-amylases can be used in addition to a Bacillus sp. strain TS-23 α-amylase or variant thereof, or can further include other enzymes discussed herein.

Another enzyme that can optionally be added is a debranching enzyme, such as an isoamylase (EC 3.2.1.68) or a pullulanase (EC 3.2.1.41). Isoamylase hydrolyses α-1,6-D-glucosidic branch linkages in amylopectin and β-limit dextrins and can be distinguished from pullulanases by the inability of isoamylase to attack pullulan, and by the limited action on α-limit dextrins. Debranching enzymes may be added in effective amounts known in the art.

The exact composition of the products of the process depends on the combination of enzymes applied as well as the type of granular starch processed. For example, the soluble hydrolysate can be maltose with a purity of at least about 85%, at least about 90%, at least about 95.0%, at least about 95.5%, at least about 96.0%, at least about 96.5%, at least about 97.0%, at least about 97.5%, at least about 98.0%, at least about 98.5, at least about 99.0% or at least about 99.5%. Alternatively, the soluble starch hydrolysate can be glucose or the starch hydrolysate has a DX (glucose percent of total solubilized dry solids) of at least 94.5%, at least 95.0%, at least 95.5%, at least 96.0%, at least 96.5%, at least 97.0%, at least 97.5%, at least 98.0%, at least 98.5, at least 99.0% or at least 99.5%. The process can include a product which is a specialty syrup, such as a specialty syrup containing a mixture of glucose, maltose, DP3 and DPn for use in the manufacture of ice creams, cakes, candies, canned fruit.

Two milling processes are: wet and dry milling. In dry milling, the whole kernel is milled and used. Wet milling gives a good separation of germ and meal (starch granules and protein), and is with a few exceptions, applied at locations where the starch hydrolysate is used in production of syrups. Both dry and wet milling are well known in the art of starch processing and are equally contemplated for use with the compositions and methods disclosed. The process may be conducted in an ultrafiltration system where the retentate is held under recirculation in presence of enzymes, raw starch and water and where the permeate is the soluble starch hydrolysate. Equally contemplated is the process conducted in a continuous membrane reactor with ultrafiltration membranes and where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate In one regard, the soluble starch hydrolysate of the process is subjected to conversion into high fructose starch-based syrup (HFSS), such as high fructose corn syrup (HFCS). This conversion can be achieved using a glucose isomerase, and by an immobilized glucose isomerase supported on a solid support. Contemplated isomerases include the commercial products Sweetzyme®, IT (Novozymes A/S); G-zyme® IMGI, and G-zyme® G993, Ketomax™, G-zyme® G993 (Rhodia); G-zyme® G993 liquid, GenSweet® IGI (Danisco US Inc., Genencor Division).

In another aspect, the soluble starch hydrolysate produced by these methods can be used in the production of fuel or potable ethanol. In the process of the third aspect, the fermentation may be carried out simultaneously or separately/sequential to the hydrolysis of the granular starch slurry. When the fermentation is performed simultaneous to the hydrolysis, the temperature is between 30° C. and 35° C., or between 31° C. and 34° C. The process may be conducted in an ultrafiltration system where the retentate is held under recirculation in presence of enzymes, raw starch, yeast, yeast nutrients and water and where the permeate is an ethanol containing liquid. Equally contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta lactone, or sodium erythorbate.

The amylolytic activity of a *Bacillus* sp. strain TS-23 α-amylase or variant thereof may be determined using potato starch, for example, as a substrate. This method is based on the break-down of modified potato starch by the enzyme, and the reaction is followed by mixing samples of the starch/enzyme solution with an iodine solution. Initially, a blackish-blue color is formed, but during the break-down of the starch, the blue color gets weaker and gradually turns into a reddish-brown, which is compared to a colored glass standard.

4.5 Compositions and Methods for Baking and Food Preparation

For the commercial and home use of flour for baking and food production, it is important to maintain an appropriate level of α-amylase activity in the flour. A level of activity that is too high may result in a product that is sticky and/or doughy and unmarketable; but flour with insufficient α-amylase activity may not contain enough sugar for proper yeast function, resulting in dry, crumbly bread. To augment the level of endogenous α-amylase activity in flour, an α-amylase may be added to flour in the form of a *Bacillus* sp. strain TS-23 α-amylase or variant thereof. Therefore, the ability to determine the level of activity of both endogenous (natural) and fungal α-amylase, or other α-amylase, in a flour sample would benefit the food production process and promote more efficient use of flour in food production.

In addition to the use of grains and other plant products in baking, grains such as barley, oats, wheat, as well as plant components such as corn, hops, and rice are used for brewing, both in industry and for home brewing. The components used in brewing may be unmalted or malted, which means partially germinated resulting in an increase in the levels of enzymes including α-amylase. For successful brewing, adequate levels of α-amylase enzyme activity are necessary to ensure the appropriate levels of sugars for fermentation.

As used herein, the term "flour" means milled or ground cereal grain. The term "flour" may also mean Sago or tuber products that have been ground or mashed. In some embodiments, flour may also contain components in addition to the milled or mashed cereal or plant matter. An example of an additional component, although not intended to be limiting, is a leavening agent. Cereal grains include but are not limited to: wheat, oat, rye, and barley. Tuber products can include tapioca flour, cassava flour, and custard powder. The term "flour" also includes ground corn flour, maize-meal, rice flour, whole-meal flour, self-rising flour, tapioca flour, cassava flour, ground rice, enriched flour, and custard powder.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in flours, and also in stock, which includes the aforementioned types of grains, tubers, and other plant products that have been crushed.

Also disclosed are methods for measuring α-amylase activity in flour and grain or tuber products and stock. As used herein, the term "α-amylase" means endogenous α-amylase (present in the flour or stock) or a *Bacillus* sp. strain TS-23 α-amylase or variant thereof that has been added to the flour or stock.

A *Bacillus* sp. strain TS-23 α-amylase or variant thereof alone or in a combination with other amylases can be added to prevent staling. The anti-staling amylases used may be any amylase that is effective in retarding the staling (crumb firming) of baked products.

The amylase can have a temperature optimum in the presence of starch in the ranges for example of 30-90° C., 50-80° C., 55-75° C., 60-70° C. The temperature optimum may be measured in a 1% solution of soluble starch at pH 5.5.

Additional anti-staling amylases that can be used in combination with a *Bacillus* sp. strain TS-23 α-amylase include an endo-amylase, e.g., a bacterial endo-amylase from *Bacillus*. For example, the additional amylase can be a maltogenic alpha-amylase (EC 3.2.1.133), e.g. from *Bacillus*. Novamyl® is a maltogenic alpha-amylase from *B. stearothermophilus* strain NCIB 11837 and is described in, e.g., C. Christophersen et al., 1997 *Starch* 50(1): 39-45.

Other examples of anti-staling endo-amylases can include other bacterial alpha-amylases, derived e.g. from *Bacillus*, such as *B. licheniformis* or *B. amyloliquefaciens*.

The anti-staling amylase may be an exo-amylase such as β-amylase, e.g. from plant (e.g., soybean) or from microbial sources (e.g., *Bacillus*).

The α-amylase of *Bacillus* sp. strain TS-23 or variant thereof can be added alone or with other amylases in an amount effective for retarding the staling (crumb firming) of the baked product. The amount of anti-staling amylase will typically be in the range of 0.01-10 mg of enzyme protein per kg of flour, e.g. 1-10 mg/kg.

The baking composition comprising an α-amylase of *Bacillus* sp. strain TS-23 can further comprise a phospholipase. The phospholipase may have $A_1$ or $A_2$ activity to remove fatty acid from the phospholipid and form a lyso-phospholipid. It may or may not have lipase activity, i.e. activity on triglycerides. The phospholipase can have a temperature optimum in the range of 30-90° C., e.g. 30-70° C. The added phospholipases can be of animal origin, e.g. from pancreas (e.g., bovine or porcine pancreas), snake venom or bee venom. Alternatively, the phospholipase may be of microbial origin, e.g. from filamentous fungi, yeast or bacteria, such as the genus or species *Aspergillus, A. niger; Dictyostelium, D. discoideum; Mucor, M. javanicus, M. mucedo, M. subtilissimus; Neurospora, N. crassa; Rhizomucor, R. pusillus; Rhizopus, R. arrhizus, R. japonicus, R. stolonifer; Sclerotinia, S. libertiana; Trichophyton, T. rubrum; Whetzelinia, W. sclerotiorum; Bacillus, B. megaterium, B. subtilis; Citrobacter, C. freundii; Enterobacter, E. aerogenes, E. cloacae; Edwardsiella, E. tarda; Erwinia, E. herbicola; Escherichia, E. coli; Klebsiella, K. pneumoniae; Proteus, P. vulgaris; Providencia, P. stuartii; Salmonella, S. typhimurium; Serratia, S. liquefasciens, S. marcescens; Shigella, S. flexneri; Streptomyces, S. violeceoruber; Yersinia, Y. enterocolitica; Fusarium*, and *F. oxysporum* (e.g., strain DSM 2672).

The phospholipase is added in an amount that improves the softness of the bread during the initial period after baking, particularly the first 24 hours. The amount of phospholipase will typically be in the range of about 0.01-10 mg of enzyme protein per kg of flour (e.g. 0.1-5 mg/kg) or 200-5000 LEU/kg of flour (e.g. 500-2000 LEU/kg). A phospholipase with lipase activity is generally added in an amount corresponding to a lipase activity of about 20-1000 LU/kg of flour, particularly 50-500 LU/kg. One LU (Lipase Unit) is defined as the amount of enzyme required to release 1 µmol butyric acid per minute at 30.0° C.; pH 7.0; with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked.

The dough is normally a leavened dough or a dough to be subjected to leavening. The dough may be leavened in various ways, such as by adding chemical leavening agents, e.g., sodium bicarbonate or by adding a leaven (fermenting dough). For example, the dough can be leavened by adding a suitable yeast culture, such as a culture of *Saccharomyces cerevisiae* (baker's yeast), e.g. a commercially available strain of *S. cerevisiae*.

The dough may also comprise other conventional dough ingredients, e.g., proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin, but is applicable to a dough which is made without addition of emulsifiers (other than optionally phospholipid).

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a hemicellulase, in particular a pentosanase such as xylanase, a protease, a protein disulfide isomerase, e.g., a protein disulfide isomerase as disclosed in WO 95/00636, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipoxygenase, an L-amino acid oxidase or a carbohydrate oxidase.

The additional enzyme may be of any origin, including mammalian and plant origin, and as well as of microbial (bacterial, yeast or fungal) origin and may be obtained by techniques conventionally used in the art.

The xylanase can be microbial origin, e.g. derived from a bacterium or fungus, such as a strain of *Aspergillus*, in particular of *A. aculeatus, A. niger* (cf. WO 91/19782), *A. awamori* (WO 91/18977), or *A. tubigensis* (WO 92/01793); from a strain of *Trichoderma*, e.g. *T. reesei*, or from a strain of *Humicola*, e.g. *H. insolens* (WO 92/17573). Pentopan® and Novozym 384® are commercially available xylanase preparations produced from *Trichoderma reesei*.

The amyloglucosidase may be an *A. niger* amyloglucosidase (such as AMG®). Other useful amylase products include Grindamyl® A 1000 or A 5000 (available from Grindsted Products, Denmark) and Amylase® H or Amylase® P (available from DSM Gist Brocades, The Netherlands).

The glucose oxidase may be a fungal glucose oxidase, in particular an *Aspergillus niger* glucose oxidase (such as Gluzyme®).

Exemplary proteases are Neutrase® (Novozymes) and Protex OxG (Danisco US Inc., Genencor Division).

Exemplary lipase can be derived from strains of *Thermomyces (Humicola), Rhizomucor, Candida, Aspergillus, Rhizopus*, or *Pseudomonas*, in particular from *Thermomyces lanuginosus (Humicola lanuginosa), Rhizomucor miehei, Candida antarctica, Aspergillus niger, Rhizopus delemar* or *Rhizopus arrhizus* or *Pseudomonas cepacia*. In specific embodiments, the lipase may be Lipase A or Lipase B derived from *Candida antarctica* as described in WO 88/02775, or the lipase may be derived from *Rhizomucor miehei* as described in EP 238,023, or *Humicola lanuginosa* described in EP 305,216, or *Pseudomonas cepacia* as described in EP 214, 761 and WO 89/01032.

The process may be used for any kind of baked product prepared from dough, either of a soft or a crisp character of a white, light, or dark type. Examples are bread (in particular white, whole-meal or rye bread), typically in the form of loaves or rolls, French baguette-type bread, pita bread, tortillas, cakes, pancakes, biscuits, cookies, pie crusts, crisp bread, steamed bread, pizza and the like.

Another aspect contemplates the use of the *Bacillus* sp. strain TS-23 α-amylase or variant thereof in a pre-mix comprising flour together with an anti-staling amylase, a phospholipase and a phospholipid. The pre-mix may contain other dough-improving and/or bread-improving additives, e.g. any of the additives, including enzymes, mentioned above.

Another aspect provided is an enzyme preparation comprising an anti-staling amylase and a phospholipase, for use as a baking additive. The enzyme preparation can be in the form of a granulate or agglomerated powder. It can have a narrow particle size distribution with more than 95% (by weight) of the particles in the range from 25 to 500 µm.

Granulates and agglomerated powders may be prepared by conventional methods, e.g. by spraying the amylase onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy.

Another aspect contemplates the enveloping of a *Bacillus* sp. strain TS-23 α-amylase. To prepare the enveloped alpha-amylase particles, the enzymes are contacted with a food grade lipid, discussed in further detail below, in sufficient quantity to suspend all of the alpha-amylase particles.

Food grade lipids, as used herein, may be any naturally organic compound that is insoluble in water but is soluble in non-polar organic solvents such as hydrocarbon or diethyl ether. The food grade lipids utilized can include, but are not limited to, triglycerides either in the form of fats or oils that are either saturated or unsaturated. Examples of fatty acids and combinations thereof which make up the saturated triglycerides utilized include, but are not limited to, butyric (derived from milk fat), palmitic (derived from animal and plant fat), and/or stearic (derived from animal and plant fat). Examples of fatty acids and combinations thereof which make up the unsaturated triglycerides utilized include, but are not limited to, palmitoleic (derived from animal and plant fat), oleic (derived from animal and plant fat), linoleic (derived from plant oils), and/or linolenic (derived from linseed oil). Other food grade lipids contemplated and within the scope include, but are not limited to, monoglycerides and diglycerides derived from the triglycerides discussed above, phospholipids and glycolipids.

The food grade lipid, in the liquid form, is contacted with a powdered form of the alpha-amylase particles in such a fashion that the lipid material covers at least a portion of the surface of at least a majority, and for example 100% of the α-amylase particles. Thus, each alpha-amylase particle is individually enveloped in a lipid. For example, all or substantially all of the particles of α-amylase are provided with a thin, continuous, enveloping film of lipid. This can be accomplished by first pouring a quantity of lipid into a container, and then slurrying the α-amylase so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase is incorporated into the dough, the baker continues through the normal production process for that product.

The advantages of enveloping the α-amylase are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle (i.e., the lipid-enveloped enzyme) is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped alpha-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary in order to provide the baker with some insurance against inadvertent under-measurement errors by the baker. The lower limit of enzyme concentration is determined by the minimum anti-staling effect the baker wishes to achieve.

A typical method of preparing a baked good according to the method comprises: a) preparing lipid-coated alpha-amylase particles, wherein substantially 100 percent of the α-amylase particles are coated; b) mixing a dough containing flour; c) adding the lipid-coated α-amylase to the dough before the mixing is complete and terminating the mixing before the lipid coating is removed from the α-amylase; d) proofing the dough; and e) baking the dough to provide the baked good, wherein the α-amylase is inactive during the mixing, proofing and baking stages and is active in the baked good.

Thus, the enveloped α-amylase can be added to the dough near the end of the mix cycle. A feature of the method is that the enveloped α-amylase is added at a point in the mixing stage that allows sufficient distribution of the enveloped α-amylase though out the dough, however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, there are several variables that may determine the precise procedure. First, the quantity of enveloped α-amylase must have a total volume sufficient to allow the enveloped α-amylase to be spread throughout the dough mix. If the preparation of enveloped alpha-amylase is highly concentrated, additional oil may need to be added to the pre-mix before the enveloped α-amylase is added to the dough. Recipes and production processes may require specific modifications. However, good results generally can be achieved when 25% of the oil specified in a bread dough formula is held out of the dough and is used as a carrier for a concentrated enveloped alpha-amylase when added near the end of the mix cycle. In bread or other baked goods, recipes which have extremely low fat content (such as French-style breads), it has been found that an enveloped α-amylase mixture of approximately 1% of the dry flour weight is sufficient to properly admix the enveloped α-amylase with the dough, but the range of percentages that may work is extremely wide and is dependent on the formula, finished product, and production methodology requirements of the individual baker rather than upon any known limitations. Second, the enveloped α-amylase suspension must be added to the mix with enough time remaining in the mix cycle for complete mixture into the dough, but not so early that excessive mechanical action will strip the protective lipid coating from a large proportion of the enveloped α-amylase particles.

In another embodiment, bacterial α-amylase (BAA) is added to the lipid-coated enzyme particles. BAA is known to reduce bread to a gummy mass due to its excessive thermostability and retained activity in the fully baked loaf of bread. However, it has been found that when BAA is incorporated into the protected enzyme product, substantial additional anti-staling protection is obtained, even at very low BAA dosage levels. For example, BAA dosages of 150 RAU (Reference Amylase Units) per 100 pounds of flour have been found to be effective. In one aspect, between about 50 to 2000 RAU of BAA is added to the lipid-coated enzyme product. This low BAA dosage level, combined with the ability of the protective coating to keep enzyme in the fully-baked loaf from free contact with the starches, (except when water vapor randomly releases the enzyme from its coating) helps to achieve very high levels of anti-staling activity without the negative side-effects of BAA.

5. Methods

5.1 Filter Screening Assays

The assays discussed below may be used in the screening of AmyTS23 alpha-amylase variants having altered stability at high or low pH and/or under $Ca^{2+}$ depleted conditions compared to the parent alpha-amylase enzyme.

5.2 High pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with 10 micro g/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6-10.6 and incubated at room temperature (can be altered from 10-60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6-10.6. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

5.3 Low Calcium Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with a relevant antibiotic, e.g., kanamycin or chloramphenicol, at 37° C. for at least 21 hours. The cellulose-acetate layer is located on the TY agar plate.

Each filter sandwich is specifically marked with a needle after plating, but before incubation in order to be able to localize positive variants on the filter and the nitrocellulose filter with bound variants is transferred to a container with carbonate/bicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5-10. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

5.4 Low pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dasseli Germany) on TY agar plates with 10 micro g/ml chloramphenicol at 37° C. for at least 21 hours. The cellulose acetate layer is located on the TY agar plate.

Each filter sandwich is specifically marked with a needle after plating, but before incubation in order to be able to localize positive variants on the filter, and the nitrocellulose filter with bound variants is transferred to a container with citrate buffer, pH 4.5 and incubated at 80° C. for 20 minutes (when screening for variants in the wild type backbone) or 85° C. for 60 minutes (when screening for variants of the parent alpha-amylase). The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are re-screened twice under the same conditions as the first screen.

5.5 Secondary Screening

Positive transformants after rescreening are picked from the storage plate and tested in a secondary plate assay. Positive transformants are grown for 22 hours at 37° C. in 5 mL LB+chloramphenicol. The *Bacillus* culture of each positive transformant and as a control a clone expressing the corresponding backbone are incubated in citrate buffer, pH 4.5 at 90° C. and samples are taken at 0, 10, 20, 30, 40, 60 and 80 minutes. A 3 μL sample is spotted on an assay plate. The assay plate is stained with 10% Lugol solution. Improved variants are seen as variants with higher residual activity (detected as halos on the assay plate) than the backbone. The improved variants are determined by nucleotide sequencing.

5.6 Stability Assay of Unpurified Variants

The stability of the variants may be assayed as follows: *Bacillus* cultures expressing the variants to be analyzed are grown for 21 hours at 37° C. in 10 ml LB+chloramphenicol.

800 μL culture is mixed with 200 μL citrate buffer, pH 4.5. A number of 70 μL aliquots corresponding to the number of sample time points are made in PCR tubes and incubated at 70° C. or 90° C. for various time points (typically 5, 10, 15, 20, 25 and 30 minutes) in a PCR machine. The 0 min sample is not incubated at high temperature. Activity in the sample is measured by transferring 20 μL to 200 μL of the alpha-amylase PNP-$G_7$ substrate MPR3 ((Boehringer Mannheim Cat. no. 1660730) as described below under "Assays for Alpha-Amylase Activity". Results are plotted as percentage activity (relative to the 0 time point) versus time, or stated as percentage residual activity after incubation for a certain period of time.

5.7 Fermentation and Purification of Alpha-Amylase Variants

A *B. subtilis* strain harboring the relevant expression plasmid may be fermented and purified as follows: The strain is streaked on a LB-agar plate with 10 micro g/ml kanamycin from −80° C. stock, and grown overnight at 37° C. The colonies are transferred to 100 ml PS-1 media supplemented with 10 micro g/ml chloramphinicol in a 500 ml shaking flask.

| Composition of PS-1 medium | |
|---|---|
| Pearl sugar | 100 g/l |
| Soy Bean Meal | 40 g/l |
| $Na_2HPO_4, 12H_2O$ | 10 g/l |
| Pluronic ™ PE 6100 | 0.1 g/l |
| $CaCO_3$ | 5 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F.F. and elution is carried out by step elution with 0.2M NaCl in the same buffer. The eluate is dialysed against 10 mM Tris, pH 9.0 and applied on a Q-sepharose F.F. and eluted with a linear gradient from 0-0.3M NaCl over 6 column volumes. The fractions that contain the activity (measured by the Phadebas assay) are pooled, pH was adjusted to pH 7.5 and remaining color was removed by a treatment with 0.5% W/vol. active charcoal in 5 minutes.

5.8 Specific Activity Determination

The specific activity is determined using the Phadebas® assay (Pharmacia) as activity/mg enzyme. The manufacturers instructions are followed (see also below under "Assay for Alpha-Amylase Activity").

5.9 Determination of Isoelectric Point

The pI is determined by isoelectric focusing (ex: Pharmacia, Ampholine, pH 3.5-9.3).

5.10 Accelerated Stability Assay

In 50 ml Propylene tubes, 10 ml of detergent of interest was added. Appropriate dilution was made to both AmyTS23t and AmyTS23tΔRS so that 180 ppm of each was measured with a pippette into separate tubes containing the detergent. The detergent with each mutant enzyme was vortex for 30 sec and then placed on a RotaMix (ATR RKVS Model) for 10 minutes. 100 micro-liters of the detergent with the mutant enzyme were measured with a pipette and diluted 1:651. The initial activity of the mutants was assayed using Blocked P-Nitro-Phenyl-Maltoheptaose (Blocked PBNPG7) substrate on a Konelab, Model 20XT. The detergent samples were then incubated in a constant temperature incubator set at 37° C. Samples were removed at 1, 2, 4, 7 and 17 days and the enzyme activity assayed.

5.11 Assays for Alpha-Amylase Activity

5.11.1 Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric add, 50 mM boric acid, 0.1 mM $CaCl_2$, pH adjusted to the value of interest with NaOH). The test is performed in a water bath at the temperature of interest. The alpha-amylase to be tested is diluted in X ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must substrate and alpha-glucosidase are manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring a 20 microliter sample to a 96 well microtitre plate and incubating at 25° C. 200 microliter reagent solution pre-equilibrated to 25° C. is added. The solution is mixed and pre-incubated 1 minute and absorption is measured every 30 seconds over 4 minutes at OD 405 nm in an ELISA reader.

The slope of the time dependent absorption-curve is directly proportional to the activity of the alpha-amylase in question under the given set of conditions.

5.12 Determination of Enzyme Performance in Detergent Compositions

5.12.1 US Laundry Conditions

Use of Terg-o-tometer, United States Testing, Hoboken, N.J.—To simulate washing test under US washing conditions, a dose efficiency curve (DEC) of the mutant enzyme of interest was conducted at 20° C. using standard detergents such as Liquid AATCC 2003 Without Optical Brightener and/or Powder AATCC 1993 (American Association of Textile Chemists and Colorists). A corresponding DEC of a comparative alpha-amylase was then conducted to compare the stain removal performance of the inventive mutant enzyme. This process was repeated at 40° C. Typically, 4 swatches of CS-28 Rice Starch stain (CFT of Holland) were placed in a steel container of the Terg-o-tometer, which was filled with 1 Liter of DI water and 1.5 g of Liquid AATCC. When Powder AATCC was used, 1.5 g of the detergent powder was weighed out on an analytical balance (Model PM4800, Mettler Instrument Corp., Highstown, N.J. 08520 and added to the Terg-o-tometer. Two replicates were run at the same time. Unless otherwise stated, the tests were carried out for 12 minutes and rinsed for 3 minutes. After washing, the swatches were air-dried and the reflectance of the test swatches was measured with a Chroma Meter Model CR-410 manufactured by Konica Minolta. The data collected were treated with appropriate statistical analysis.

5.12.2 European Laundry Conditions

Use of Launder-O-meter, manufactured by Atlas Company, Atlanta, Ga.—To simulate the washing test under European washing conditions, a dose efficiency curve (DEC) of the mutant enzyme of interest was conducted at 40° C. using standard European testing detergents, IEC A and IEC A with Bleach (TAED-Tetra-Acetyl-ethylene-diamine acetate) and Sodium Perborate. A corresponding DEC curve of a comparative mutant enzyme was then conducted to compare the stain removal performance of the inventive mutant enzyme. This process was repeated at higher wash temperature if desirable. Typically, 4 swatches of EMPA 161, Maize starch (EMPA, Switzerland) were placed in a steel container with 250 ml of DI water containing 6.8 g/L of the IEC A detergent or 8.0 g/L of the IEC A with Bleach detergent. Two replicates were run at the same time. Unless otherwise stated the tests were carried out for 45 minutes and rinsed for 5 minutes. After washing, the swatches were air-dried and the reflectance of the test swatches was measured with a Chroma Meter Model CR-410. The data collected were treated with appropriate statistical analysis.

5.12.3 Microswatch Method of Assessing Detergent Compositions

Numerous α-amylase cleaning assays exist. Exemplary description of testing cleaning includes the following.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single-hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The "smaller swatch" can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of either metal, plastic, glass, ceramic, or other suitable material that is coated with the soil substrate for use in testing cleaning compositions for materials other than textiles. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis. A further microscreening assay can be to deliver and secure a swatch, for example an indigo dyed denim, to a well of a multi-well plate, and add particles such as sand or larger particles such as for example garnet sieved to include particle 6 to 8, or 9 gauge, and agitate the plate so as to cause abrasion of the swatch by the added particles. This assay has found use in the assessment of cellulases in stone washing applications. The effectiveness of the enzyme can be judged by either color release (e.g., released indigo is dissolved in dimethylsulfoxide and absorbance at $A_{600}$ nm is measured) to the reaction buffer or by reflectance measurements of the abraded swatch.

When, for example, untreated BMI (blood/milk/ink) swatches are washed in detergent without bleach, a large portion of the ink is released even without the help of a protease. Adding a protease leads to a small increase in ink release, which can be hard to quantify over the large background. One aspect provides a treatment protocol that allows one to control the degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, *Textile Research Journal* 52(4): 280 286 (1982)). Other test swatches include but are not limited to blood/milk/ink (BMI) stain(s) on a cotton-containing fabric, a spinach stain on a cotton-containing fabric, or grass on a cotton-containing fabric, and chocolate/milk/soot on a cotton-containing fabric.

A BMI stain can be fixed to cotton with 0.0003% to 0.3% hydrogen peroxide. Other combinations include grass or spinach fixed with 0.001% to 1% glutaraldehyde, gelatin and Coomassie Brilliant Blue stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see e.g., Cayot and Tainturier, *Anal. Biochem.* 249: 184-200, 1997). However, if a detergent or an enzyme sample leads to the formation of unusually small peptide fragments (for example, from the presence of peptidases in the sample), then one will obtain a larger TNBS signal, i.e., more "noise".

Another means of measuring wash performance of blood/milk/ink or other stain that is based on ink release. Proteolysis of protein on the swatches leads to the release of ink particles that can be quantified by measuring the absorbance of the wash liquor. The absorbance can be measured at any wavelength between 350 and 800 nm. The wavelength is measured at 410 nm or 620 nm. The wash liquor can also be examined to determine the wash performance on stains containing grass, spinach, gelatin or Coomassie Brilliant Blue stain. Exemplary wavelengths for these stains include and 670 nm for spinach or grass and 620 nm for gelatin or Coomassie Brilliant Blue. For example, an aliquot of the wash liquor (typically 100 to 150 µL from a 96-well microplate, for example) is removed and placed in a cuvette or multiwell microplate. This is then placed in a spectrophotometer and the absorbance is read at an appropriate wavelength.

The system can also be used to determine an enhanced enzyme and/or detergent composition for dish washing, for example, using a blood/milk/ink stain on a suitable substrate such as cloth, plastic or ceramic.

In one aspect, the a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tested with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains. Additional blood/milk/ink assays and conditions are provided in U.S. Pat. No. 7,122,334 (Danisco US Inc., Genencor Division).

5.13 Determination of LAS Sensitivity

The variant is incubated with different concentrations of LAS (linear alkyl benzene sulphonate; Nansa 1169/P) for 10 minutes at 40° C.

The residual activity is determined using the Phadebas® assay method or the alternative method employing the PNP-$G_7$ substrate.

LAS is diluted in 0.1 M phosphate buffer pH 7.5.

The following concentrations are used: 500 ppm, 250 ppm, 100 ppm, 50 ppm, 25 ppm, and 10 ppm or no LAS.

The variant is diluted in the different LAS buffers to concentration of 0.01-5 mg/l in a total volume of 10 ml and incubated for 10 minutes in a temperature controlled water bath. The incubation is stopped by transferring a small aliquot into cold assay buffer. It is important that during activity measurement the LAS concentration is below 1 ppm, in order not to affect the activity measurement.

Then the residual activity is determined in duplicate using the above mentioned Phadebas® assay or alternative method.

The activity is measured after subtraction of the blank.

The activity with no LAS is 100%.

In order to further illustrate the embodiments and advantages thereof, the following specific examples are given with the understanding that they are being offered to further illustrate the present invention and should not be construed in any way as limiting to the claims.

EXAMPLES

In the disclosure and experimental section which follows, the following abbreviations apply: wt % (weight percent); ° C. (degrees Centigrade); $H_2O$ (water); $dH_2O$ or DI (deionized water); $dIH_2O$ (deionized water, Milli-Q filtration); g or gm (grams); µg (micrograms); mg (milligrams); kg (kilograms); µl and µL (microliters); mL and ml (milliliters); mm (millimeters); µm (micrometer); M (molar); mM (millimolar); µM (micromolar); U (units); MW (molecular weight); sec (seconds); min(s) (minute/minutes); hr(s) (hour/hours); DO (dissolved oxygen); W/V (weight to volume); W/W (weight to weight); V/V (volume to volume); Genencor (Danisco US Inc, Genencor Division, Palo Alto, Calif.); Ncm (Newton centimeter) and ETOH (ethanol). eq (equivalents); N (Normal); ds or DS (dry solids content).

Example 1

Expression of AmyTS23 in *B. subtilis*

To test expression of AmyTS23 full length, the synthetic DNA sequence depicted in FIG. 3 (made by Geneart, Regensburg, Germany) was cloned behind the LAT (*B. licheniformis* amylase) promoter and fused in frame to a sequence encoding the LAT signal peptide (FIG. 5) into vector pHPLT (see e.g. WO2005111203 and [Solingen et al. (2001) *Extremophiles* 5: 333-341]) and transformed into a 9 protease deleted *B. subtilis* strain (degU$^{Hy}$32,oppA,ΔspoII3501, amyE::xylRPxylA-comK-ermC, ΔaprE, ΔnprE, Δepr, ΔispA, Δbpr, Δvpr, ΔwprA, Δmpr-ybfJ, ΔnprB) (see US20050202535 A1). Neomycin (10 µg/ml) resistant transformants secrete AmyTS23 amylase as judged by halo formation on starch plates after iodine staining (see WO2005111203). One of these amylase positive transformants was selected and designated BG6006 (pHPLT-AmyTS23). Cultures of this strain were typically grown at 37 deg for 60 to 72 hours at 250 rpm in the following medium (per liter): 10 g Soytone, 75 g glucose, 7.2 g urea, 40 mM MOPS, 4 mM Tricine, 3 mM dibasic potassium phosphate, 21.4 mM KOH, 50 mM NaCl, 276 µM potassium sulfate, 528 µM magnesium chloride, 50 µM trisodium citrate dihydrate, 100 µM calcium chloride dihydrate, 14 µM ferrous sulfate heptahydrate, 5.9 µM manganese sulfate dihydrate, 5.7 µM zinc sulfate monohydrate, 2.9 µM cupric chloride dihydrate, 4.2 µM cobalt chloride hexahydrate, 4.5 µM sodium molybdate dihydrate. For a 1 L volume, all components except for Soytone were mixed in 500 mL, sterile filtered, and added to an equal part of 2× Soytone, which had been sterilized by autoclaving. Trace metals and citrate can be made up as a 100× or 1000× stock solutions. Buffers, potassium hydroxide, sodium chloride, potassium sulfate, and magnesium chloride and trace metals can be made up as a 10× stock solutions. After all components were mixed, the pH was adjusted to 7.3. Prior to use this medium was supplemented with 20 mM calcium chloride.

The culture expressed the amylase in two major forms. A high molecular weight form was observed at the 66 kDa marker on a 10% SDS-PAGE gel. A shorter form was observed at 55 kDa.

The high molecular weight component was isolated from the culture broth by treating 500 mL of the broth with 10 mL settled volume of β-cyclodextrin-sepharose affinity matrix resin, synthesized in-house by standard protocol from β-cyclodextrin (Sigma Aldrich Cat. No. c4767) and epoxy-activated-sepharose-6B (GE Healthcare, N.J. Cat. No. 17-0480-01), over night at 4° C. with gentle agitation, collecting the resin, and washing with 25 mM bis-Tris propane buffer (pH 8.5) containing 2 mM calcium chloride ($CaCl_2$). The high molecular weight enzyme was eluted by washing the resin with the same buffer supplemented with 50 mM β-cyclodextrin. Fractions were analyzed by SDS-PAGE and those containing enzyme were pooled and dialyzed to remove β-cyclodextrin. Enzyme protein concentration was estimated by gel densitometry with OxAm amylase (Genencor) serving as the protein standard.

Example 2

Expression of AmyTS23t in *B. subtilis*

To test expression of genetically truncated AmyTS23 (AmyTS23t) the synthetic DNA fragment depicted in FIG. 4 was cloned into pHPLT and transformed into the 9 protease deleted *B. subtilis* strain as described in Example 1. Neomycin resistant transformants secrete AmyTS23t amylase as judged by halo formation on starch plates after iodine staining. One of these amylase positive transformants was selected and designated BG6006(pME622.1). This strain was cultured to produce AmyTS23t amylase as described in Example 1. Culture supernatant was examined by SDS-PAGE, and shown to produce a product of the expected size of 55 kDa.

The amylase protein was partially purified by the addition of $NH_4SO_4$ to 500 mL of culture to a final concentration of 1 M. Next, 10 mL settled volume of Phenyl-sepharose resin was added and the mixture was gently agitated overnight at 4° C. The resin was collected and washed with 25 mM bis-Tris propane buffer (pH 8.5) containing 1 M $NH_4SO_4$ and 2 mM calcium chloride ($CaCl_2$). Enzyme activity was eluted in the same buffer without $NH_4SO_4$. Fractions were analyzed by SDS-PAGE and those containing enzyme were pooled and dialyzed to remove residual $NH_4SO_4$. Enzyme protein concentration was estimated by gel densitometry with OxAm amylase (Genencor) serving as the protein standard.

Example 3

AmyTS23 in a Cleaning Screening Assay

Figure 7:
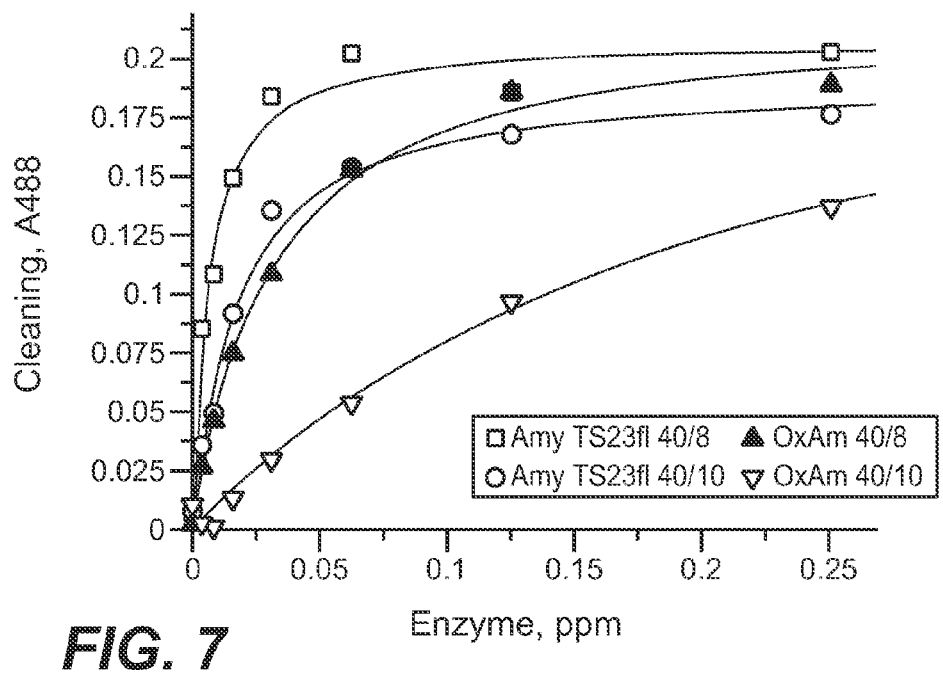
FIG. 7. Depicts results from a swatch cleaning assay using alpha-amylase AmyTS23Fl and OxAm control (Danisco US Inc., Genencor Division). Swatch was incubated in either 25 mM HEPES at pH 8 or 25 mM CAPS at pH 10.3 buffer; enzymes were added at the indicated level. The reaction was incubated 40° C. for 60 minutes with shaking at 750 rpm in an Eppendorf Thermomix controlled temperature block. The data indicates that amy TS23Fl performs better than the control (OxAm) at both pH values. Swatch cleaning was detected by an absorbance reading at 488 nm of the supernatant from the microswatch cleaning assay.

Partially purified AmyTS23 full length described in Example 1 (SEQ ID NO: 1) was analyzed in the 96-well CS28 orange-dyed rice starch soil fabric swatch micro applications cleaning assay. To conduct this assay, a 96-well plate is loaded with ¼ inch fabric swatches that are cut from fabric prewashed in room temperature water for 1 hour and air dried. This rinse removes a significant amount of loosely bound soil. Alternatively, the swatches have also been pre-washed after they were loaded into the plate. Both procedures give similar results. Buffer of choice is added to the wells of the plate and the plate is temperature equilibrated to a preferred temperature. In the present example, the assay was carried out in the 25 mM HEPES (pH 8.0) and in 25 mM CAPS (pH 10.3) buffers and incubation was at 40° C. After the equilibration period, enzyme is added to the desired concentration and incubation is continued for 30 minutes to 1 hour. Performance was judged by the amount of enzyme dependent color released into the solution. Color release was quantified spectrophotometrically at 488 nm. For additional information on the assay, see U.S. Pat. No. 7,122,334. Full length, mature was highly efficient in stain removal at pH 8.0, but also showed surprising stain removal at pH 10.3. Cleaning data for this enzyme in this assay are shown in FIG. 6 (20° C.) and FIG. 7 (40° C.). This swatch assay can be modified in several ways for different purposes. The 96-well assay is highly suitable as a high-throughput cleaning assay by measuring absorbance spectroscopically after incubation of enzyme with swatches, while for example, a 24-well plate with swatches, cut to fit in the wells can be used to wash larger swatches for which reflectance can be measured as known in the art. The two measurements, supernatant absorbance and swatch reflectance, showed nearly perfect correlation.

The correlation of reflectance of the washed swatch with the absorbance of supernatant was high; the coefficient of determination, $r^2$, had a value of 0.99. The assay can, in principle, be scaled to a 384-well plate. The assay can be carried out with any soiled swatch and in addition to the CS28 swatch, CS26, CS27, and CS29 swatches can be tested as well (e.g., corn starch, potato starch, tapioca starch, respectively; Testfabrics, Inc., West Pittiston, Pa.) to demonstrate the efficacy of the measurement as described in Example 3. The assay may also be used with detergent compositions and conducted at different temperatures and at different pH values. These assays were adapted from U.S. Pat. No. 7,122,334, which is incorporated herein in its entirety.

Example 4

Cleaning Screening Assay for AmyTS23t

Figure 8:
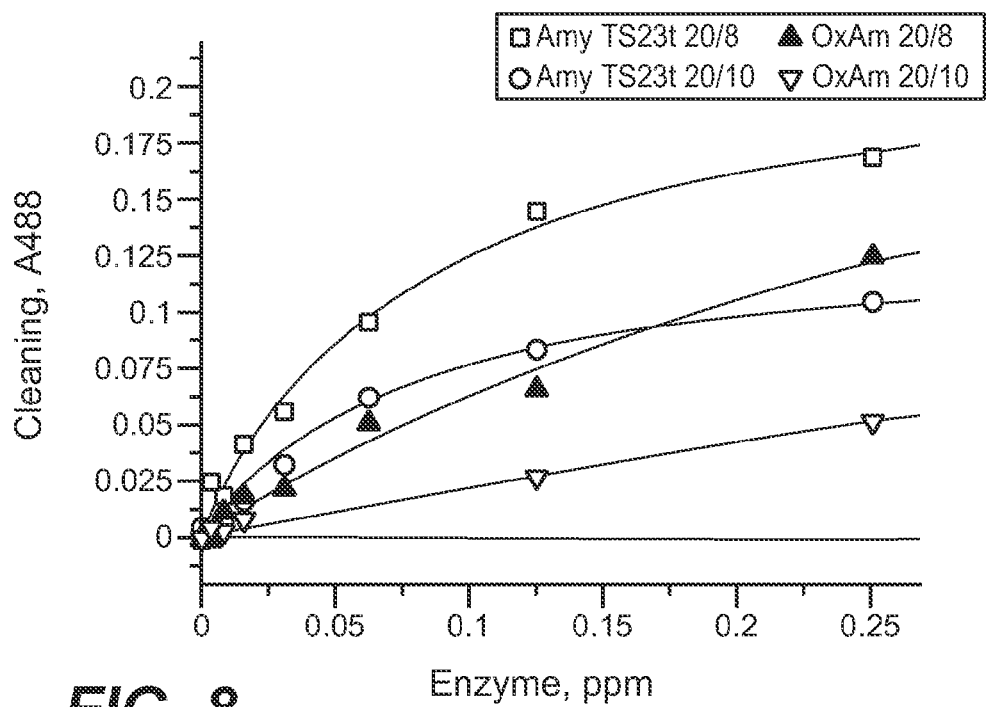
FIG. 8. Depicts results from a swatch cleaning assay with alpha-amylase AmyTS23t (SEQ ID NO: 2) and OxAm control. Swatch was incubated in either 25 mM HEPES at pH 8 or 25 mM CAPS at pH 10.3 buffer; enzymes were added at the indicated levels. The reaction was incubated 20° C. for 60 minutes with shaking at 750 rpm in an Eppendorf Thermomix controlled temperature block.
Figure 9:
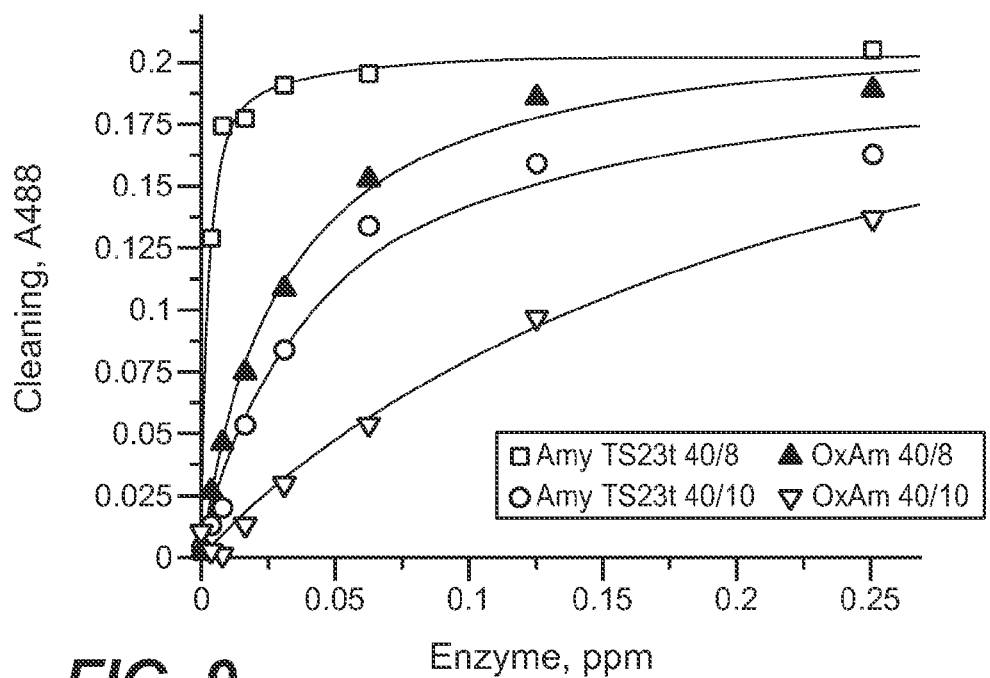
FIG. 9. Depicts a swatch cleaning assay with alpha-amylase Amy TS23t (SEQ ID NO: 2) and OxAm control (Danisco US Inc., Genencor Division). Swatches were incubated in either 25 mM HEPES at pH 8 or 25 mM CAPS at pH 10.3 buffer; enzymes were added at the indicated levels. The reaction was incubated 40° C. for 60 minutes with shaking at 750 rpm in an Eppendorf Thermomix controlled temperature block. The data indicates that alpha-amylase Amy TS23t (SEQ ID NO: 2) performs better than the control at both pH values. The truncated Amy TS23 alpha-amylase (SEQ ID NO: 2) is shown to perform better than full length mature Amy TS23.

Partially purified truncated AmyTS23 (AmyTS23t) described in Example 2 was analyzed in the 96-well CS28 orange dyed rice starch soil fabric swatch micro applications cleaning assay as described in Example 3. Cleaning data for this enzyme in this assay are shown in FIG. 8 (20° C.) and FIG. 9 (40° C.). The data indicates that AmyTS23t performs better than the control amylase (OxAm, commercial amylase obtainable from Genencor) at pH values 8.0 and 10.3. Comparison of FIGS. 6 and 8 clearly shows that the truncated AmyTS23 (SEQ ID NO: 2) performs better at 20° C. than does the AmyTS23 full length mature molecule (SEQ ID NO: 1).

Example 5

Expression of AmyTS23 Variants in *B. subtilis*

In this example, the construction of *Bacillus subtilis* strains expressing variants of AmyTS23t is described. Synthetic DNA fragment 056426 (produced by Geneart GmbH, Josef-Engert-strasse 11, D-93053 Regensburg, Germany), containing the codon optimized AmyTS23 gene (FIG. 3) served as template DNA. The pHPLT vector (Solingen et al., Extremophiles 5:333-341, 2001) which contains the *Bacillus licheniformis* alpha-amylase (LAT) promoter and the LAT signal peptide (pre LAT) followed by PstI and HpaI restriction sites for cloning, was used for expression of the AmyTS23t variants.

Three DNA fragments were produced by PCR using the DNA primers listed below:
1. AmyTS23t with CGG of codon 180 and AGC of codon 181 deleted (AmyTS23tΔRS)
2. AmyTS23t with ATG of codon 201 replaced by CTG (AmyTS23t(M201L))
3. AmyTS23t with both ATG of codon 201 replaced by CTG, and CGG of codon 180 and AGC of codon 181 deleted (AmyTS23t(M201L+ΔRS)

| Primer name | DNA sequence |
|---|---|
| pHPLT-PstI-FW SEQ ID NO: 8 | 5'-CTCATTCTGCAGCTTCAGCAAATACGGCG |
| pHPLT-HpaI-RV SEQ ID NO: 9 | 5'-CTCTGTTAACTCATTTGGCGACCCAGATT GAAACG |
| TS-deIRS-FW SEQ ID NO: 10 | 5'-CTATAAATTTACGGGCAAAGCATGGGATT GG |
| TS-deIRS-RV SEQ ID NO: 11 | 5'-TGCTTTGCCCGTAAATTTATAGATCCGGT TCAG |
| TS-M201L-FW SEQ ID NO: 12 | 5'-CTATGACTATCTGCTGTTTGCCGATCTG |
| TS-M201L-RV SEQ ID NO: 13 | 5'-CAGATCGGCAAACAGCAGATAGTCATAG |
| TS-deIRS/M201L-FW SEQ ID NO: 14 | 5'-GCATGGGATTGGGAAGTCGATACGGAAAA CGGCAACTATGACTATCTGCTGTTTGCCG |
| TS-deIRS/M201L-RV SEQ ID NO: 15 | 5'-CGTATCGACTTCCCAATCCCATGCTTTGC CCGTAAATTTATAGATCCGGTTC |

These DNA primers were synthesized and desalted by Sigma (Sigma-Aldrich Chemie B.V., Postbus 27,3330 AA Zwijndrecht, The Netherlands).

For all the PCR reactions described below, a final concentration of 0.2 µM DNA primer was used (forward and reverse primer), and 0.1-10 ng of DNA template was used (DNA fragment 056426 or pDNA pHPLT). In addition, all PCR reactions were completed in a volume of 50 µL, using Finnzymes (Finnzymes OY, Keilaranta 16 A, 02150 Espoo, Finland) Phusion High-Fidelity DNA Polymerase (Cat. no. F-530L). Also, all PCR reaction mixes contained 10 µL of 5× Phusion HF buffer, 1 µL of 10 mM dNTP mixture, 0.75 µL of Phusion DNA polymerase (2 units/µL), 1 µL of 100% DMSO and deionized, autoclaved water making up a final volume of 50 µL. The PCR programs, using a MJ Research PTC-200 Peltier thermal cycler (MJ Research, 590 Lincoln Street, Waltham, Mass. 02451, USA) were run as described by Finnzymes (protocol of manufacturer): 30 sec. at 98° C., 30× (10 sec. at 98° C., 20 sec. at 55° C., 22 sec./kb at 72° C.), 5 min. 72° C.

1. Generation of the AmyTS23tΔRS Variant: Two PCR reactions were performed using primers TS-delRS-FW and pHPLT-HpaI-RV on synthetic DNA fragment 056426, and primers TS-delRS-RV and pHPLT-PstI-FW on synthetic DNA fragment 056426. In order to fuse these two generated DNA fragments, 1 µL unpurified PCR mix from both reactions was added to a third PCR reaction sample in which primers pHPLT-PstI-FW and pHPLT-HpaI-RV were added.

The amplified linear 1.5 kb DNA fragment was purified (using Qiagen® Qiaquick PCR purification kit Cat. no. 28106) and digested with PstI and HpaI restriction enzymes. Subsequently, the AmyTS23tΔRS (also referred to herein as AmyTS23tΔRS) DNA fragment and pHPLT pDNA (50 ng/µl range, digested with PstI and HpaI zymes) were both purified (using Qiagen® Qiaquick PCR purification kit Cat. no. 28106) and then ligated at the PstI and HpaI ends. Reaction conditions are:

4 µL of purified and, PstI and HpaI digest of the AmyTS23tΔRS DNA fragment, 2 µL of purified and, PstI and HpaI digested pHPLT DNA fragment, 8 µL T4 DNA ligase buffer (Invitrogen® Cat. no. 46300-018), 25 µL distilled, autoclaved water and 1 µL T4 DNA ligase, 1 unit/µL (Invitrogen® Cat. no. 15224-017). Ligation reaction took place for 16-20 hours at 20° C.

Subsequently, the ligation mixture was transformed into a B. subtilis strain (ΔaprE, ΔnprE, Δepr, ΔispA, Δbpr) and (degU$^{Hy}$32, oppA, ΔspoIIE3501, amyE::xylRPxylAcomK-ermC, (Δvpr, ΔwprA, Δmpr-ybfJ, ΔnprB). Transformation into B. subtilis was performed as described in WO 02/14490. The B. subtilis transformants were selected on agar plates containing Heart infusion agar (Difco, Cat. No. 244400) and 10 mg/L neomycin. Selective growth of B. subtilis transformants harboring the pHPLT-AmyTS23tΔRS vector was performed in shake flasks as described in Example 1. This growth resulted in the production of secreted AmyTS23tΔRS amylase with starch hydrolyzing activity as visualized by spotting culture supernatant on a starch agar plate followed by iodine staining.

2. Generation of AmyTS23t(M201L): The same protocol was performed as described for the "Generation of AmyTS23tΔRS", except for the first two PCR reactions:

Two PCR reactions were performed using primers TS-M201L-FW and pHPLT-HpaI-RV on synthetic DNA fragment 056426, and primers TS-M201L-RV and pHPLT-PstI-FW on synthetic DNA fragment 056426.

3. Generation of AmyTS23t(M201L)-RSdelete: The same protocol was performed as described for the "Generation of AmyTS23tΔRS" discussed supra, except for the first two PCR reactions:

Two PCR reactions were performed using primers TS-delRS/M201L-FW and pHPLT-HpaI-RV on synthetic DNA fragment 056426, and primers TS-delRS/M201L-RV and pHPLT-PstI-FW on synthetic DNA fragment 056426.

Example 6

Improved Stability of AmyTS23tΔRS in Detergent

Figure 12:
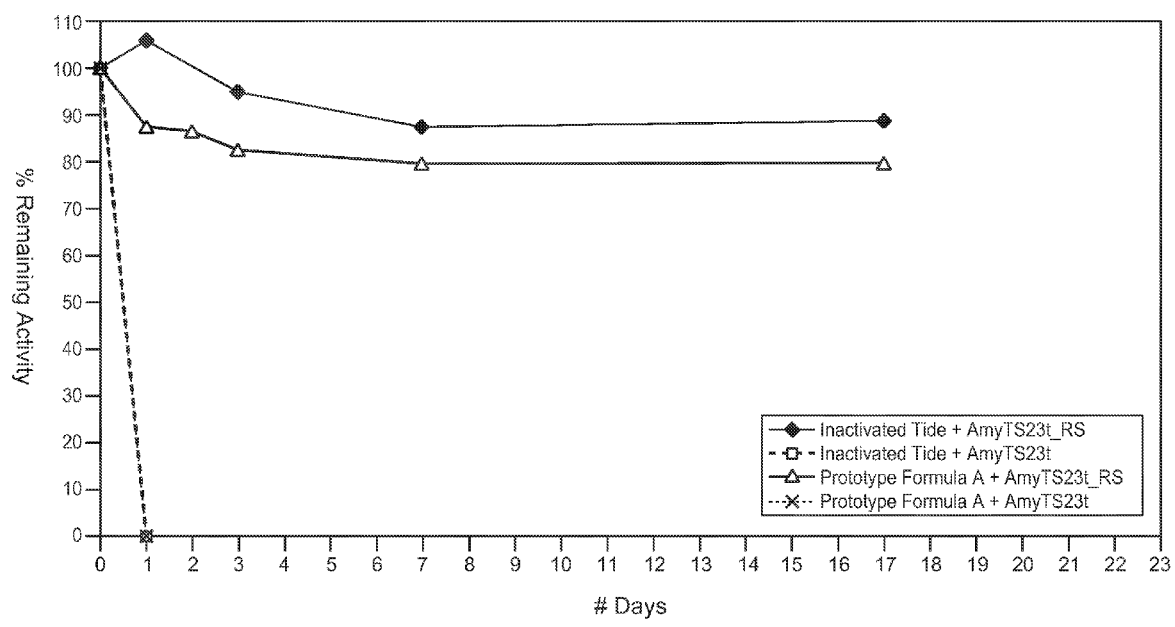
FIG. 12. Depicts a graph for an accelerated stability study with AmyTS23t (SEQ ID NO: 2) and AmyTS23tΔRS (SEQ ID NO: 5) in two different laundry detergent formulations. Enzyme samples were incubated at 37° C. in Inactivated Liquid Tide or Prototype Formula A liquid detergents and the remaining activity was determined over time in a Megazyme assay.

Stability of AmyTS23t and AmyTS23tΔRS was tested in an accelerated stability test at 37° C. in MOPS buffer, heat inactivated Tide (Procter & Gamble), and a prototype detergent (Prototype Formula A). The results are shown in FIG. 12. In the presence of either of the two detergent bases (Inactivated Tide or Prototype A detergent only) AmyTS23tΔRS (FIG. 10) is stable without any additional additives. As shown in FIG. 12, AmyTS23t lost the bulk of its activity after the first day and lost the activity completely after 2 days of accelerated testing at 37° C. AmyTS23tΔRS is stable under the same conditions and retained about 90% of original enzyme activity after 17 days. "STZ" as used in the table stands for STAINZYME.

TABLE 6-1

| | Percentage of Enzyme activity retained | | | | | |
|---|---|---|---|---|---|---|
| Treatment | Day 0 | Day 1 | Day 2 | Day 3 | Day 7 | Day 17 |
| Inactivated Tide + AmyTS23tΔRS | 100 | 106 | 89.5 | 94.8 | 87.5 | 88.9 |
| Inactivated Tide + AmyTS23t | 100 | 0 | | | | |

TABLE 6-1-continued

| Treatment | Percentage of Enzyme activity retained | | | | | |
|---|---|---|---|---|---|---|
| | Day 0 | Day 1 | Day 2 | Day 3 | Day 7 | Day 17 |
| Inactivated Tide + STZ | 100 | 100 | 99.1 | 100 | 96.5 | 88.3 |
| Prototype Formula A + AmyTS23tΔRS | 100 | 86.9 | 86.6 | 82.8 | 79.0 | 79.3 |
| Prototype Formula A + AmyTS23t | 100 | 0 | | | | |
| Prototype Formula A + STZ | 100 | 86.5 | 88.7 | 86.5 | 77.7 | 78.2 |

Prototype A detergent comprises the following:

| Ingredient | Supplier | DW-AA |
|---|---|---|
| Water, deionized (1) | | 46.4 parts |
| Borax (2) | | 1.6 |
| Boric acid | | 1.0 |
| Propylene glycol | | 10.0 |
| Ethanol, 70% (3) | | 7.0 |
| Hetoxol LA7 (4) | Global Seven | 6.72 |
| Hetoxol LA4 (4) | Global Seven | 1.28 |
| Nacconol 90G | Stepan | 10.0 |
| Steol CS370 | Stepan | 6.0 |
| Total | | 90.0 parts |

Other liquid formulations can be utilized in these examples, such as those exemplified below:
Premium HDL:

| | |
|---|---|
| Bio-Soft S-101 | linear alkylbenezene sulfonic acid |
| Steol CS-330 | sodium laureth sulfate |
| Bio-soft N25-7 | linear alkylethoxylate with 7 moles of EO |
| Staphanate SXS | sodium xylene sulfonate |

Ultra Liquid Detergent:

| | |
|---|---|
| Tionopal CBS-X | fluorescent whitening agent |
| Alpha-stem MC-48 | Sodium alpha-sulfomethylester |
| Makon TD-6 | Tridecylalcoholethoxylate |

Premium Heavy-Duty Liquid—with LAS/AES/AE—No NPE (Ingredients by % Weight):

| | |
|---|---|
| BIO-SOFT ® S101 | 6.43 |
| NaOH, 50% solution | 1.70 |
| STEOL ® CS-330 | 23.81 |
| BIO-SOFT ® N25-7 | 6.67 |
| STEPHANATE ® SXS | 7.50 |
| Sodium carbonate | 2.00 |
| Sodium chloride | 0.50 |
| Water, fragrance, dye, and preservative | q.s. to 100.00 |

Mix water, NaOH, and STEPHANATE® SXS. Slowly add BIO-SOFT® S101. Adjust pH with additional NaOH, if necessary. Continue mixing and add sodium carbonate. When sodium carbonate is dissolved, add STEOL® CS-330. Add BIO-SOFT® N25-7. Heat gently if necessary to completely solubilize BIO-SOFT® N25-7. Add remaining ingredients. Continue stirring until blend is well mixed.

Ultra Liquid Laundry Detergent (No. 465 of Stepan) (Ingredients by % by Weight):

| | |
|---|---|
| Water | 54.7 |
| Sodium hydroxide (50%) | 2.7 |
| BIO-SOFT ® S101 | 10.0 |
| Tinopal CBS-X (Ciba Geigy) | 0.2 |
| ALPHA-STEP ® MC-48 | 21.0 |
| MAKON ® 10 | 11.4 |
| Citric acid (25%) | q.s. |
| Preservative, dye & fragrance | q.s |
| TOTAL | 100.0 |

Charge the tank with water and sodium hydroxide. Add BIO-SOFT® S101 while mixing. Adjust pH to about 8.5 with sodium hydroxide or citric acid as required Add Tinopal CBS-X (an optical brightener) and dissolve. Add ALPHA-STEP® MC-48 and MAKON® 10—in that order. Mix until clear and uniform. Adjust pH to 8.0-9.0. Add preservative, dye and fragrance as desired.

Example 7

Oxidative Stability of AmyTS23 and AmyTS23 Mutants

Amylases vary in their response to exposure to peracetic acid (PAA). Thus, this example was designed to determine the oxidative stability of AmyTS23 and AmyTS23 mutant amylases.

Enzyme dilutions were prepared in 25 mM borate buffer, pH 8.64, 2 mM $Ca^{+2}$ by buffer exchange on 1 mL spin desalting columns (fabricated from tuberculin syringes from VWR filled with BioRad P-6 reside from BioRad). Peracetic acid contained in 5 μL volume was added to 25 μL of enzyme solution to yield 0 to 1 mM peracetic acid. The samples were incubated for 5 minutes at 40° C. in a PCR machine (DNA Engine, BioRad). The reaction was quenched using 25 mM BTP, pH 8.5. Residual amylase activity was measured using a standard amylase assay kit from Megazyme (Wicklow, Ireland).

Figure 13:
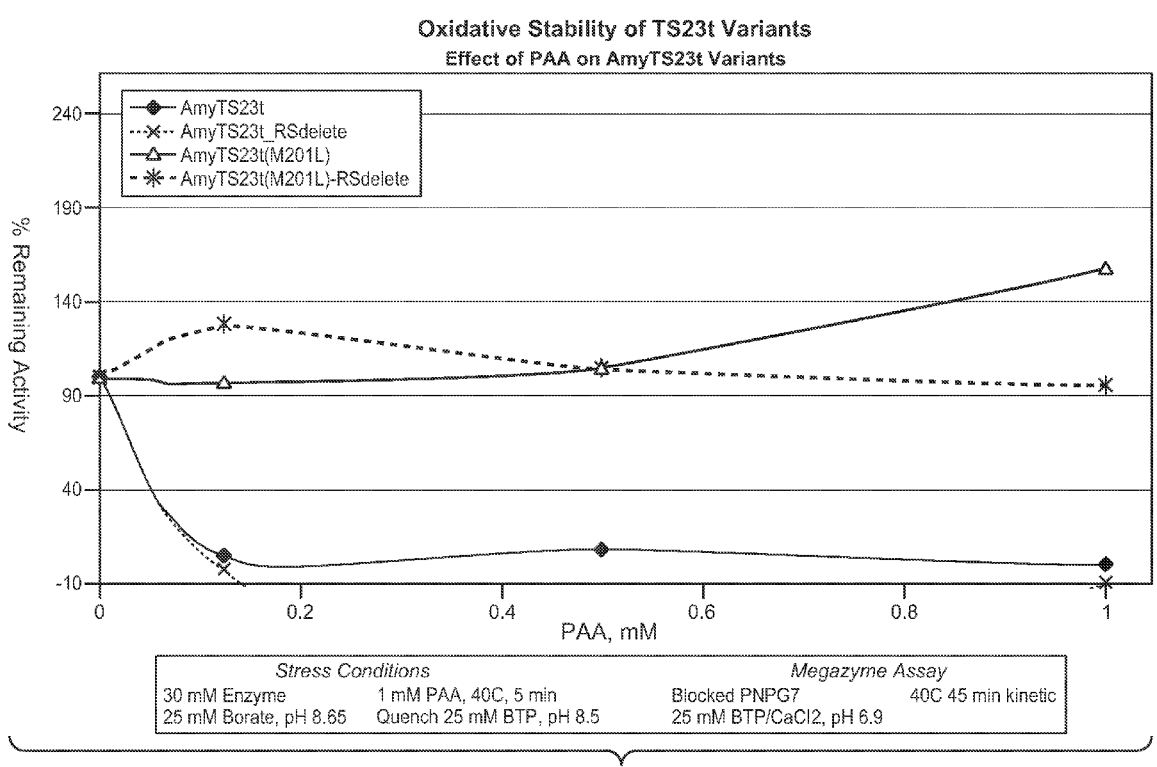
FIG. 13. The graph depicts the oxidative stability of AmyTS23t, AmyTS23tΔRS, and AmyTS23t(M201L+ΔRS). Enzyme activity was measured after the enzyme was exposed to various concentrations of peracetic acid (PAA) in $Ca^{+2}$ containing buffer at 40° C. for 5 minutes.

TS23t(M201L) has greater than 100% stability at low PAA concentration then decreases at higher concentrations. TS23t (M201L+ΔRS) has a 25% increase in stability at low PAA concentrations that dips to below 100%, finally maintaining oxidative stability at higher PAA concentrations. TS23t, TS23tΔRS, and Amy 707 are unstable in the presence of PAA decreasing in stability at low concentrations to baseline. See FIGS. 12-13.

Example 8

Cleaning Performance in Detergent

Figure 14:
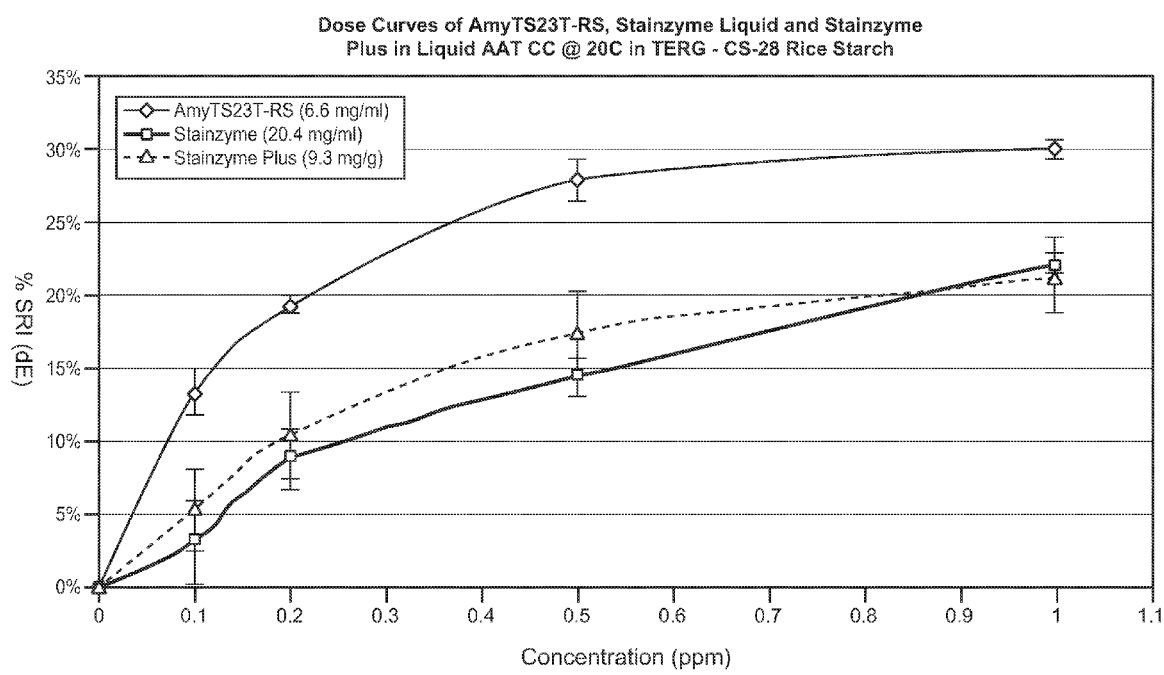
FIG. 14. The graph depicts the performance of the AmyTS23tΔRS (SEQ ID NO: 5) in liquid detergent on rice starch swatches.

A dose efficiency curve of selected concentrations of AmyTS23tΔRS was generated using the procedure described in Section 5.12.1 of this patent application. The performance evaluation was conducted both at 20° C. and 40° C. using a Tergotometer. The same conditions were used to generate dose efficiency curves for Stainzyme and Stainzyme Plus. As can be seen from the data (FIG. 14), AmyTS23tΔRS is significant superior to both Stainzyme products at 20° C. and moderately better at 40° C. This data supports the unique benefit of AmyTS23tΔRS as a unique high performing cold water enzyme.

Example 9

Amylase Production in B. subtilis

In this Example, production of Bacillus sp. TS-23t and variants thereof in B. subtilis are described. Transformation was performed as known in the art (see e.g., WO 02/14490). Briefly, the gene encoding the parent amylases was cloned into the pHPLT expression vector, which contains the LAT promoter (PLAT), a sequence encoding the LAT signal peptide (preLAT), followed by PstI and HpaI restriction sites for cloning.

The coding region for the LAT signal peptide is shown below:

(SEQ ID NO: 16)
atgaaacaacaaaaacggctttacgcccgattgctgacgctgttatttgc gctcatcttcttgctgcctcattctgcagcttcagca.

The amino acid sequence of the LAT signal peptide is shown below:

MKQQKRLYARLLTLLFALIFLLPHSAASA.      (SEQ ID NO: 17)

The coding region for the mature AmyTS-23t amylase is shown in FIG. 4.

The amino acid sequence of the mature AmyTS-23t alpha-amylase was used as the basis for making the variant libraries described herein is shown in FIG. 2 (SEQ ID NO: 2).

The PCR products were purified using Qiaquik columns from Qiagen, and resuspended in 50 μL of deionized water. 50 μL of the purified DNA was digested with HpaI (Roche) and PstI (Roche) and the resultant DNA resuspended in 30 μL of deionized water. 10-20 ng/μL of the DNA was cloned into plasmid pHPLT using PstI and HpaI cloning sites. The ligation mixtures were directly transformed into competent B. subtilis cells (genotype: Δvpr, ΔwprA, Δmpr-ybfJ, ΔnprB). The B. subtilis cells have a competency gene (i.e., comK), which is placed under a xylose inducible promoter, so xylose was used to induce competency for DNA binding and uptake (see Hahn et al., Mol. Microbiol., 21: 763-775, 1996).

The elements of plasmid pHPLT-AmyS include: pUB 110=DNA fragment from plasmid pUB110 (McKenzie et al., Plasmid 15: 93-103, 1986). Plasmid features include: ori-pUB110=origin of replication from pUB110; neo=neomycin resistance gene from pUB110; Plat=transcriptional promoter from B. licheniformis amylase; Pre-LAT=signal peptide from B. licheniformis amylase; SAMY 425ss=the coding region for truncated Amy TS-23 gene sequence (replaced by the coding regions for each truncated Amy TS-23 variant expressed in this study); and Terminator=transcriptional terminator from B. licheniformis amylase.

Amylase Expression—2 mL scale. B. subtilis clones containing AmyTS23t expression vectors were replicated with a steel 96-well replicator from glycerol stocks into 96-well culture plates (BD, 353075) containing 150 μL of LB media and 10 μg/ml neomycin, grown overnight at 37° C., 220 rpm in a humidified enclosure. A 100 μL aliquot from the overnight culture was used to inoculate 2000 μL defined media and 10 μg/mL neomycin in 5 mL plastic culture tubes. The cultivation media was an enriched semi-defined media based on MOPs buffer, with urea as major nitrogen source, glucose as the main carbon source, and supplemented with 1% soytone and 5 mM calcium for robust cell growth. Culture tubes were incubated at 37° C., 250 rpm, for 72 hours. Following this incubation, the culture broths were centrifuged for 10 minutes at 3000×g. The supernatant solution was decanted into 15 mL polypropylene conical tubes and 80 μL of each sample were aliquoted into 96 well plates for protein quantitation.

Generation of Bacillus sp. AmyTS23t Combinatorial Charge Library. Multiple protein variants spanning a range of a physical properties of interest are selected from existing libraries or are generated by site-directed mutagenesis techniques as known in the art (see e.g., U.S. patent application Ser. Nos., 10/576,331, 11/581,102, and 11/583,334). This defined set of probe proteins is then assayed in a test of interest.

AmyTS23t (SEQ ID NO: 2) is a truncated form of Bacillus sp. TS-23 alpha amylase (see Lin et al., 1998, Production and properties of a raw-starch-degrading amylase from the thermophilic and alkaliphilic Bacillus sp. TS-23, Biotechnol. Appl. Biochem. 28: 61-68). Expression of AmyTS23t in a multiple-protease deleted B. subtilis strain (degU$^{Hy}$32, oppA, ΔspoII3501, amyE::xylRPxylAcomK-ermC, ΔaprE, ΔnprE, Δepr, ΔispA, Δbpr, Δvpr, ΔwprA, Δmpr-ybfJ, ΔnprB) (see, e.g., US2005/0202535A1) was as shown in Examples 1 and 2. The AmyTS23t plasmid DNA isolated from transformed B. subtilis cells was sent to DNA2.0 Inc. (Menlo Park, Calif.) as the template for CCL construction. DNA 2.0 was requested to prepare a parent construct for the CCL by introducing the following seven mutations into AmyTS23t, which was consequently termed AmyTS23t-7mut: Q98R, M201L, S243Q, R309A, Q320R, Q359E, and K444E. Variants were supplied as glycerol stocks in 96-well plates. Subsequently a request was made to DNA2.0 Inc. for the generation of positional libraries at each of the four sites in AmyTS23t-7mut amylase that are shown in Table 9-1.

The AmyTS23t-7mut combinatorial charge library was designed by identifying the following four residues in AmyTS23t-7mut: Gln 87, Asn 225, Asn 272, and Asn 282. A four site, 81-member CCL was created by making all combinations of three possibilities at each site: wild-type, arginine, or aspartic acid.

TABLE 9-1

AmyTS23t-7mut CCL Variants

| Variant # | Q87 | N225 | N272 | N282 | Δ Charge |
|---|---|---|---|---|---|
| Parent 1 | — | — | — | — | 0 |
| 2 | Q87E | N225E | N272E | N282E | −4 |
| 3 | Q87E | N225E | N272E | N282R | −2 |
| 4 | Q87E | N225E | N272E | — | −3 |
| 5 | Q87E | N225E | N272R | N282E | −2 |
| 6 | Q87E | N225E | N272R | N282R | 0 |
| 7 | Q87E | N225E | N272R | — | −1 |
| 8 | Q87E | N225E | — | N282E | −3 |
| 9 | Q87E | N225E | — | N282R | −1 |
| 10 | Q87E | N225E | — | — | −2 |
| 11 | Q87E | N225R | N272E | N282E | −2 |
| 12 | Q87E | N225R | N272E | N282R | 0 |
| 13 | Q87E | N225R | N272E | — | −1 |
| 14 | Q87E | N225R | N272R | N282E | 0 |
| 15 | Q87E | N225R | N272R | N282R | +2 |
| 16 | Q87E | N225R | N272R | — | +1 |
| 17 | Q87E | N225R | — | N282E | −1 |
| 18 | Q87E | N225R | — | N282R | +1 |
| 19 | Q87E | N225R | — | — | 0 |
| 20 | Q87E | — | N272E | N282E | −3 |
| 21 | Q87E | — | N272E | N282R | −1 |

TABLE 9-1-continued

AmyTS23t-7mut CCL Variants

| Variant # | Q87 | N225 | N272 | N282 | Δ Charge |
|---|---|---|---|---|---|
| 22 | Q87E | — | N272E | — | −2 |
| 23 | Q87E | — | N272R | N282E | −1 |
| 24 | Q87E | — | N272R | N282R | +1 |
| 25 | Q87E | — | N272R | — | 0 |
| 26 | Q87E | — | — | N282E | −2 |
| 27 | Q87E | — | — | N282R | 0 |
| 28 | Q87E | — | — | — | −1 |
| 29 | Q87R | N225E | N272E | N282E | −2 |
| 30 | Q87R | N225E | N272E | N282R | 0 |
| 31 | Q87R | N225E | N272E | — | −1 |
| 32 | Q87R | N225E | N272R | N282E | 0 |
| 33 | Q87R | N225E | N272R | N282R | +2 |
| 34 | Q87R | N225E | N272R | — | +1 |
| 35 | Q87R | N225E | — | N282E | −1 |
| 36 | Q87R | N225E | — | N282R | +1 |
| 37 | Q87R | N225E | — | — | 0 |
| 38 | Q87R | N225R | N272E | N282E | 0 |
| 39 | Q87R | N225R | N272E | N282R | +2 |
| 40 | Q87R | N225R | N272E | — | +1 |
| 41 | Q87R | N225R | N272R | N282E | +2 |
| 42 | Q87R | N225R | N272R | N282R | +4 |
| 43 | Q87R | N225R | N272R | — | +3 |
| 44 | Q87R | N225R | — | N282E | +1 |
| 45 | Q87R | N225R | — | N282R | +3 |
| 46 | Q87R | N225R | — | — | +2 |
| 47 | Q87R | — | N272E | N282E | −1 |
| 48 | Q87R | — | N272E | N282R | +1 |
| 49 | Q87R | — | N272E | — | 0 |
| 50 | Q87R | — | N272R | N282E | +1 |
| 51 | Q87R | — | N272R | N282R | +3 |
| 52 | Q87R | — | N272R | — | +2 |
| 53 | Q87R | — | — | N282E | 0 |
| 54 | Q87R | — | — | N282R | +2 |
| 55 | Q87R | — | — | — | +1 |
| 56 | — | N225E | N272E | N282E | −3 |
| 57 | — | N225E | N272E | N282R | −1 |
| 58 | — | N225E | N272E | — | −2 |
| 59 | — | N225E | N272R | N282E | −1 |
| 60 | — | N225E | N272R | N282R | +1 |
| 61 | — | N225E | N272R | — | 0 |
| 62 | — | N225E | — | N282E | −2 |
| 63 | — | N225E | — | N282R | 0 |
| 64 | — | N225E | — | — | −1 |
| 65 | — | N225R | N272E | N282E | −1 |
| 66 | — | N225R | N272E | N282R | +1 |
| 67 | — | N225R | N272E | — | 0 |
| 68 | — | N225R | N272R | N282E | +1 |
| 69 | — | N225R | N272R | N282R | +3 |
| 70 | — | N225R | N272R | — | +2 |
| 71 | — | N225R | — | N282E | 0 |
| 72 | — | N225R | — | N282R | +2 |
| 73 | — | N225R | — | — | +1 |
| 74 | — | — | N272E | N282E | −2 |
| 75 | — | — | N272E | N282R | 0 |
| 76 | — | — | N272E | — | −1 |
| 77 | — | — | N272R | N282E | 0 |
| 78 | — | — | N272R | N282R | +2 |
| 79 | — | — | N272R | — | +1 |
| 80 | — | — | — | N282E | −1 |
| 81 | — | — | — | N282R | +1 |

Example 10

Performance Index

Rice Microswatch Assay. Test detergents were prepared as described elsewhere herein. The equipment used included a New Brunswick Innova 4230 shaker/incubator and a SpectraMAX (type 340) microtiter plate (MTP) reader. The MTPs were obtained from Corning (type 3641). Aged rice starch with orange pigment swatches (CS-28) were obtained from Center for Test Materials (Vlaardingen, Netherlands). Before cutting 0.25-inch circular microswatches, the fabric was washed with water. Two microswatches were placed in each well of a 96-well microtiter plate. The test detergent was equilibrated at 20° C. (North American) or 40° C. (Western Europe). 190 µL of detergent solution was added to each well of the MTP, containing microswatches. To this mixture, 10 µL of the diluted enzyme solution was added. The MTP was sealed with adhesive foil and placed in the incubator for 1 hour with agitation at 750 rpm at the desired test temperature (typically 20° C. or 40° C.). Following incubation, 150 µL of the solution from each well was transferred into a fresh MTP. This MTP was read at 488 nm using a SpectraMax MTP reader to quantify cleaning. Blank controls, as well as controls containing microswatches and detergent but no enzyme were also included.

Detergent Heat Inactivation. Heat inactivation of commercial detergent formulas serves to destroy the enzymatic activity of any protein components while retaining the properties of non-enzymatic components. Thus, this method was suitable for preparing commercially purchased detergents for use in testing the enzyme variants. For North American (NA) and Western European (WE) heavy duty liquid laundry (HDL) detergents, heat inactivation was performed by placing pre-weighed liquid detergent (in a glass bottle) in a water bath at 95° C. for 2 hours. The incubation time for heat inactivation of North American (NA) and Japanese (JPN) heavy duty granular laundry (HDG) detergent was 8 hours, and that for Western European (WE) HDG detergent was about 5 hours. The incubation time for heat inactivation of NA and WE auto dish washing (ADW) detergents was about 8 hours. The detergents were purchased from local supermarket stores. Both un-heated and heated detergents were assayed within 5 minutes of dissolving the detergent to accurately determine percentage deactivated. Enzyme activity was tested by AAPF assay using 1 mg/mL AAPF (i.e., substrate of alanine-alanine-proline-phenylalanine).

For testing of enzyme activity in heat-inactivated detergents, working solutions of detergents were made from the heat inactivated stocks. Appropriate amounts of water hardness (6 gpg or 12 gpg) and buffer were added to the detergent solutions to match the desired conditions (Table 10-1). The solutions were mixed by vortexing or inverting the bottles.

TABLE 10-1

Laundry and Dish Washing Conditions

| Region | Form | Dose | Detergent* | Buffer | gpg | pH | T (° C.) |
|---|---|---|---|---|---|---|---|
| Laundry (heavy duty liquid and granular) | | | | | | | |
| NA | HDL | 0.78 g/l | P&G TIDE ® 2X | 5 mM HEPES | 6 | 8.0 | 20 |
| WE | HDL | 5.0 g/L | Henkel Persil | 5 mM HEPES | 12 | 8.2 | 40 |
| WE | HDG | 8.0 g/L | P&G Ariel | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |

TABLE 10-1-continued

Laundry and Dish Washing Conditions

| Region | Form | Dose | Detergent* | Buffer | gpg | pH | T (° C.) |
|---|---|---|---|---|---|---|---|
| NA | HDG | 1.0 g/L | P&G TIDE ® Automatic Dish Washing | 2 mM Na$_2$CO$_3$ | 6 | 10.0 | 20 |
| WE | ADW | 3.0 g/L | RB Calgonit | 2 mM Na$_2$CO$_3$ | 21 | 10.0 | 40 |
| NA | ADW | 3.0 g/L | P&G Cascade | 2 mM Na$_2$CO$_3$ | 9 | 10.0 | 40 |

*Abbreviations: Proctor & Gamble (P&G); and Reckitt Benckiser (RB).

Calculation of Enzyme Performance. The obtained absorbance value was corrected for the blank value (i.e., obtained after incubation of microswatches in the absence of enzyme). The resulting absorbance was a measure for the hydrolytic activity. The results are shown in Tables 10-2 and 10-3. Enzyme performance was assessed using heat inactivated detergents as described above. Winners are defined as those having Performance Index (PI) of greater than 1. PI is the ratio of mutant residual activity to WT residual activity. All the variants tested had a PI greater than 1.

TABLE 10-2

TS23t-7mut CCL-CS-28 rice starch microswatch winners, Tide 2x

| Variant # | 87 | 225 | 272 | 282 | rel charge | PI |
|---|---|---|---|---|---|---|
| 11 | Q87E | N225R | N272E | N282E | −2 | 1.24 |
| 12 | Q87E | N225R | N272E | N282R | 0 | 1.20 |
| 13 | Q87E | N225R | N272E |  | −1 | 1.16 |
| 14 | Q87E | N225R | N272R | N282E | 0 | 1.15 |
| 17 | Q87E | N225R |  | N282E | −1 | 1.34 |
| 18 | Q87E | N225R |  | N282R | 1 | 1.26 |
| 19 | Q87E | N225R |  |  | 0 | 1.34 |
| 20 | Q87E |  | N272E | N282E | −3 | 1.17 |
| 21 | Q87E |  | N272E | N282R | −1 | 1.34 |
| 22 | Q87E |  | N272E |  | −2 | 1.13 |
| 27 | Q87E |  |  | N282R | 0 | 1.22 |
| 28 | Q87E |  |  |  | −1 | 1.22 |
| 29 | Q87R | N225E | N272E | N282E | −2 | 1.44 |
| 30 | Q87R | N225E | N272E | N282R | 0 | 1.15 |
| 31 | Q87R | N225E | N272E |  | −1 | 1.36 |
| 35 | Q87R | N225E |  | N282E | −1 | 1.15 |
| 40 | Q87R | N225R | N272E |  | 1 | 1.27 |
| 44 | Q87R | N225R |  | N282E | 1 | 1.38 |
| 45 | Q87R | N225R |  | N282R | 3 | 1.21 |
| 47 | Q87R |  | N272E | N282E | −1 | 1.65 |
| 48 | Q87R |  | N272E | N282R | 1 | 1.52 |
| 49 | Q87R |  | N272E |  | 0 | 1.28 |
| 50 | Q87R |  | N272R | N282E | 1 | 1.10 |
| 53 | Q87R |  |  | N282E | 0 | 1.47 |
| 54 | Q87R |  |  | N282R | 2 | 1.25 |
| 55 | Q87R |  |  |  | 1 | 1.51 |
| 64 |  | N225E |  |  | −1 | 1.15 |
| 65 |  | N225R | N272E | N282E | −1 | 1.26 |
| 66 |  | N225R | N272E | N282R | 1 | 1.22 |
| 67 |  | N225R | N272E |  | 0 | 1.19 |
| 74 |  |  | N272E | N282E | −2 | 1.21 |
| 76 |  |  | N272E |  | −1 | 1.13 |
| 80 |  |  |  | N282E | −1 | 1.27 |
| 81 |  |  |  | N282R | 1 | 1.49 |

TABLE 10-3

TS-23t-7mut CCL CS-28 rice starch microswatch winners, Persil

| Variant # | 87 | 225 | 272 | 282 | rel charge | PI |
|---|---|---|---|---|---|---|
| 4 | Q87E | N225E | N272E | 0 | −3 | 1.13 |
| 6 | Q87E | N225E | N272R | N282R | 0 | 1.11 |
| 9 | Q87E | N225E |  | N282R | −1 | 1.20 |
| 10 | Q87E | N225E |  | 0 | −2 | 1.17 |
| 11 | Q87E | N225R | N272E | N282E | −2 | 1.41 |
| 13 | Q87E | N225R | N272E | 0 | −1 | 1.40 |
| 14 | Q87E | N225R | N272R | N282E | 0 | 1.28 |
| 15 | Q87E | N225R | N272R | N282R | 2 | 1.13 |
| 16 | Q87E | N225R | N272R | 0 | 1 | 1.17 |
| 17 | Q87E | N225R |  | N282E | −1 | 1.51 |
| 18 | Q87E | N225R |  | N282R | 1 | 1.47 |
| 19 | Q87E | N225R |  | 0 | 0 | 1.48 |
| 20 | Q87E |  | N272E | N282E | −3 | 1.46 |
| 21 | Q87E |  | N272E | N282R | −1 | 1.40 |
| 22 | Q87E |  | N272E | 0 | −2 | 1.42 |
| 25 | Q87E |  | N272R | 0 | 0 | 1.18 |
| 26 | Q87E |  |  | N282E | −2 | 1.54 |
| 27 | Q87E |  |  | N282R | 0 | 1.47 |
| 28 | Q87E |  |  | 0 | −1 | 1.40 |
| 29 | Q87R | N225E | N272E | N282E | −2 | 1.46 |
| 30 | Q87R | N225E | N272E | N282R | 0 | 1.59 |
| 31 | Q87R | N225E | N272E | 0 | −1 | 1.14 |
| 34 | Q87R | N225E | N272R | 0 | 1 | 1.29 |
| 35 | Q87R | N225E |  | N282E | −1 | 1.47 |
| 36 | Q87R | N225E |  | N282R | 1 | 1.62 |
| 37 | Q87R | N225E |  | 0 | 0 | 1.53 |
| 38 | Q87R | N225R | N272E | N282E | 0 | 1.13 |
| 39 | Q87R | N225R | N272E | N282R | 2 | 1.13 |
| 40 | Q87R | N225R | N272E | 0 | 1 | 1.17 |
| 41 | Q87R | N225R | N272R | N282E | 2 | 1.31 |
| 44 | Q87R | N225R |  | N282E | 1 | 1.26 |
| 47 | Q87R |  | N272E | N282E | −1 | 1.45 |
| 48 | Q87R |  | N272E | N282R | 1 | 1.50 |
| 49 | Q87R |  | N272E | 0 | 0 | 1.17 |
| 50 | Q87R |  | N272R | N282E | 1 | 1.16 |
| 53 | Q87R |  |  | N282E | 0 | 1.21 |
| 54 | Q87R |  |  | N282R | 2 | 1.30 |
| 55 | Q87R |  |  | 0 | 1 | 1.33 |
| 56 |  | N225E | N272E | N282E | −3 | 1.29 |
| 57 |  | N225E | N272E | N282R | −1 | 1.12 |
| 58 |  | N225E | N272E | 0 | −2 | 1.41 |
| 59 |  | N225E | N272R | N282E | −1 | 1.16 |
| 61 |  | N225E | N272R | 0 | 0 | 1.20 |
| 66 |  | N225R | N272E | N282E | 1 | 1.27 |
| 67 |  | N225R | N272E | 0 | 0 | 1.34 |
| 71 |  | N225R |  | N282E | 0 | 1.17 |
| 73 |  | N225R |  | 0 | 1 | 1.12 |
| 74 |  |  | N272E | N282E | −2 | 1.29 |
| 75 |  |  | N272E | N282R | 0 | 1.24 |
| 76 |  |  | N272E | 0 | −1 | 1.20 |
| 78 |  |  | N272R | N282R | 2 | 1.18 |
| 79 |  |  | N272R | 0 | 1 | 1.11 |
| 80 |  |  |  | N282E | −1 | 1.11 |
| 81 |  |  |  | N282R | 1 | 1.33 |

Example 11

Combined LAS/Chelant Stability

This example describes determining the relationship between protein charge and stability in a reaction medium containing an anionic surfactant and a chelant. LAS stability was measured after incubation of the test amylases in the presence of 0.1% LAS (dodecylbenzenesulfonate sodium) and 10 mM EDTA, by measuring the residual activity in a BODIPY assay according to the methods described above. For determination of the alpha-amylase activity of the stressed and unstressed samples, the BODIPY-starch assay was used. Residual LAS and EDTA from the stress plates do not affect the BODIPY-starch assays.

Reagents used included: control buffer (50 mM HEPES, 0.005% Tween-80, pH 8.0) and stress buffer (50 mM HEPES, 0.1% (w/v) LAS (dodecylbenzene-sulfonate, sodium salt, Sigma D-2525), 10 mM EDTA, pH 8.0). Enzyme variants (20 ppm) were diluted 1:20 into 96-well non-binding flat-bottom plate containing either the control or stress buffer, and mixed. The control plate was incubated at room temperature, while the stress plate was immediately placed at 37° C. for 30-60 min (depending on the stability of the enzyme being tested). Following incubation, enzyme activity was measured using the BODIPY-starch assay for amylases. The fraction of remaining or residual activity is equal to the reaction rate of the stressed sample divided by the reaction rate of the control sample. The parent enzymes and variants are stable for 60 min in the control buffer.

Table 11-1 shows data for those variants having enhanced LAS/EDTA stability as a function of net charge change relative to wild type TS-23t-7mut, for a library containing 80 variants. This library was designed and constructed according to the methods described in example 2 to span several net charges relative to the parent TS-23t-7mut molecule. A Performance Index (PI) greater than 1 indicates the variant has higher specific activity than the S242Q parent on this starch substrate (i.e., a cornstarch). All the variants tested had a PI over 1.0 with several variants having a PI over 2.0.

TABLE 11-1

TS23t-7mut CCL-LAS/EDTA stability winners

| Variant # | 87 | 225 | 272 | 282 | Charge | Mut residual act./WT residual act. (PI) |
|---|---|---|---|---|---|---|
| 2 | Q87E | N225E | N272E | N282E | −4 | 1.39 |
| 5 | Q87E | N225E | N272R | N282E | −2 | 1.51 |
| 8 | Q87E | N225E |  | N282E | −3 | 1.29 |
| 11 | Q87E | N225R | N272E | N282E | −2 | 1.38 |
| 14 | Q87E | N225R | N272R | N282E | 0 | 1.64 |
| 17 | Q87E | N225R |  | N282E | −1 | 1.39 |
| 20 | Q87E |  | N272E | N282E | −3 | 1.39 |
| 23 | Q87E |  | N272R | N282E | −1 | 1.65 |
| 26 | Q87E |  |  | N282E | −2 | 1.41 |
| 29 | Q87R | N225E | N272E | N282E | −2 | 2.02 |
| 31 | Q87R | N225E | N272E | 0 | −1 | 1.39 |
| 32 | Q87R | N225E | N272R | N282E | 0 | 2.21 |
| 33 | Q87R | N225E | N272R | N282R | 2 | 1.29 |
| 34 | Q87R | N225E | N272R | 0 | 1 | 1.47 |
| 35 | Q87R | N225E |  | N282E | −1 | 2.08 |
| 37 | Q87R | N225E |  | 0 | 0 | 1.41 |
| 38 | Q87R | N225R | N272E | N282E | 0 | 1.85 |
| 40 | Q87R | N225R | N272E | 0 | 1 | 1.38 |
| 41 | Q87R | N225R | N272R | N282E | 2 | 2.15 |
| 43 | Q87R | N225R | N272R | 0 | 3 | 1.63 |
| 44 | Q87R | N225R |  | N282E | 1 | 2.33 |
| 46 | Q87R | N225R |  | 0 | 2 | 1.62 |
| 47 | Q87R |  | N272E | N282E | −1 | 2.38 |
| 48 | Q87R |  | N272E | N282R | 1 | 1.24 |
| 49 | Q87R |  | N272E | 0 | 0 | 1.53 |
| 50 | Q87R |  | N272R | N282E | 1 | 2.14 |
| 51 | Q87R |  | N272R | N282R | 3 | 1.25 |
| 52 | Q87R |  | N272R | 0 | 2 | 1.60 |
| 53 | Q87R |  |  | N282E | 0 | 2.27 |
| 54 | Q87R |  |  | N282R | 2 | 1.34 |
| 55 | Q87R |  |  | 0 | 1 | 1.62 |

TABLE 11-1-continued

TS23t-7mut CCL-LAS/EDTA stability winners

| Variant # | 87 | 225 | 272 | 282 | Charge | Mut residual act./WT residual act. (PI) |
|---|---|---|---|---|---|---|
| 56 | 0 | N225E | N272E | N282E | −3 | 1.69 |
| 59 | 0 | N225E | N272R | N282E | −1 | 1.77 |
| 62 | 0 | N225E |  | N282E | −2 | 1.50 |
| 65 | 0 | N225R | N272E | N282E | −1 | 1.66 |
| 67 | 0 | N225R | N272E | 0 | 0 | 1.24 |
| 68 | 0 | N225R | N272R | N282E | 1 | 1.80 |
| 70 | 0 | N225R | N272R | 0 | 2 | 1.25 |
| 71 | 0 | N225R |  | N282E | 0 | 1.48 |
| 73 | 0 | N225R |  | 0 | 1 | 1.29 |
| 74 | 0 |  | N272E | N282E | −2 | 1.54 |
| 77 | 0 |  | N272R | N282E | 0 | 1.78 |
| 80 | 0 |  |  | N282E | −1 | 1.52 |

Figure 17:
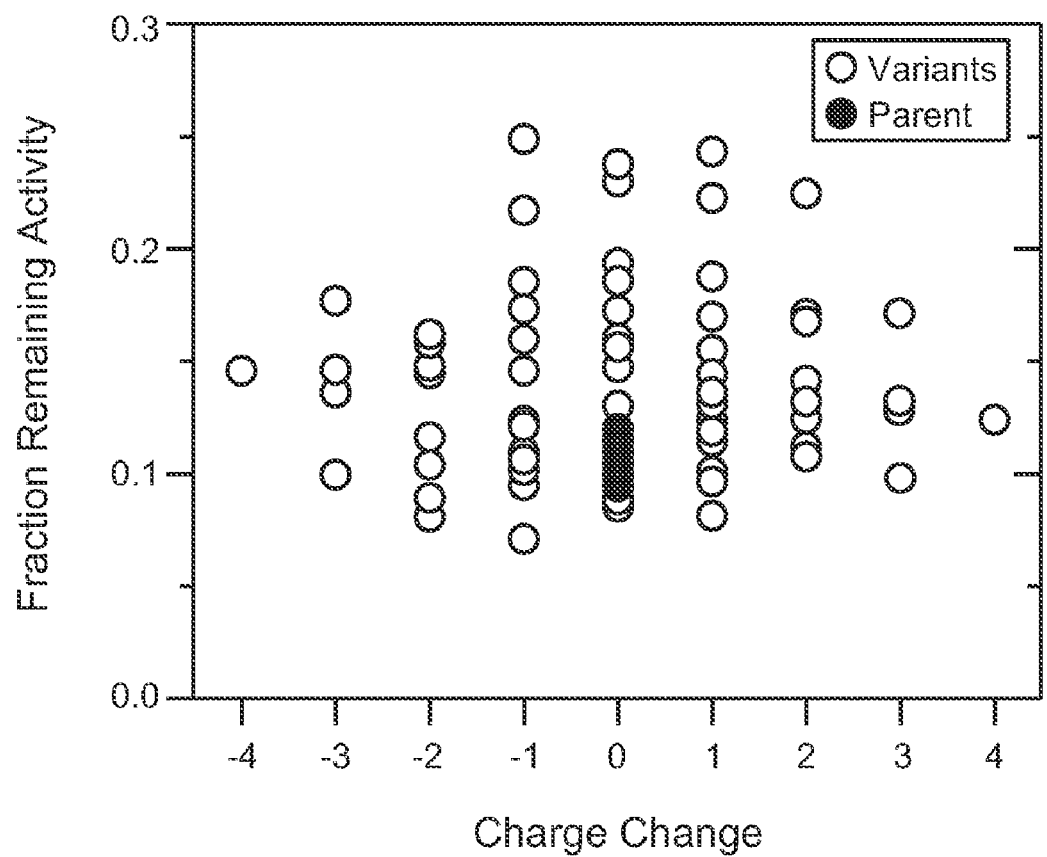
FIG. 17. The graph depicts residual activity as a function of charge change. Reference is made to Example 11.

For ASP (acidic serine protease) and FNA (another protease) there is a charge dependence for LAS/EDTA stability (see PCT/US2008/007103 filed Jun. 6, 2008, Genencor Int'l). Adding negative charge increases stability. But, even when going one or two charges more positive than the parent, it is possible to find, by our method, an arrangement of charge mutations which confer equal or greater stability than the parent. This approach is also effective in larger enzymes, such as TS23t' shown in FIG. 17, where the detrimental effect of adding positive charges on stability can be compensated by an optimal charge arrangement that increases stability.

Example 12

Baking Composition

This example demonstrate the use of TS-23 in a baking composition.

Amylase Assays. Ceralpha Assay. One Ceralpha unit is defined as activity degrading 0.0351 mmole per 1 min. of PNP-coupled non-reducing end blocked maltoheptaose so that 0.0351 mmole PNP per 1 min. can be released by excess glucoamylase and alpha-glucosidase in the assay mix (PNP—paranitrophenol). The assay mix contains 50 µL 50 mM Na-citrate, 5 mM $CaCl_2$, pH 6.5 with 25 µL enzyme sample and 25 µL Ceralpha substrate (non-reducing end blocked Glc7-PNP, glucoamylase and alpha-glucosidase) from Megazyme, Ireland (1 vial dissolved in 10 mL water). The assay mix is incubated for 30 min. at 40° C. and then stopped by adding 150 µL 4% Tris. Absorbance at 420 nm is measured using an ELISA-reader, and the Ceralpha activity is calculated based on Activity=A420*d in Ceralpha units/mL of enzyme sample assayed.

Betamyl assay. One Betamyl unit is defined as activity degrading 0.0351 mmole per 1 min. of PNP-coupled maltopentaose so that 0.0351 mmole PNP per 1 min. can be released by excess α-glucosidase in the assay mix. The assay mix contains 50 µL 50 mM Na-citrate, 5 mM $CaCl_2$, pH 6.5 with 25 µL enzyme sample and 25 µL Betamyl substrate (Glc5-PNP and a-glucosidase) from Megazyme, Ireland (1 vial dissolved in 10 mL water). The assay mix is incubated for 30 min. at 40° C. and then stopped by adding 150 µL 4% Tris. Absorbance at 420 nm is measured using an ELISA-reader, and the Betamyl activity is calculate based on Activity=A420*d in Betamyl units/mL of enzyme sample assayed. 1 BMK (kilo betamyl units) is defined as 1000 Betamyl units.

Baking Trial Test. Baking trials were carried out with a standard white bread sponge and dough recipe for US toast.

The sponge dough is prepared from 1600 g of flour "All Purpose Classic" from Sisco Mills, USA", 950 g of water, 40 g of soy bean oil, and 32 g of dry yeast. The sponge is mixed for 1 min. at low speed and subsequently 3 min. at speed 2 on a Hobart spiral mixer. The sponge is subsequently fermented for 2.5 hours at 35° C., 85% RH followed by 0.5 hour at 5° C.

Thereafter, 400 g of flour, 4 g of dry yeast, 40 g of salt, 2.4 g of calcium propionate, 240 g of high fructose corn syrup (Isosweet), 5 g of the emulsifier PANODAN 205, 5 g of enzyme active soy flour, 30 g of non-active soy flour, 220 g of water and 30 g of a solution of ascorbic acid (prepared from 4 g ascorbic acid solubilised in 500 g of water) are added to the sponge. The resulting dough is mixed for 1 min. at low speed and then 6 min. on speed 2 on a Diosna mixer. Thereafter, the dough is rested for 5 min. at ambient temperature, and then 550 g dough pieces are scaled, rested for 5 min. and then sheeted on Glimek sheeter with the settings 1:4, 2:4, 3:15, 4:12, and 10 on each side and transferred to a baking form. After 60 min. proofing at 43° C. at 90% RH, the doughs are baked for 29 min. at 218° C.

Firmness and resilience were measured with a TA-XT 2 texture analyser. The softness, cohesiveness and resilience is determined by analysing bread slices by Texture Profile Analysis using a Texture Analyser From Stable Micro Systems, UK. The following settings were used:

Pre Test Speed: 2 mm/s
Test Speed: 2 mm/s
Post Test Speed: 10 mm/s
Rupture Test Distance: 1%
Distance: 40%
Force: 0.098 N
Time: 5.00 sec
Count: 5
Load Cell: 5 kg
Trigger Type Auto—0.01 N Firmness and Cohesiveness Effects in Baking Trial. TS23fl in combination with a variant of the wild type maltotetraohydrolase (PS4 wt) from *Pseudomonas saccharophila* does reduce firmness relative to the variant PS4 alone, whereas TS23fl alone does not reduce firmness significantly (FIG. 15).

The variant PS4 amylase has the following sequence (SEQ ID NO: 18)

```
mdqagkspag vryhggdeii lqgfhwnvvr eapynwynil rqqastiaad gfsaiwmpvp wrdfsswtdg dksgggegyf whdfnkngry gsdaqlrqaa galggagvkv lydvvpnhmn rfypdkeinl pagqrfwrnd cpdpgngpnd cddgdrflgg eadlntghpq iygmfrdeft nlrsgygagg frfdfvrgya pervdswmsd sadssfcvge lwkepseypp wdwrntaswq giikdwsdra kcpvfdfalk ermqngsvad wkhglngnpd prwrevavtf vdnhdtgysp gqnggqhkwp lqdglirqay ayiltspgtp vvywphmydw gygdfirqli gvrrtagvra dsaisfhsgy sglvatvsgs qqtlvvalns dlanpggvas gsfseavnas ngqvrvwrsg sgdgggndgg
```

Figure 15:
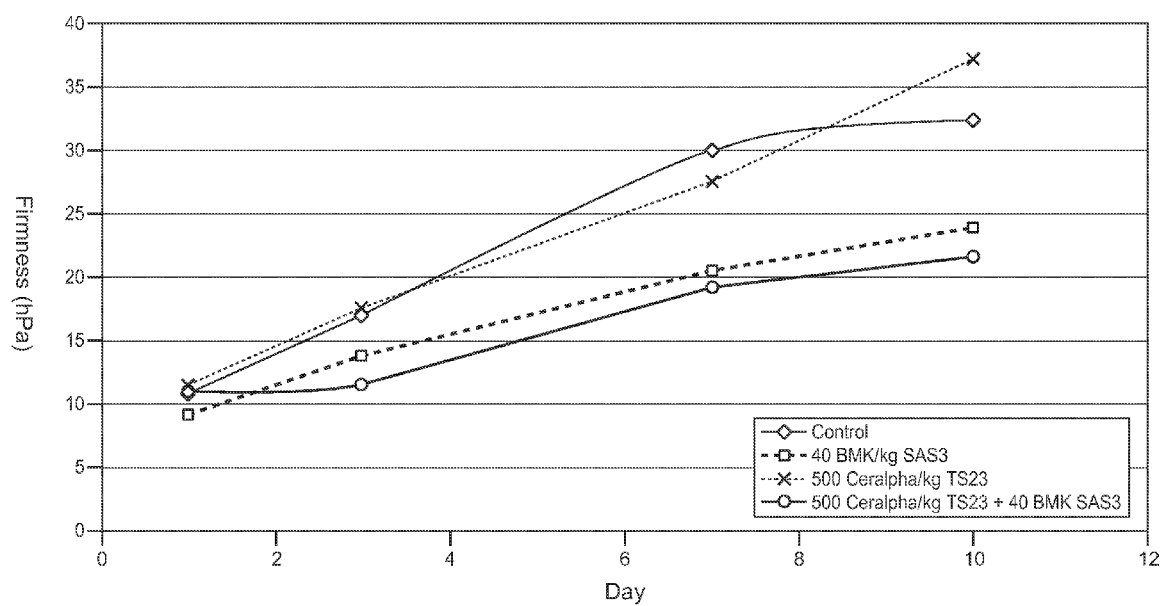
FIG. 15. The graph depicts the cohessiveness effect of TS23 and a variant PS4 as well as TS23 combined with a variant PS4 in US toast.
Figure 16:
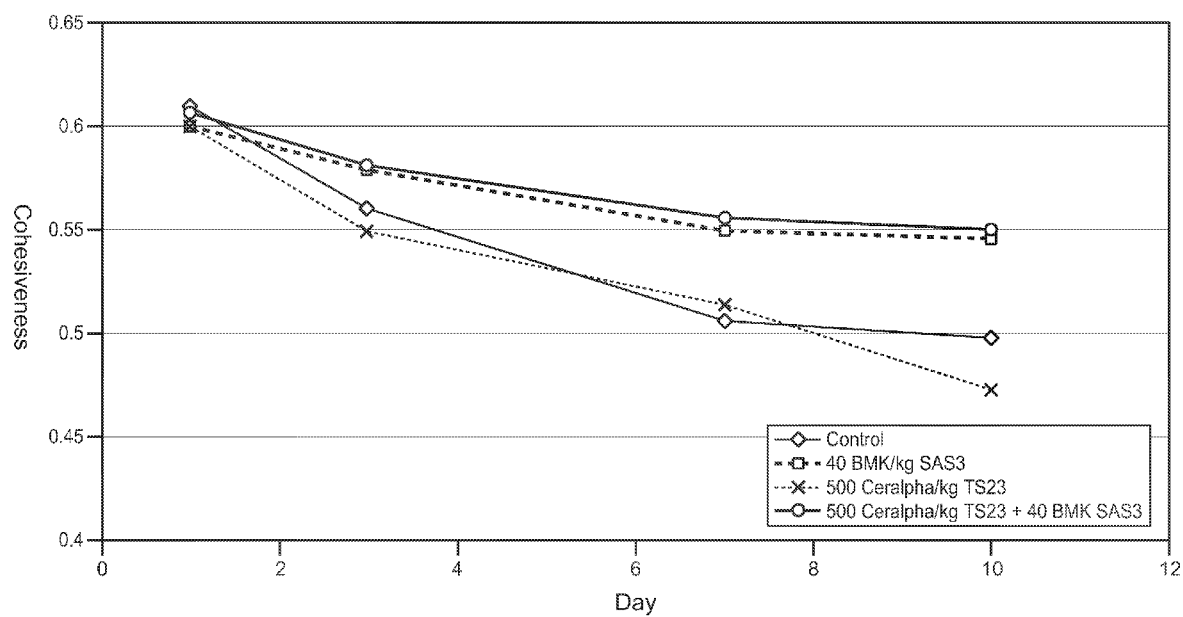
FIG. 16. The graph depicts the firmness effect of TS-23 and a variant PS4 as well as TS-23 combined with a variant PS4 in US toast.

FIGS. 15 and 16 show the results of a baking trial comparing doughs with and without mature, full-length TS-23. TS-23 in combination with variant PS4 does improve cohesiveness relative to variant PS4 alone, whereas TS23 alone does not change cohesiveness significantly (FIG. 16). In conclusion, TS-23 can be used to enhance the firmness reducing and cohesiveness improving effects of variant PS4 (FIGS. 15 and 16).

Example 13

Truncated TS-23 Alpha-Amylase

Figure 19:
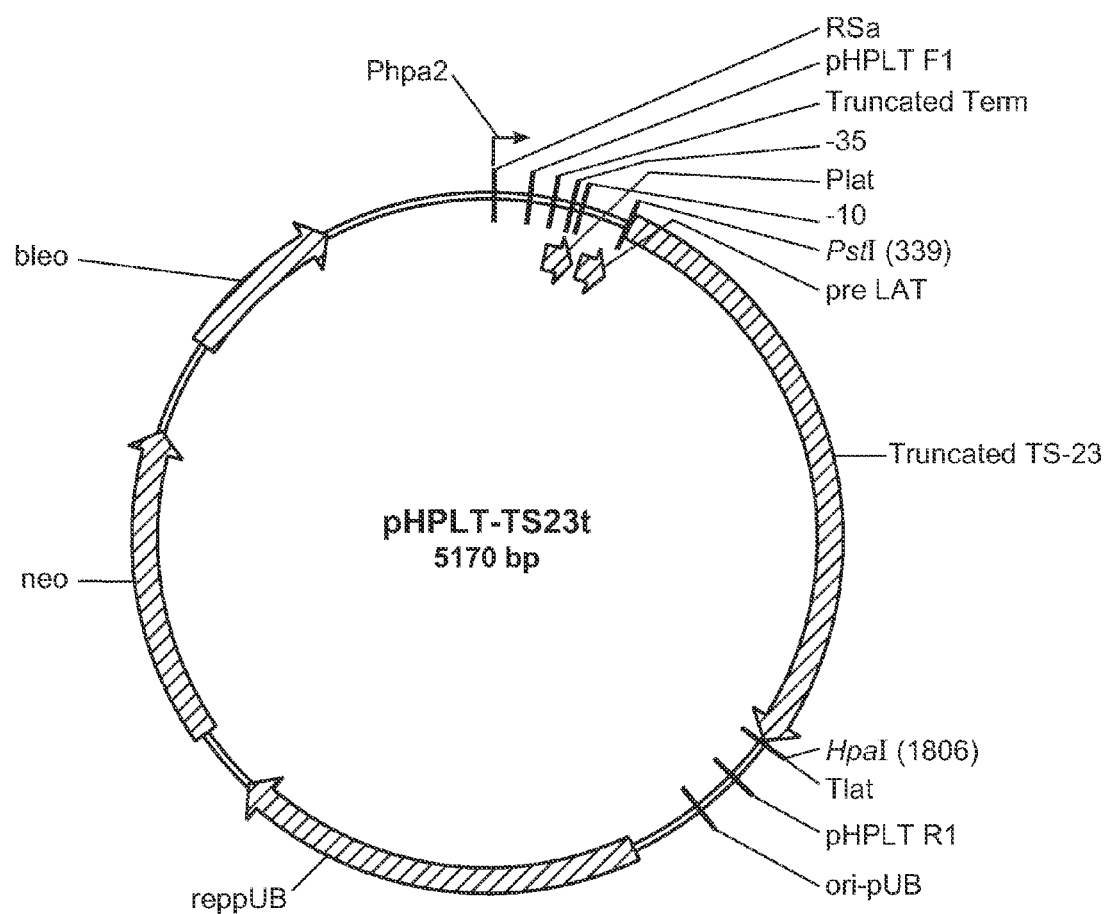
FIG. 19. The *Bacillus* expression vector pHPLT-TS23t, used for expression of Base (and Ace) in *B. subtilis* SC6.1.

Vector construction and transformation. The *Bacillus* sp. TS23 amylase gene was synthesized by Geneart. The sequence of the synthetic gene is depicted in FIGS. 18A and B. Using this sequence as a template, the *Bacillus* sp. TS23 alpha-amylase gene was amplified without its starch binding domain in a standard PCR reaction using primer pHPLT-PstI-FW and pHPLT-HpaI-RV. The resulting truncated fragment was cloned via the PstI and HpaI restriction sites into the *Bacillus* expression vector pHPLT. The resulting vector pHPLT-TS23t (FIG. 19) was transformed to *Bacillus subtilis* SC6.1 (also called BG3594comK) (DaprE, DnprE, degU$^{Hy}$32, oppA, DspoIIE3501, amyE::xylRPxylAcomK-phleo), and transformants were selected on 10 mg/L neomycin. The encoded truncated TS23 alpha-amylase is further referred to as Base in the corresponding figures.

A second construct was made, identical to pHPLT-TS23t with the exception of a 2 codon deletion ($R^{180}S^{181}$). Using primer pairs pHPLT-PstI-FW and TS-delRS-RV, and TS-delRS-FW and pHPLT-HpaI-RV (Table 13-1) respectively, in a PCR on the synthetic TS23 alpha-amylase gene (FIG. 1), two fragments were amplified. These 2 fragments were fused together in a PCR with primer pair pHPLT-PstI-FW and pHPLT-HpaI-RV. The resulting fragment was subsequently cloned in pHPLT and transformed to *B. subtilis* SC6.1 as described above. The encoded protein (Base $\Delta R^{180}S^{181}$) is also further referred to as Ace for this example and the corresponding figures.

Growth and microtiter plate expression. Transformants were grown on 200 µL Grant's II media (appendix I) supplemented with 5 mM CaCl$_2$ and 10 mg/L neomycin in 96 well microtiter plates (MTP's) with a flat bottom (Corning no. 3599). Plates were incubated at 37° C., 80% humidity and 300 rpm in an Infors incubator for 3 days. MTP's were centrifuged and the culture supernatant was filtrated over a filtration plate. Expression levels reached approximately 100 mg/L.

Thermostability assay. The thermostability of the amylases was measured by diluting culture supernatant 1000× in 50 mM MOPS buffer, 50 mM NaCl, 0.1 mM CaCl$_2$, pH 7.15. The diluted samples were then incubated on an Eppendorf Master cycler EP gradient S PCR machine for 1 hour at different temperatures, and cooled down to 4° C. Initial and residual activity was measured using the Amylase HR reagent (Megazyme). 25 µL of sample was added to 25 µL of Amylase HR reagent and mixed thoroughly. The reaction was allowed to proceed for 30 min at 25° C. and 900 RPM in an iEMS incubator (Thermo Scientific). The reaction was stopped by adding 50 µL stopbuffer (200 mM boric acid, pH 10.2), and the absorbance at 400 nm was measured using a Spectramax plus spectrophotometer (Molecular Devices).

Inactivating enzyme activity in liquid detergent. To inactivate enzyme activity in commercially obtained liquid Persil color (Henkel). The detergent was placed in closed glass bottle and incubated for 2 h at 95° C. in a water bath. After incubation, the detergent was tested for possible residual amylase activity by using the earlier described Amylase HR reagent.

10% detergent stability. The 10% detergent stability was measured by adding 10 µL of enzyme sample (culture supernatant) to 190 µL of a 10.5% detergent solution in 25 mM HEPES buffer, 0.005% Tween 80, pH 8. The mixture was incubated on an Eppendorf Master cycler EPgradient S PCR machine for 30 min or 1 hour at different temperatures, and cooled down to 4° C. The initial and residual activity was measured using the Amylase HR reagent, after appropriate dilution of the samples in 50 mM MOPS, 50 mM NaCl, 0.005% Tween 80, pH 7.15.

100% Detergent stability. For the 100% detergent stability measurement, 5% v/v enzyme sample was mixed thoroughly in 100% inactivated detergent. The samples were subsequently incubated on a thermal cycler as described above. Initial and residual activity were measured using CS28 rice-starch micro-swatches (CFT, Vlaardingen). Flat bottom MTP's were filled with 2 CS28 µswatches (diameter 6 mm) per well. Samples were diluted appropriately and the cleaning activity of the enzyme was measured on the CS28 µswatches in 200 µL 25 mM HEPES buffer, 0.1 mM $CaCl_2$, 0.005% Tween 80, pH 8. The MTP's were incubated at 32° C. for 1 h at 1150 rpm in an iEMS incubator. After incubation 100 mL of the reaction was transferred to a new MTP. The absorbance at 488 nm was measured using a Spectramax plus spectrophotometer (Molecular Devices).

Data analysis. The obtained data was analysed using SlideWrite plus for Windows (Advanced graphics software) and fitted to the equation:

$$y = c0 + c1/(1+(x/c2)^{c3}).$$

Results.

Figure 20:
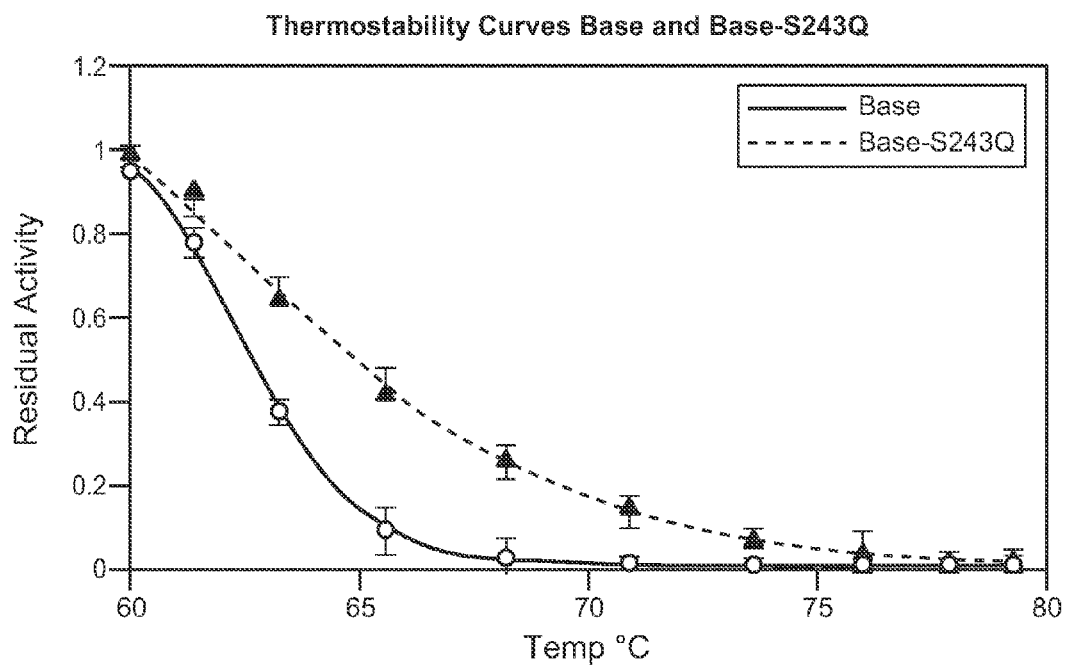
FIG. 20. Residual activity of Base and Base-S243Q after 1 hour incubation in MOPS using a temperature gradient on a PCR machine.
Figure 21:
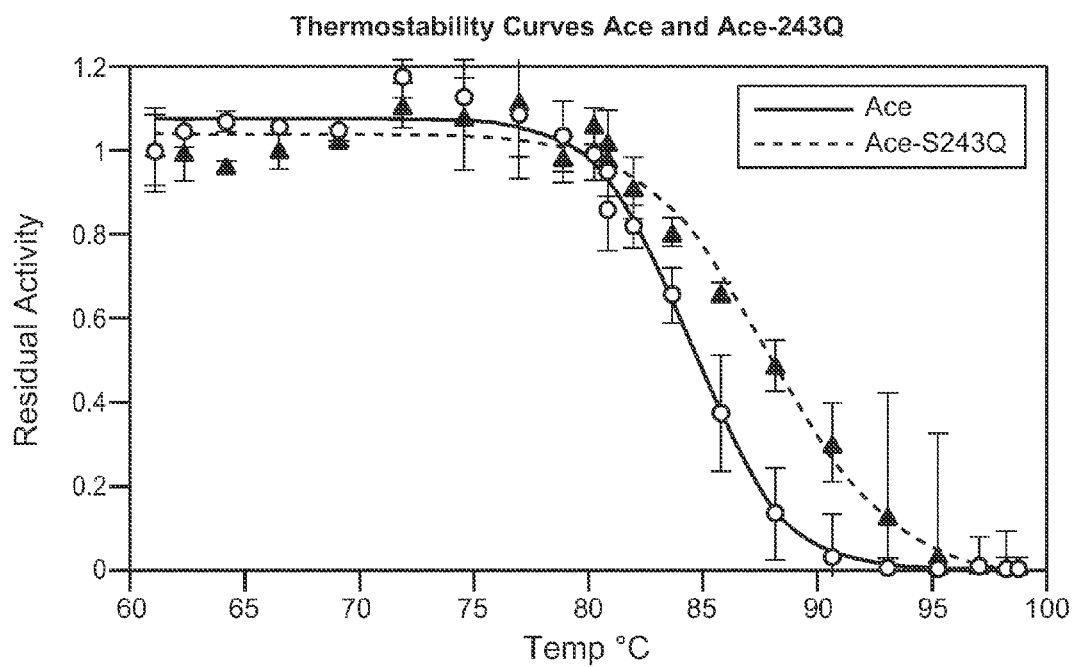
FIG. 21. Residual activity of Ace and Ace-S243Q after 1 hour incubation in MOPS buffer using a temperature gradient on a PCR machine.
Figure 22:
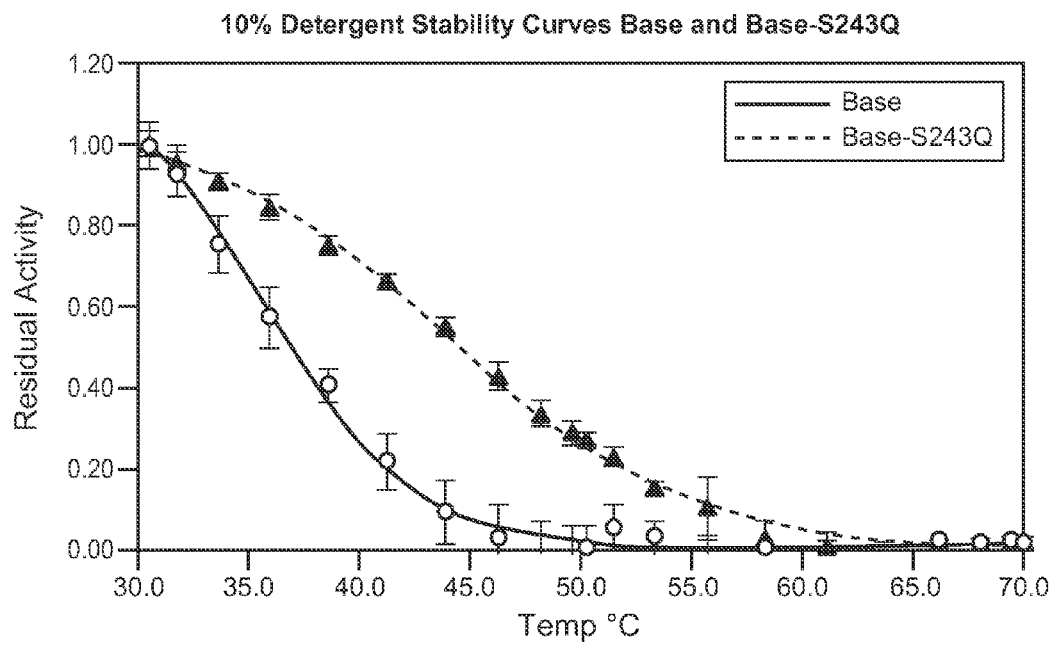
FIG. 22. Residual activity of Base and Base-S243Q after 30 min incubation in 10% Persil color (inactivated) using a temperature gradient on a PCR machine.
Figure 23:
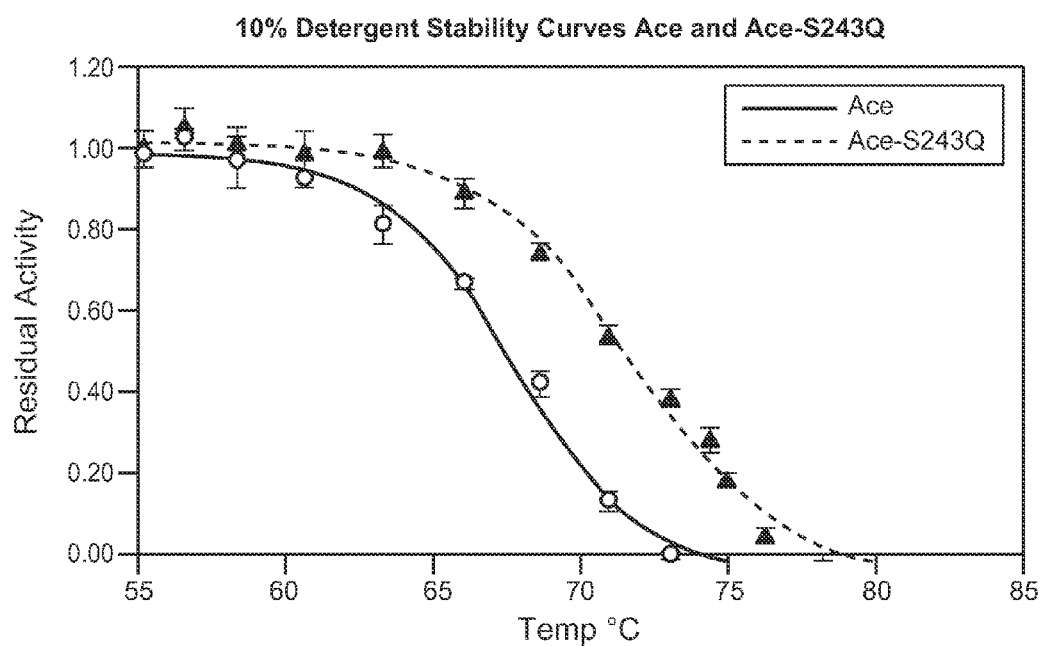
FIG. 23. Residual activity of Ace and Ace-S243Q after 1 hour incubation in 10% Persil color (inactivated) using a temperature gradient on a PCR machine.
Figure 24:
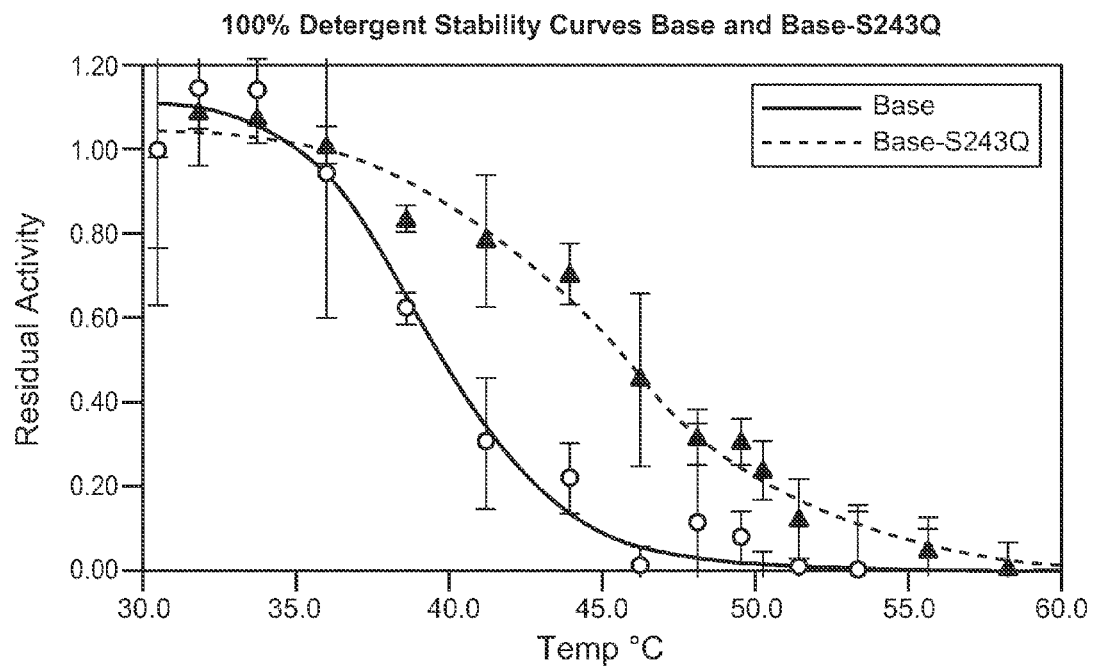
FIG. 24. Residual activity of Base and Base-S243Q after 1 hour incubation in 100% Persil color (inactivated) using a temperature gradient on a PCR machine.
Figure 25:
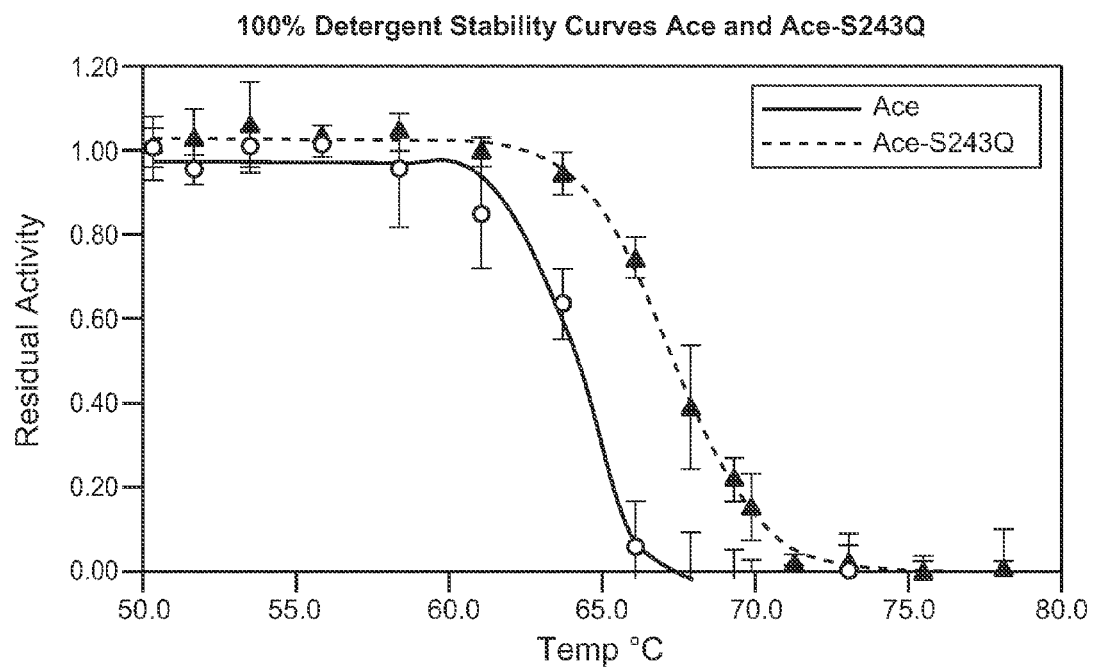
FIG. 25. Residual activity of Ace and Ace-S243Q after 1 hour incubation in 100% Persil color (inactivated) using a temperature gradient on a PCR machine.

Thermostability. The thermostability of Base (t50%) is raised approximately 2° C. by introduction of the S243Q mutation (FIG. 20; Table 13-2). A two (2) amino acid deletion ($R^{180}S^{181}$), which turns Base into Ace on the other hand raised the thermostability of the enzyme by 20° C. (FIG. 21; Table 13-2). Interestingly, introducing the S243Q mutation the Ace backbone (amino acid numbering according to Base) raised the thermostability of Ace an additional 3° C. (FIG. 21; Table 13-2).

10% and 100% detergent stability. An important application for the Base/Ace amylase will be laundry detergents. Thus, the stability of the amylase in liquid detergents is an important feature. Stability of the enzymes was determined using a 10% and 100% detergent over a temperature gradient (FIGS. 22-25). The stability of Base is increased both in the 10% detergent solution and the 100% detergent by introduction of the S243Q mutation (Table 13-2). In the 10% detergent, the stability is raised 7.6° C., whereas in 100% detergent the increase is approximately 5.9° C. Also in the case of Ace, the S243Q mutation has a beneficial effect on the detergent stability. In 10% detergent, the stability is increased 3.7° C. In 100% detergent, there is a stability increase of 3.4° C.

TABLE 13-2

Temperatures needed to inactivate 50% of the enzyme under the given conditions. (cf. FIG. 20-25).

| | T 50% | | |
|---|---|---|---|
| | Thermostability | 10% Detergent | 100% Detergent |
| Base | 62.7° C. | 36.9° C. | 39.8° C. |
| Base-S243Q | 64.9° C. | 44.5° C. | 45.7° C. |
| Ace | 84.7° C. | 68.2° C. | 64.1° C. |
| Ace-S243Q | 87.9° C. | 71.9° C. | 67.5° C. |

Reagents.
Grant's II Media
Part 1: 10 g Soyton is prepared in 500 ml water and autoclaved
Part 2: 3 ml of 1M $K_2HPO_4$, 75 g glucose, 3.6 g urea, 100 mL Grant's 10×MOPS, 400 ml total
Part 1 and part 2 are mixed, the pH adjusted to 7.3 with HCl/NaOH, the volume adjusted to 1 liter, and the media is filter sterilized through a 0.22 µm PES filter.
Grant's 10×MOPS Per Liter:
83.72 g MOPS
7.17 g Tricine
12 g KOH
29.22 g NaCl
10 ml 0.276M K2SO4
10 ml 0.528 M MgCl2
100 ml Grant's micronutrients
Grant's Micronutrients Per Liter:
1.47 Trisodium citrate dihydrate
1.47 g $CaCl_2.2H_2O$.
0.4 g $FeSO_4.7H_2O$
0.1 g $MnSO_4.H_2O$
0.1 g $ZnSO_4.H_2O$
0.05 $CuCl_2.2H_2O$
0.1 g $CoCl_2.6H_2O$
0.1 g $Na_2MoO_4.2H_2O$ All publications and patents mentioned in the above are herein incorporated by reference in their entirety for all purposes. Various modifications and variations of the described methods and system will be apparent to those skilled in the art without departing from the scope and spirit of the invention. Although the invention has been described in connection with specific preferred embodiments, it should be understood that the embodiments as claimed should not be unduly limited to such specific examples. Indeed, various modifications of the described modes for carrying out the embodiments and aspects, which are obvious to those skilled in the art are intended to be within the scope of the following claims.

TABLE 13-1

Primers used in construction of Base and Ace expression plasmids

| Primer Name | Sequence | Purpose |
|---|---|---|
| pHPLT-PstI-FW SEQ ID NO: 8 | CTCATT CTGCAG CTTCAGCAAATACGGCG | Clone TS23 truncated in the pHPLT expression vector |
| pHPLT-HpaI-RV SEQ ID NO: 9 | CTCT GTTAAC TCATTTGGCGACCCAGATTGAAACG | |
| TS-delRS-FW SEQ ID NO: 10 | CTATAAATTTACGGGCAAAGCATGGGATTGG | Introduce deletion at R180-S181 |
| TS-delRS-RV SEQ ID NO: 11 | TGCTTTGCCCGTAAATTTATAGATCCGGTTCAG | |

The invention claimed is:

1. An isolated variant of a parent *Bacillus* sp. TS-23 alpha-amylase, wherein the variant comprises an amino acid sequence with at least 90% amino acid sequence identity to SEQ ID NO: 2, wherein the variant has amylase activity, and wherein said variant comprises a truncation of the C-terminus, the modification S243Q, A, E, or D, and optionally any one or more of modifications (a) to (i), wherein each amino acid position corresponds to a position in SEQ ID NO: 1:
   (a) R180 deletion or S181 deletion or R180 and S181 deletion;
   (b) M201L;
   (c) Q87 to E or R;
   (d) N225 to E or R;
   (e) N272 to E or R;
   (f) N282 to E or R;
   (g) T182 deletion;
   (h) G183 deletion; or
   (i) Q98R, M201L, S243Q, R309A, Q320R, Q359E, and K444E.

2. The variant of claim 1, wherein the variant comprises modifications (a) and (b).

3. The variant of claim 1, wherein said variant has at least 95% sequence identity to SEQ ID NO: 2.

4. The variant of claim 3, wherein said variant has at least 98% sequence identity to SEQ ID NO: 2.

5. The variant of claim 1, wherein said variant has the following characteristics:
   a) requires less than 60 ppm calcium ions for enzymatic activity;
   b) improved oxidative stability relative to the parent *Bacillus* sp. TS-23 alpha-amylase; or
   c) improved thermostability relative to the parent *Bacillus* sp. TS-23 alpha-amylase.

6. An isolated nucleic acid encoding the variant of claim 1.

7. A vector comprising the nucleic acid of claim 6.

8. An isolated host cell comprising the nucleic acid of claim 6.

9. An isolated host cell comprising the vector of claim 7, and wherein the host cell is a prokaryote or an eukaryote.

10. The isolated host cell of claim 9, wherein the isolated host cell is a bacterium or a fungus.

11. The isolated host cell of claim 10, wherein the bacterium is a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans*, and *S. murinus*; or a Gram negative bacterium, wherein said Gram negative bacterium is *Escherichia coli* or a *Pseudomonas* sp.

12. A detergent additive comprising the variant of claim 1.

13. The detergent additive of claim 12, further comprising one or more enzymes from the group consisting of: a cellulase, a protease, an aminopeptidase, an amylase, a carbohydrase, a carboxypeptidase, a catalase, a chitinase, a cutinase, a cyclodextrin glucanotransferase, a deoxyribonuclease, an esterase, an α-galactosidase, a β-galactosidase, a glucoamylase, α-glucosidase, a β-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, a pullulanase, an isoamylase, a carrageenase, and any combination thereof.

14. The detergent additive of claim 13 in the form of a non-dusting granulate, microgranulate, stabilized liquid, or protected enzyme.

15. A detergent composition comprising the detergent additive of claim 13.

16. A detergent composition comprising a surfactant and the variant of claim 1.

17. The detergent composition of claim 16, wherein said detergent composition is a laundry detergent or a dish detergent.

18. The detergent composition of claim 17, further comprising one or more enzymes selected from the group consisting of a cellulase, a protease, an aminopeptidase, an amylase, a carbohydrase, a carboxypeptidase, a catalase, a chitinase, a cutinase, a cyclodextrin glucanotransferase, a deoxyribonuclease, an esterase, an α-galactosidase, a β-galactosidase, a glucoamylase, an α-glucosidase, a β-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, a pullulanase, an isoamylase, a carrageenase, and any combination thereof.

19. A laundry detergent composition comprising the laundry additive of claim 18, and further comprising one or more of a surfactant, detergent builder, complexing agent, polymer, bleaching system, stabilizer, foam booster, suds suppressor, anti-corrosion agent, soil-suspending agent, anti-soil redeposition agent, dye, bactericide, hydrotope, optical brightener, fabric conditioner, and perfume.

20. A biofilm hydrolyzing composition comprising the variant of claim 1 in a solution or gel, and optionally further comprising a cellulase, a hemicellulase, a xylanase, a lipase, a protease, a pectinase, an antimicrobial agent, or any combination thereof.

21. A method of hydrolyzing a biofilm comprising administering the composition of claim 20 for a period sufficient to process said biofilm.

22. A baking composition comprising the variant of a parent *Bacillus* sp. TS-23 alpha-amylase of claim 1 in a solution or gel.

23. A method of baking, comprising administering the baking composition of claim 22.

24. The variant of claim 1, wherein the variant comprises modification (a).

25. The variant of claim 1, wherein the variant comprises modification (b).

26. The variant of claim 1, wherein the variant comprises modifications (a) and (b).

27. The variant of claim 1, wherein the modification S243Q, A, E, or D is S243Q.

28. The composition of claim 17, wherein the detergent composition is a dish detergent.

29. A cleaning composition comprising the variant of claim 1.

30. A method of cleaning a surface or object, comprising contacting the surface or object with the cleaning composition of claim 29.

31. The method of claim 30, wherein the object is a fabric.

32. The method of claim 30, wherein the surface is a hard surface.

33. The method of claim 32, wherein the hard surface is the surface of dishware.

34. The variant of claim 1, wherein said truncation is of five or more amino acids of the C-terminus of the variant.

35. The variant of claim 1, wherein said truncation is of 10 or more amino acids of the C-terminus of the variant.

* * * * *